United States Patent
Schubert et al.

(10) Patent No.: US 9,744,164 B2
(45) Date of Patent: Aug. 29, 2017

(54) NEUROPROTECTIVE POLYPHENOL ANALOGS

(71) Applicant: Salk Institute for Biological Studies, La Jolla, CA (US)

(72) Inventors: David R. Schubert, La Jolla, CA (US); Pamela A. Maher, La Jolla, CA (US); Chandramouli Chiruta, La Jolla, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 15/054,906

(22) Filed: Feb. 26, 2016

(65) Prior Publication Data
US 2016/0206609 A1    Jul. 21, 2016

Related U.S. Application Data

(60) Division of application No. 14/173,658, filed on Feb. 5, 2014, now abandoned, which is a continuation of
(Continued)

(51) Int. Cl.
*A61K 31/4025* (2006.01)
*C07D 311/78* (2006.01)
(Continued)

(52) U.S. Cl.
CPC .............. *A61K 31/47* (2013.01); *A61K 31/12* (2013.01); *A61K 31/352* (2013.01);
(Continued)

(58) Field of Classification Search
CPC .............. C07D 311/78; C07D 215/233; C07D 311/62; C07D 311/60; A61K 31/353;
(Continued)

(56) References Cited

U.S. PATENT DOCUMENTS 6,066,642 A    5/2000  Jacobson et al.
6,500,846 B1  12/2002  Hong et al.
(Continued)

FOREIGN PATENT DOCUMENTS

CN         1823046        8/2006
WO     WO 2004/103973    12/2004
(Continued)

OTHER PUBLICATIONS

Illien; New J. Chem., 1998, 22, 633-641.*
(Continued)

*Primary Examiner* — Noble Jarrell
*Assistant Examiner* — Daniel Carcanague
(74) *Attorney, Agent, or Firm* — Klarquist Sparkman, LLP

(57) ABSTRACT

The present invention provides neuroprotective polyphenol compounds, which can be synthetic analogs of fisetin, baicalein or chlorogenic acid, that maintain neuroprotective, anti-inflammatory, glutathione promoting, and/or antioxidant properties. The neuroprotective polyphenol compounds are useful for promoting, enhancing and/or increasing neuron protection, growth and/or regeneration. The polyphenol compounds further find use for increasing and or maintaining intracellular glutathione (GSH) levels. The polyphenol compounds are also useful for treating, preventing, mitigating and/or delaying neurodegenerative conditions, including diabetes, Parkinson's disease, Huntington's disease, Alzheimer's disease, non-Alzheimer's dementias, multiple sclerosis, traumatic brain injury, spinal cord injury or ALS.

16 Claims, 17 Drawing Sheets

Related U.S. Application Data application No. PCT/US2012/050324, filed on Aug. 10, 2012.

(60) Provisional application No. 61/522,878, filed on Aug. 12, 2011.

(51) Int. Cl.

| | | |
|---|---|---|
| *A61K 31/47* | (2006.01) | |
| *C07D 311/30* | (2006.01) | |
| *A61K 31/4709* | (2006.01) | |
| *A61K 31/452* | (2006.01) | |
| *C07D 311/62* | (2006.01) | |
| *C07D 215/233* | (2006.01) | |
| *A61K 45/06* | (2006.01) | |
| *A61K 31/12* | (2006.01) | |
| *A61K 31/352* | (2006.01) | |
| *A61K 31/353* | (2006.01) | |
| *C07C 49/835* | (2006.01) | |
| *C07C 49/84* | (2006.01) | |
| *C07D 311/60* | (2006.01) | |

(52) U.S. Cl.
CPC ........ *A61K 31/353* (2013.01); *A61K 31/4025* (2013.01); *A61K 31/4709* (2013.01); *A61K 45/06* (2013.01); *C07C 49/835* (2013.01); *C07C 49/84* (2013.01); *C07D 215/233* (2013.01); *C07D 311/30* (2013.01); *C07D 311/60* (2013.01); *C07D 311/62* (2013.01); *C07D 311/78* (2013.01)

(58) Field of Classification Search
CPC ...... A61K 31/47; A61K 31/352; A61K 31/12; C07C 49/84
USPC .......................................... 514/456; 546/153
See application file for complete search history.

(56) References Cited

U.S. PATENT DOCUMENTS

| | | | |
|---|---|---|---|
| 7,846,915 | B2 | 12/2010 | Wong |
| 2003/0069192 | A1 | 4/2003 | Lahey et al. |
| 2003/0105030 | A1 | 6/2003 | Liao et al. |
| 2003/0225110 | A1 | 12/2003 | Zhou |
| 2005/0148599 | A1 | 7/2005 | Bowen et al. |
| 2006/0217399 | A1 | 9/2006 | Vu et al. |
| 2007/0032512 | A1 | 2/2007 | Ji et al. |
| 2008/0021096 | A1 | 1/2008 | Maher |
| 2008/0207608 | A1 | 8/2008 | Kumar et al. |
| 2009/0259048 | A1 | 10/2009 | Wong et al. |
| 2014/0186329 | A1 | 7/2014 | Lapchak et al. |

FOREIGN PATENT DOCUMENTS

| | | |
|---|---|---|
| WO | WO 2010/037129 | 4/2010 |
| WO | WO 2013/020184 | 2/2013 |
| WO | WO 2013/025484 | 2/2013 |

OTHER PUBLICATIONS

Li; J. Med. Chem. 1994, 37, 1126-1135.*
Mphahlele; J. Chem. Res. (S), 1999, 706-707.*
Chemical Abstracts STN Registry Database record for RN 1313738-83-8, entered on Jul. 26, 2011.
Fournet et al., "2-Substituted Quinoline Alkaloids as Potential Antileishmanial Drugs," *Antimicrobial Agents and Chemotherapy* 37(4):859-863, Apr. 1993.
International Search Report and Written Opinion dated Oct. 15, 2012, from International Application No. PCT/US2012/50299.
International Search Report and Written Opinion dated Nov. 8, 2012, from International Application No. PCT/US2012/50324.
Joseph-Nathan and Santillan, "[$^{13}$C]NMR Study of Naphthoflavones," *Spectrochimica Acta* 40A:1077-1080, 1984.
Kim et al., "Flavonoids of *Inula britannica* Protect Cultured Cortical Cells from Necrotic Cell Death Induced by Glutamate," *Free Rad Biol Med.* 32:596-604, Apr. 1, 2002.
Kumar et al., "An efficient oxidation of 2-aryl-1,2,3,4-tetrahydro-4-quinolones employing ferric chloride hexahydrate-methanol: synthesis of naturally occurring 4-alkoxy-2-arylquinolines," *Tetrahedron Letters* 45:7903-7906, Sep. 11, 2004.
Lavoie et al., "Curcumin, Quercetin, and tBHQ Modulate Glutathione Levels in Astrocytes and Neurons: Importance of the Glutamate Cysteine Ligase Modifier Subunit," *J Neurochem.* 108:1410-1422, Mar. 2009, published online Jan. 22, 2009.
Prasad et al., "Synthesis and Antimicrobial Activity of Some Chalcone Derivatives," *E-Journal of Chemistry* 5(3):461-466, Jul. 2008.
Sato et al., "Convenient Synthesis of 1,6,7,8-Substituted 2-(3',4'-Substituted-phenyl)-4-quinolones via a 4-Ethoxyflavylium Salt," *Journal of Heterocyclic Chemistry* 36:1189-1193, Sep.-Oct. 1999, published Sep. 1999.
Wang et al., "Sulfuric acid promoted condensation cyclization of 2-(2-(trimethylsilyl)ethynyl)anilines with arylaldehydes in alcoholic solvents: an efficient one-pot synthesis of 4-alkoxy-2-arylquinolines," *Tetrahedron Letters* 50:2261-2265, Mar. 4, 2009.
Wang et al., "Interaction of Benzopyranone Derivatives and Related Compounds with Human Concentrative Nucleoside Transporters 1, 2 and 3 Heterologously Expressed in Porcine PK15 Nucleoside Transporter Deficient Cells. Structure-Activity Relationships and Determinants of Transporter Affinity and Selectivity," *Biochem. Pharmacol.* 79:307-320, 2010, published online Sep. 6, 2009.

* cited by examiner

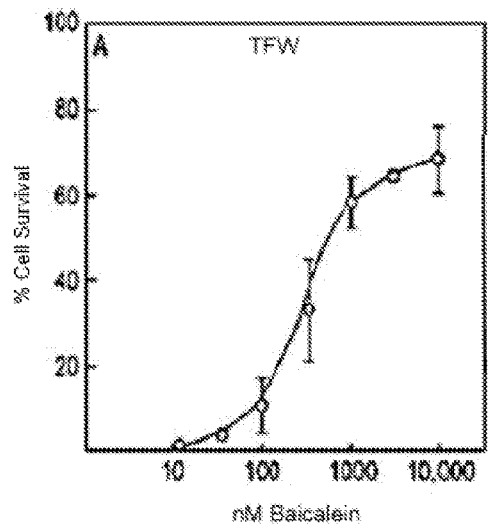
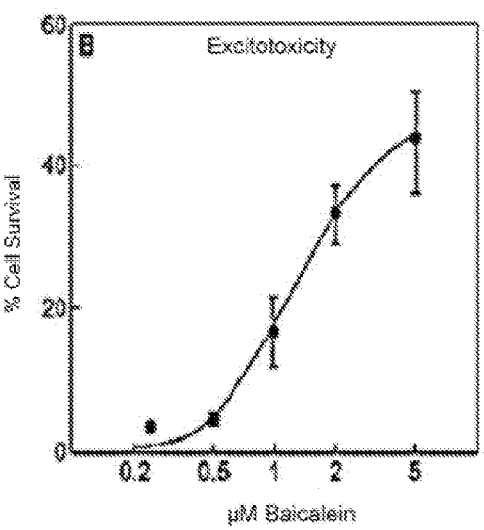
Fig. 5A    Fig. 5B
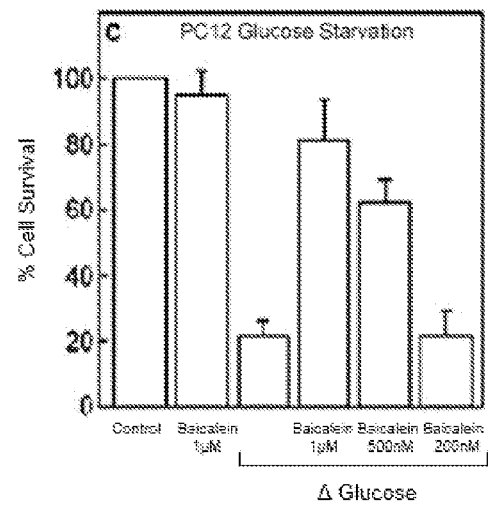
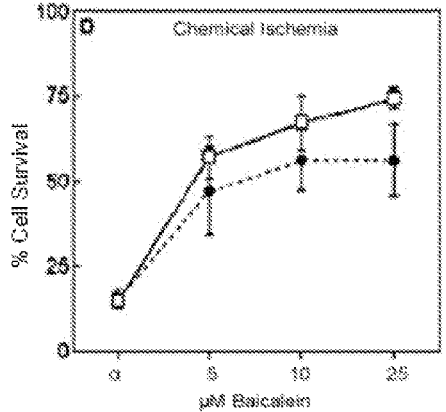
Fig. 5C    Fig. 5D

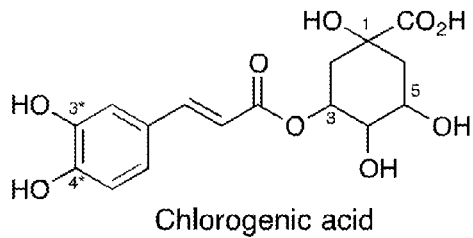
Chlorogenic acid
FIG. 9A
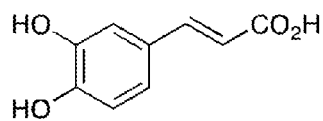
Caffeic Acid
FIG. 9B
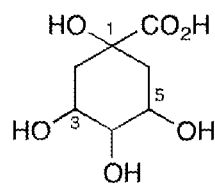
Quinic acid
FIG. 9C
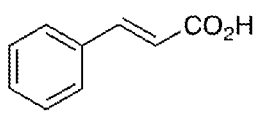
Cinnamic acid
FIG. 9D
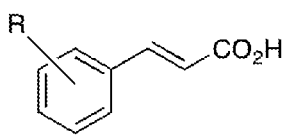
Substituted Cinnamic acid R = $CH_3$, OH, Halogen, $NO_2$, $NH_2$
FIG. 9E
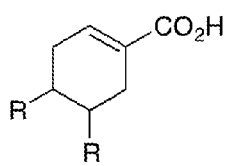 Cyclohexene carboxylic acids 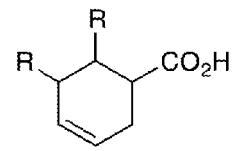
FIG. 9F  FIG. 9G
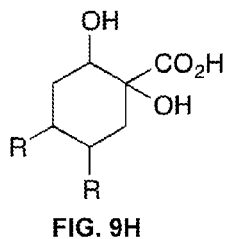 Cyclohexene carboxylic acid diols 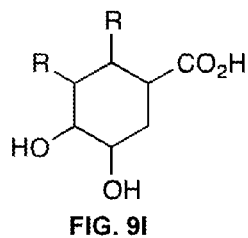
FIG. 9H  FIG. 9I
*Fig. 9*

Scheme 1. Synthesis of chalcone derivatives.

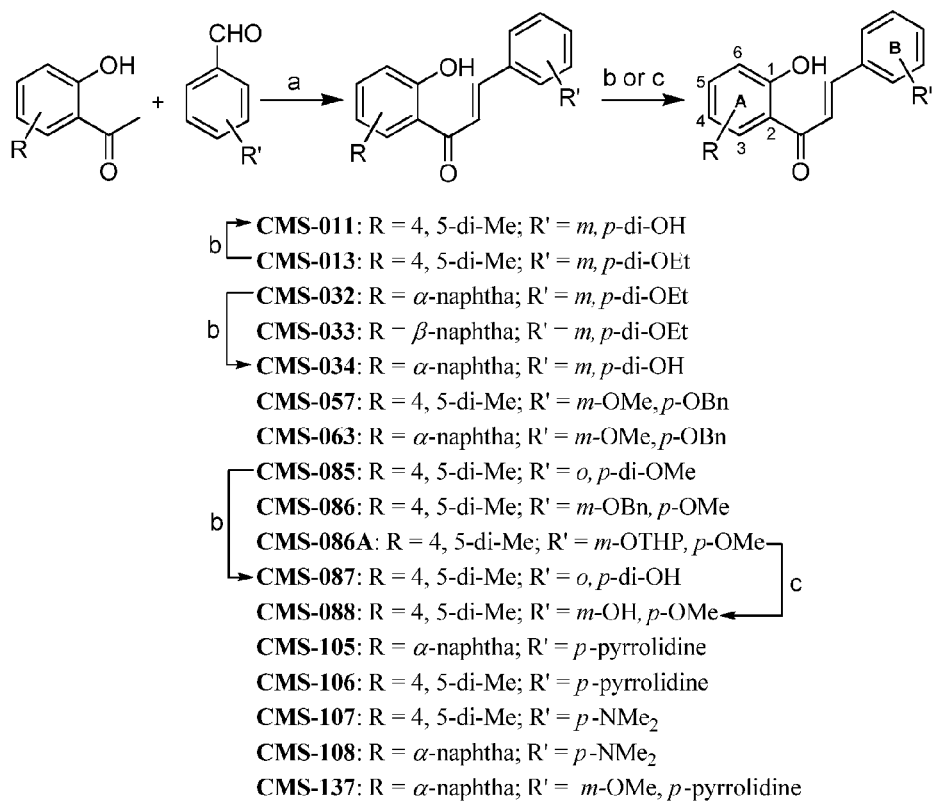

- CMS-011: R = 4, 5-di-Me; R' = *m, p*-di-OH
- CMS-013: R = 4, 5-di-Me; R' = *m, p*-di-OEt
- CMS-032: R = α-naphtha; R' = *m, p*-di-OEt
- CMS-033: R = β-naphtha; R' = *m, p*-di-OEt
- CMS-034: R = α-naphtha; R' = *m, p*-di-OH
- CMS-057: R = 4, 5-di-Me; R' = *m*-OMe, *p*-OBn
- CMS-063: R = α-naphtha; R' = *m*-OMe, *p*-OBn
- CMS-085: R = 4, 5-di-Me; R' = *o, p*-di-OMe
- CMS-086: R = 4, 5-di-Me; R' = *m*-OBn, *p*-OMe
- CMS-086A: R = 4, 5-di-Me; R' = *m*-OTHP, *p*-OMe
- CMS-087: R = 4, 5-di-Me; R' = *o, p*-di-OH
- CMS-088: R = 4, 5-di-Me; R' = *m*-OH, *p*-OMe
- CMS-105: R = α-naphtha; R' = *p*-pyrrolidine
- CMS-106: R = 4, 5-di-Me; R' = *p*-pyrrolidine
- CMS-107: R = 4, 5-di-Me; R' = *p*-NMe$_2$
- CMS-108: R = α-naphtha; R' = *p*-NMe$_2$
- CMS-137: R = α-naphtha; R' = *m*-OMe, *p*-pyrrolidine Reagents and conditions: a) Ba(OH)$_2$, MeOH, 40 °C, overnight, 30-90%
b) BBr$_3$, CH$_2$Cl$_2$, 0 °C-rt, overnight, 30-70%; c) *p*TSA, MeOH, rt, 94%

*Fig. 10*

Scheme 2. Synthesis of flavone derivatives.

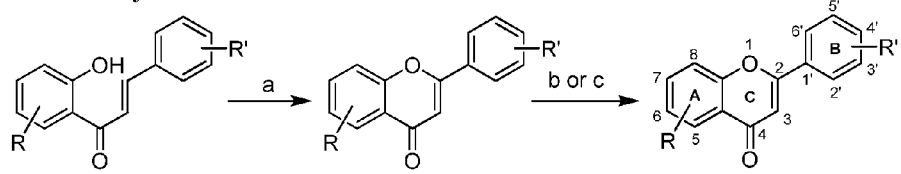

Chalcones:
CMS-013: R = 4, 5-di-Me; R' = m, p-di-OEt
CMS-032: R = α-naphtha; R' = m, p-di-OEt
CMS-057: R = 4, 5-di-Me; R' = m-OMe, p-OBn
CMS-063: R = α-naphtha; R' = m-OMe, p-OBn
CMS-085: R = 4, 5-di-Me; R' = o, p-di-OMe
CMS-105: R = α-naphtha; R' = p-pyrrolidine
CMS-106: R = 4, 5-di-Me; R' = p-pyrrolidine
CMS-107: R = 4, 5-di-Me; R' = p-NMe$_2$
CMS-108: R = α-naphtha; R' = p-NMe$_2$

Flavones:
CMS-02P: R = α-naphtha; R' = 3', 4'-di-OH
CMS-018: R = 6, 7-di-Me; R' = 3', 4'-di-OEt ⎤ b
CMS-028: R = 6, 7-di-Me; R' = 3', 4'-di-OH ⎦
CMS-038: R = α-naphtha; R' = 3', 4'-di-OEt
CMS-058: R = 6, 7-di-Me; R' = 3'-OMe, 4'-OBn ⎤ c
CMS-064: R = 6, 7-di-Me; R' = 3'-OMe, 4'-OH ⎦
CMS-068: R = α-naphtha; R' = 3'-OMe, 4'-OBn ⎤ c
CMS-072: R = α-naphtha; R' = 3'-OMe, 4'-OH ⎦
CMS-089: R = 6, 7-di-Me; R' = 2', 4'-di-OMe ⎤ b
CMS-094: R = 6, 7-di-Me; R' = 2', 4'-di-OH ⎦
CMS-115: R = α-naphtha; R' = 4'-pyrrolidine
CMS-116: R = 6, 7-di-Me; R' = 4'-pyrrolidine
CMS-119: R = 6, 7-di-Me; R' = 4'-NMe$_2$
CMS-120: R = α-naphtha; R' = 4'-NMe$_2$ Reagents and conditions: a) I$_2$, DMSO, 130 °C, 6 h, 50-95%; b) BBr$_3$, CH$_2$Cl$_2$, 0 °C-rt, overnight, 30-70%; c) H$_2$, Pd/C, 1:1, EtOAc/MeOH, overnight, 60%;

*Fig. 11*

Scheme 3. Synthesis of flavonol derivatives

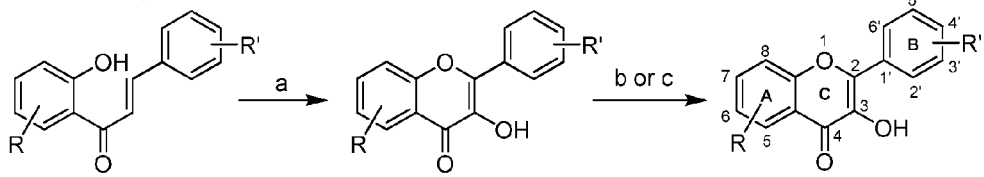

Chalcones:
CMS-013: R = 4, 5-di-Me; R' = m,p-di-OEt
CMS-032: R = α-naphtha; R' = m, p-di-OEt
CMS-033: R = β-naphtha; R' = m,p-di-OEt
CMS-057: R = 4, 5-di-Me; R' = m-OMe, p-OBn
CMS-063: R = α-naphtha; R' = m-OMe, p-OBn
CMS-085: R = 4, 5-di-Me; R' = o, p-di-OMe
CMS-086: R = 4, 5-di-Me; R' = m-OBn, p-OMe
CMS-105: R = α-naphtha; R' = p-pyrrolidine
CMS-106: R = 4, 5-di-Me; R' = p-pyrrolidine
CMS-107: R = 4, 5-di-Me; R' = p-NMe2
CMS-108: R = α-naphtha; R' = p-NMe2
CMS-137: R = α-naphtha;
    R' = m-OMe, p-pyrrolidine

Flavonols:
b ⎡ CMS-025: R = 6, 7-di-Me; R' = 3', 4'-di-OEt
  ⎣→CMS-027: R = 6, 7-di-Me; R' = 3', 4'-di-OH
    ⎡ CMS-036: R = α-naphtha; R' = 3', 4'-di-OEt
b ⎢ CMS-037: R = β-naphtha; R' = 3', 4'-di-OEt ⎤
  ⎣→CMS-040: R = α-naphtha; R' = 3', 4'-di-OH ⎥ b
    CMS-041: R = β-naphtha; R' = 3', 4'-di-OH ←⎦
    ⎡CMS-059: R = 6, 7-di-Me; R' = 3'-OMe, 4'-OBn
c ⎢ CMS-065: R = α-naphtha; R' = 3'-OMe, 4'-OBn ⎤
  ⎣→CMS-069: R = 6, 7-di-Me; R' = 3'-OMe,4'-OH ⎥ c
    CMS-070: R = α-naphtha; R' = 3'-OMe, 4'-OH ←⎦
    CMS-090: R = 6, 7-di-Me; R' = 2', 4'-di-OMe ⎤
   ⎡CMS-091: R = 6, 7-di-Me; R' = 3'-OBn, 4'-OMe ⎥
c ⎣→CMS-092: R = 6, 7-di-Me; R' = 3'-OH, 4'-OMe ⎥ b
    CMS-093: R = 6, 7-di-Me; R' = 2', 4'-di-OH ←⎦
    CMS-114: R = α-naphtha; R' = 4'-pyrrolidine
    CMS-117: R = 6, 7-di-Me; R' = 4'-NMe2
    CMS-118: R = α-naphtha; R' = 4'-NMe2
    CMS-122: R = 6, 7-di-Me; R' = 4'-pyrrolidine
   ⎡CMS-139: R = α-naphtha; R' = 3'-OMe, 4'-pyrrolidine
b ⎣→CMS-140: R = α-naphtha; R' = 3'-OH, 4'-pyrrolidine Reagents and conditions: a) 5.4% NaOH, 30% $H_2O_2$, MeOH, 0 °C- rt, overnight, 40-90%;
b) $BBr_3$, $CH_2Cl_2$, 0 °C-rt, overnight, 30-70%; c) $H_2$, Pd/C, 1:1, EtOAc/MeOH, overnight, 60%

*Fig. 12*

Scheme 4. Synthesis of quinoline derivatives.

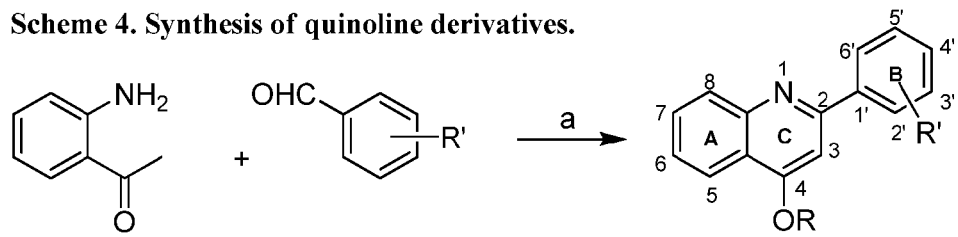

CMS-001: R = Me; R' = *m*-OH, *p*-OMe
CMS-004: R = Me; R' = *m,p*-di-OEt
CMS-007: R = Me; R' = *m,p*-di-OH
CMS-017: R = Me; R' = *m*-OMe, *p*-OH
CMS-021: R = Me; R' = H
CMS-022: R = Me; R' = *p*-OH
CMS-023: R = Et; R' = *m,p*-di-OH
CMS-024: R = *i*pr; R' = *m,p*-di-OH
CMS-083: R = Me; R' = *o,p*-di-OH
CMS-084: R = *i*pr; R' = *o,p*-di-OH
CMS-109: R = Me; R' = *p*-NMe$_2$
CMS-110: R = Me; R' = *p*-pyrrolidine
CMS-111: R = Me; R' = *m*-OH *p*-NO$_2$
CMS-112: R = *i*pr; R' = *p*-NMe$_2$
CMS-113: R = *i*pr; R' = *p*-pyrrolidine
CMS-121: R = cyclopentyl; R' = *m,p*-di-OH Reagents and conditions: a) ROH, H$_2$SO$_4$, reflux, overnight, 15-40%

Fig. 13

Synthesis of compounds PM-001, PM-002, PM-003 and PM-008

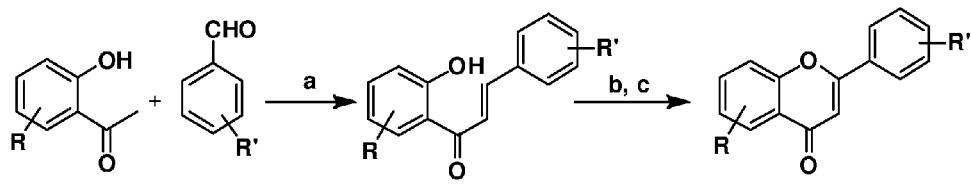

R = H; R' = 3', 4'-di-OEt --------------------------------- PM-001: R = H; R' = 3', 4'-di-OH
R = α-naphtha; R' = 3', 4'-di-OEt --------------------- PM-002: R = α-naphtha; R' = 3', 4'-di-OH
R = β-naphtha; R' = 3', 4'-di-OEt --------------------- PM-003: R = β-naphtha; R' = 3', 4'-di-OH
R = H; R' = 3', 4' 5'-tri-OMe -------------------------- PM-008 R = H; R' = 3', 4' 5'-tri-OH Reagents and conditions: a) general procedure A: Ba(OH)$_2$, MeOH, 40 $^0$C, overnight;

b) general procedure E: I$_2$, DMSO, 130 $^0$C, 6 h; c) general procedure B: BBr$_3$, CH$_2$Cl$_2$, 0 $^0$C-rt, overnight.

*Fig. 14*

Synthesis of compounds PM-004, PM-010, PM-012 and PM-013

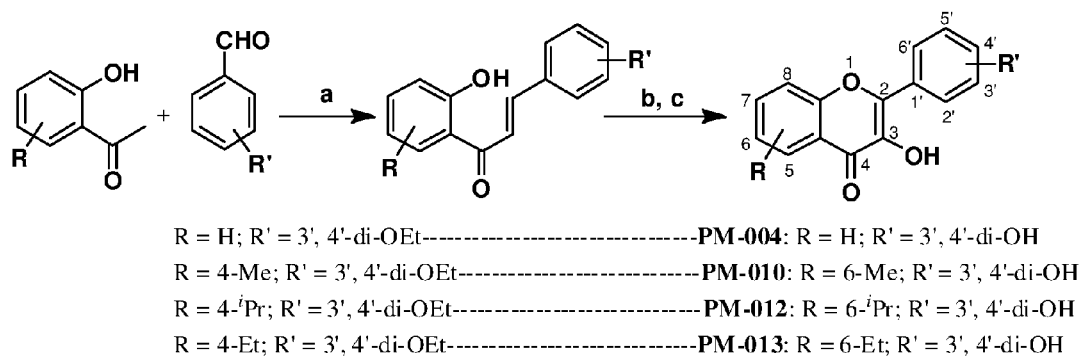

R = H; R' = 3', 4'-di-OEt ---------------------------- PM-004: R = H; R' = 3', 4'-di-OH
R = 4-Me; R' = 3', 4'-di-OEt ------------------------ PM-010: R = 6-Me; R' = 3', 4'-di-OH
R = 4-$^i$Pr; R' = 3', 4'-di-OEt --------------------- PM-012: R = 6-$^i$Pr; R' = 3', 4'-di-OH
R = 4-Et; R' = 3', 4'-di-OEt ------------------------- PM-013: R = 6-Et; R' = 3', 4'-di-OH

Reagents and conditions: a) general procedure A: Ba(OH)$_2$, MeOH, 40 °C, overnight;
b) general procedure F: 5.4% NaOH, 30% H$_2$O$_2$, MeOH, 0 °C- rt, overnight;
c) general procedure B: BBr$_3$, CH$_2$Cl$_2$, 0 °C-rt, overnight.

*Fig. 15*

Synthesis of Compounds CMS-129 and CMS-138

Reagents and conditions: a) general procedure A: Ba(OH)$_2$, MeOH, 40 °C, overnight, 30-90%
b) general procedure B: BBr$_3$, CH$_2$Cl$_2$, 0 °C-rt, overnight, 30-70%

NEUROPROTECTIVE POLYPHENOL ANALOGS

CROSS—REFERENCE TO RELATED APPLICATIONS

This is a divisional of U.S. patent application Ser. No. 14/173,658, filed Feb. 5, 2014, which is a continuation of International Application No. PCT/US2012/050324, filed Aug. 10, 2012, which was published in English under PCT Article 21(2), which in turn claims priority to U.S. Provisional Application No. 61/522,878, filed Aug. 12, 2011, all which are incorporated by reference herein in their entirety.

STATEMENT OF GOVERNMENTAL SUPPORT

This invention was made with government support under Grant No. 1U01NS060685, awarded by National Institute of Neurological Disorders and Stroke, National Institutes of Health. The government has certain rights in the invention.

FIELD

The present invention provides compounds having neuroprotective, neurotrophic, anti-inflammatory and/or antioxidant properties. The compounds are useful for promoting, enhancing and/or increasing the protection, growth and/or regeneration of neurons. The compounds also find use to increase, enhance and/or maintain intracellular glutathione (GSH) levels. The invention further relates to methods for the treatment, prevention, and mitigation of neurodegenerative conditions, and methods for the treatment, prevention, and mitigation of diabetes and Huntington's disease, comprising administering to a subject in need thereof an effective amount of a compound as disclosed and claimed herein.

BACKGROUND

There are currently no drugs available that prevent the nerve cell death associated with the majority of age-related disorders of the CNS. There are a number of reasons for this but probably the most important is that multiple factors contribute to the nerve cell death such that targeting a single pathway is unlikely to be successful. One example of this problem is ischemic stroke which is the leading cause of adult disability and the third leading cause of death in the US (Véronique, et al., *Circulation*. (2011) 123 (4), e18-e209). Worldwide, approximately 5 million people die each year of stroke and the mortality rates are estimated to double by the year 2020 (Donnan, et al., *The Lancet*. (2008), 371 (9624), 1612-1623). The nerve cell death associated with cerebral ischemia is due to multiple factors resulting from the lack of oxygen to support respiration and ATP synthesis, acidosis due to the buildup of the glycolytic product lactic acid, the loss of neurotrophic support, multiple metabolic stresses and inflammation (Lipton, *Physiol. Rev.* (1999) 79, 1431-1568; and Pandya, et al., *Cent. Nerv. Syst. Agents. Med. Chem.* (2011) Apr 27, PMID:21521165). While the focus of current drug discovery paradigms is on the development of high affinity, single target ligands, it is unlikely that a drug directed against a single molecular target will be effective in treating the nerve cell death associated with conditions such as stroke because of the multitude of insults that contribute to the cell's demise. This conclusion is supported by the failure of the single, high affinity target approach to drug development to identify treatments for stroke. Indeed, the only FDA-approved treatment to date is recombinant tissue-type plasminogen activator (rt-PA) (Green, et al., *Drug Discov. Today*. (2006) 11, 681-693), which is a vascular agent. An alternative approach is to identify small molecules that have multiple biological activities relevant to the maintenance of neurological function.

The flavonal Fisetin has been found to be an orally active, novel neuroprotective and cognition-enhancing molecule (Maher, *Genes. Nutr*. (2009), Sep 10, PMID:19756810). Fisetin not only has direct antioxidant activity but it can also increase the intracellular levels of glutathione, the major intracellular antioxidant, via the activation of transcription factors such as Nrf25. Fisetin can also maintain mitochondrial function in the presence of oxidative stress. In addition, it has anti-inflammatory activity against immune cells and inhibits the activity of 5-lipoxygenase, thereby reducing the production of lipid peroxides and their pro-inflammatory by-products (Maher, *Genes. Nutr.* (2009), supra). This wide range of actions suggests that Fisetin has the ability to reduce the loss of neurological function associated with multiple disorders, including stroke.

Although Fisetin has been shown to be effective in the rabbit small clot embolism model of stroke (Maher, et al., *Brain Research*. (2007) 1173, 117-125), its relatively high $EC_{50}$ in cell based assays (2-5 µM) and also low lipophilicity (CLogP 1.24), high tPSA (107 Å), more hydrogen bond donors (HBD=5) and poor bioavailability (Shia, et al., *J. Agric. Food Chem*. (2009) 57 (1), 83-89) suggest that there is room for medicinal chemical improvement if Fisetin is to be used therapeutically for treating neurological disorders such as stroke. However, given its ability to activate multiple target pathways related to neuroprotection, screening for improvements is significantly more complicated than with the current classical approach to the development of a single target drug. The present invention is based in part, on the use of a multi-tiered approach to screening that has facilitated the identification of Fisetin derivatives with significantly enhanced neuroprotective activity in an in vitro ischemia model while at the same time maintaining other key actions including anti-inflammatory and neurotrophic activity as well as the ability to maintain glutathione under conditions of oxidative stress.

SUMMARY

In various embodiments, the invention is directed to polyphenol compounds and analogs that can be used in treatment of patients afflicted with medical conditions such as diabetes, Huntington's disease, Parkinson's disease, Alzheimer's dementia, non-Alzheimer's dementia, multiple sclerosis, traumatic brain injury, spinal cord injury, and ALS, as well as for treatment of conditions involving ischemia, such as ischemic or embolic stroke, and their symptoms and sequelae. The compounds of the invention can be used to maintain glutathione levels in patients, and can provide neuroprotective effects In various embodiments, the compound of the invention is a compound of formula I:

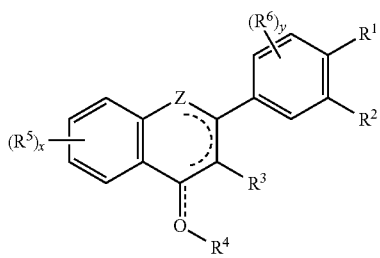

I or a pharmaceutically acceptable salt thereof, wherein:
Z is N or O, when Z is N then

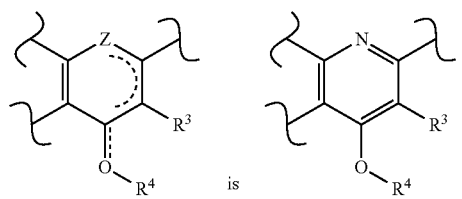

is when Z is O, then

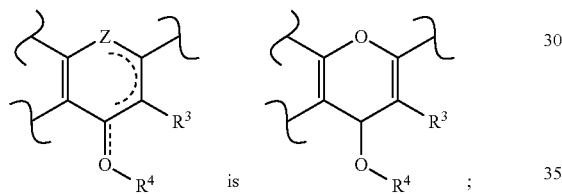

is

;

each of $R^1$ and $R^2$, independent of the other, is H, optionally substituted $C_{1-6}$alkyl, —$OR^a$, —$NO_2$ or —$N(R^c)_2$; when both $R^1$ and $R^2$ are —$OR^a$, then, optionally, they combine to form a 5-6 membered ring of formula

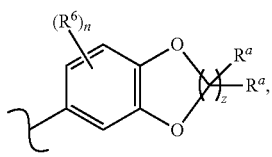

where z is 1 or 2;
$R^3$ is H, optionally substituted $C_{1-6}$alkyl or —$OR^a$;
$R^4$, when present, is $R^a$;
each of $R^5$ and $R^6$ is, independently for each occurrence, H, $R^e$, $R^b$, $R^e$ substituted with one or more of the same or different $R^a$ and/or $R^b$, —$OR^e$ substituted with one or more of the same or different $R^a$ and/or $R^b$, —$SR^e$ substituted with one or more of the same or different $R^a$ and/or $R^b$, —$C(O)R^e$ substituted with one or more of the same or different $R^a$ and/or $R^b$, —$N(R^a)R^e$ where $R^e$ is substituted with one or more of the same or different $R^a$ and/or $R^b$, —$(C(R^a)_2)_m$—$R^b$, —O—$(C(R^a)_2)_m$—$R^b$, —S—$(C(R^a)_2)_m$—$R^b$, —$(C(R^b)_2)_m$—$R^a$, —$N(R^a)$—$(C(R^a)_2)_m$—$R^b$, —O—$(CH_2)_m$—$CH((CH_2)_mR^b)R^b$, —C(O)N($R^a$)—$(C(R^a)_2)_m$—$R^b$, —O—$(C(R^a)_2)_m$—C(O)N($R^a$)—(C($R^a$)$_2$)$_m$—$R^b$, —N((C($R^a$)$_2$)$_m$$R^b$)$_2$, —S—(C($R^a$)$_2$)$_m$—C(O)N($R^a$)—(C($R^a$)$_2$)$_m$—$R^b$, —N($R^a$)—C(O)—N($R^a$)—(C($R^a$)$_2$)$_m$—$R^b$, —N($R^a$)—C(O)—(C($R^a$)$_2$)$_m$—C($R^a$)($R^b$)$_2$ or —N($R^a$)—(C($R^a$)$_2$)$_m$—C(O)—N($R^a$)—(C($R^a$)$_2$)$_m$—$R^b$;

each $R^a$ is independently for each occurrence H, $C_{1-6}$alkyl, $C_{3-8}$cycloalkyl, $C_{4-11}$cycloalkylalkyl, $C_{6-10}$aryl, $C_{7-16}$arylalkyl, 3-10 membered heteroalicyclyl, 4-11 membered heteroalicyclylalkyl, 5-15 membered heteroaryl or 6-16 membered heteroarylalkyl;

each $R^b$ is independently for each occurrence =O, =S, —$OR^a$, —O—$(C(R^a)_2)_m$—$OR^a$, —$SR^a$, =$NR^a$, =$NOR^a$, —$N(R^c)_2$, halo, —$CF_3$, —CN, —$NO_2$, —$S(O)R^a$, —$S(O)_2R^a$, —$SO_3R^a$, —$S(O)_2N(R^c)_2$, —C(O)$R^a$, —$CO_2R^a$, —C(O)N($R^c$)$_2$, —OC(O)N($R^c$)$_2$, —[N($R^a$)C(O)]$_n$$R^a$, —[N($R^a$)C(O)]$_n$$OR^a$ or —[N($R^a$)C(O)]$_n$N($R^c$)$_2$;

each $R^c$ is independently for each occurrence $R^a$, or, alternatively, two $R^c$ are taken together with the nitrogen atom to which they are bonded to form a 3 to 10-membered heteroalicyclyl or a 5-10 membered heteroaryl which may optionally include one or more of the same or different additional heteroatoms and which is optionally substituted with one or more of the same or different $R^a$ and/or $R^d$ groups;

each $R^d$ is =O, —$OR^a$, halo$C_{1-3}$alkyloxy, $C_{1-6}$alkyl, =S, —$SR^a$, —$N(R^a)_2$, halo, —$CF_3$, —CN, —$NO_2$, —$S(O)R^a$, —$S(O_2)R^a$, —$SO_3R^a$, —$S(O)_2N(R^a)_2$, —C(O)$R^a$, —$CO_2R^a$, —C(O)N($R^a$)$_2$, —OC(O)N($R^a$)$_2$, —[N($R^a$)C(O)]$_n$$R^a$, —(C($R^a$)$_2$)$_n$—$OR^a$, —C(O)—$C_{1-6}$haloalkyl, —OC(O)$R^a$, —O(C($R^a$)$_2$)$_m$—$OR^a$, —S(C($R^a$)$_2$)$_m$—$OR^a$, —N($R^a$)—(C($R^a$)$_2$)$_m$—$OR^a$, —[N($R^a$)C(O)]$_n$$OR^a$, —[N($R^a$)C(O)]$_n$N($R^a$)$_2$ or —N($R^a$)C(O)$C_{1-6}$haloalkyl; two $R^d$, taken together with the atom or atoms to which they are attached, combine to form a 3-10 membered partially or fully saturated mono or bicyclic ring, optionally containing one or more heteroatoms and optionally substituted with one or more $R^a$;

each $R^e$ is independently for each occurrence $C_{1-6}$alkyl, $C_{3-8}$cycloalkyl, $C_{4-11}$cycloalkylalkyl, $C_{6-10}$aryl, $C_{7-16}$arylalkyl, 3-10 membered heteroalicyclyl, 4-11 membered heteroalicyclylalkyl, 5-15 membered heteroaryl or 6-16 membered heteroarylalkyl;

two of $R^5$, and independently, two of $R^6$, together with the vicinal carbons to which they are attached, combine to form a 4-10 membered unsaturated, partially saturated or fully saturated mono or bicyclic ring, optionally containing one or more heteroatoms and optionally substituted with one or more $R^a$ and/or $R^b$;

each m is 1, 2 or 3;

each n is 0, 1, 2 or 3;

x is 0, 1, 2, 3 or 4; and y is 0, 1, 2 or 3, provided the compound is not Fisetin, Baicalein, PM-001, PM-002, PM-003, PM-004, PM-008 or PM-014.

In some embodiments, the compound can be of Formula IIA,

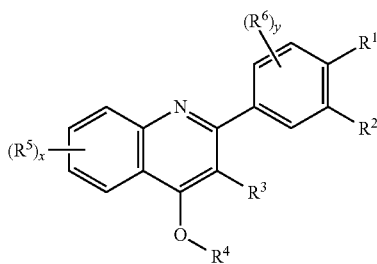

IIA wherein each of $R^1$ and $R^2$, independent of the other, is H, optionally substituted $C_{1-6}$alkyl, —$OR^a$ or —$N(R^c)_2$; $R^3$ is H, optionally substituted $C_{1-6}$alkyl or —$OR^a$; $R^4$ is $C_{1-6}$alkyl, $C_{3-8}$cycloalkyl, $C_{4-11}$cycloalkylalkyl, $C_{6-10}$aryl or $C_{7-16}$arylalkyl; and each of $R^5$ and $R^6$ is, independently for each occurrence H, $C_{1-6}$alkyl, $C_{3-8}$cycloalkyl, $C_{4-11}$cycloalkylalkyl, $C_{6-10}$aryl, $C_{7-16}$arylalkyl, —$OR^a$, —O—(C($R^a$)$_2$)$_m$—$OR^a$, —$SR^a$, —$N(R^c)_2$, halo, —$CF_3$, —$CO_2R^a$, —$C(O)N(R^c)_2$; and optionally, two of $R^5$, together with the vicinal carbons to which they are attached, combine to form a 6-membered unsaturated aryl ring, said 6-membered aryl ring optionally substituted with one or more $R^a$ and/or $R^b$.

In some embodiments, each of $R^1$ and $R^2$, independent of the other, is —$OR^a$; $R^3$ is H or optionally substituted $C_{1-6}$alkyl; and $R^4$ is $C_{1-6}$alkyl, $C_{3-8}$cycloalkyl, $C_{4-11}$cycloalkylalkyl, $C_{6-10}$aryl or $C_{7-16}$arylalkyl.

In some embodiments, one of $R^1$ and $R^2$ is optionally substituted $C_{1-6}$alkyl and the other of $R^1$ and $R^2$ is H, —$OR^a$ or —$N(R^c)_2$; $R^3$ is H or optionally substituted $C_{1-6}$alkyl; and $R^4$ is $C_{1-6}$alkyl, $C_{3-8}$cycloalkyl, $C_{4-11}$cycloalkylalkyl, $C_{6-10}$aryl or $C_{7-16}$arylalkyl.

In some embodiments, one of $R^1$ and $R^2$ is H or —$OR^a$ and the other of $R^1$ and $R^2$ is H or —$N(R^c)_2$, provided at least one of $R^1$ and $R^2$ is not H; $R^3$ is H or optionally substituted $C_{1-6}$alkyl; and $R^4$ is $C_{1-6}$alkyl, $C_{3-8}$cycloalkyl, $C_{4-11}$cycloalkylalkyl, $C_{6-10}$aryl or $C_{7-16}$arylalkyl.

In some embodiments, the compound can be of Formula IIB,

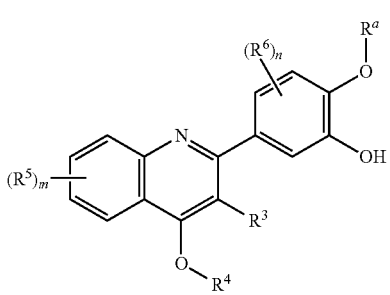

IIB wherein $R^a$ is H or $C_{1-6}$alkyl; $R^3$ is H or $C_{1-6}$alkyl; $R^4$ is $C_{1-6}$alkyl, $C_{3-8}$cycloalkyl, $C_{4-11}$cycloalkylalkyl, $C_{6-10}$aryl or $C_{7-16}$arylalkyl; each of $R^5$ and $R^6$ is, independently for each occurrence H, $C_{1-6}$alkyl, $C_{3-8}$cycloalkyl, $C_{4-11}$cycloalkylalkyl, —$OR^a$, —O—(C($R^a$)$_2$)$_m$—$OR^a$, —$SR^a$, —$N(R^c)_2$, halo, —$CF_3$, —$CO_2R^a$ or —$C(O)N(R^c)_2$; and each $R^c$ is independently for each occurrence $R^a$, or, alternatively, two $R^c$ are taken together with the nitrogen atom to which they are bonded to form a 3 to 7-membered heteroalicyclyl.

In some embodiments, $R^a$ is H or $C^{1-6}$alkyl; $R^3$ is H or $C_{1-6}$alkyl; $R^4$ is $C_{1-6}$alkyl, $C_{3-8}$cycloalkyl or $C_{4-11}$cycloalkylalkyl; and each of $R^5$ and $R^6$ is, independently for each occurrence H, $C_{1-6}$alkyl, $C_{3-8}$cycloalkyl, $C_{4-11}$cycloalkylalkyl, —$OR^a$, —$N(R^c)_2$, halo, —$CF_3$, —$CO_2R^a$ or —$C(O)N(R^c)_2$.

In some embodiments, the compound can be of Formula IIIA,

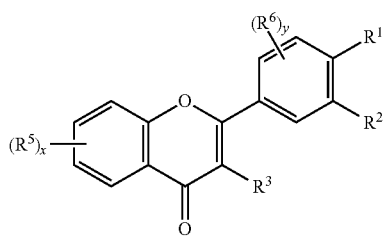

IIIA wherein each of $R^1$ and $R^2$, independent of the other, is H, optionally substituted $C_{1-6}$alkyl, —$OR^a$ or —$N(R^c)_2$; $R^3$ is H, optionally substituted $C_{1-6}$alkyl or —$OR^a$; and each of $R^5$ and $R^6$ is, independently for each occurrence H, $C_{1-6}$alkyl, $C_{3-8}$cycloalkyl, $C_{4-11}$cycloalkylalkyl, $C_{6-10}$aryl, $C_{7-16}$arylalkyl, —$OR^a$, —O—(C($R^a$)$_2$)$_m$—$OR^a$, —$SR^a$, —$N(R^c)_2$, halo, —$CF_3$, —$CO_2R^a$, —$C(O)N(R^c)_2$; and optionally, two of $R^5$, together with the vicinal carbons to which they are attached, combine to form a 6-membered unsaturated aryl ring, said 6-membered aryl ring optionally substituted with one or more $R^a$ and/or $R^b$.

In some embodiments, each of $R^1$ and $R^2$, independent of the other, is —$OR^a$; and $R^3$ is H, $C_{1-6}$alkyl or —$OR^a$.

In some embodiments, one of $R^1$ and $R^2$ is optionally substituted $C_{1-6}$alkyl and the other of $R^1$ and $R^2$ is H, —$OR^a$ or —$N(R^c)_2$; and $R^3$ is H, $C_{1-6}$alkyl or —$OR^a$.

In some embodiments, one of $R^1$ and $R^2$ is H or —$OR^a$ and the other of $R^1$ and $R^2$ is H or —$N(R^c)_2$, provided at least one of $R^1$ and $R^2$ is not H; and $R^3$ is H, $C_{1-6}$alkyl or —$OR^a$.

In some embodiments, the compound can be of Formula IIIB,

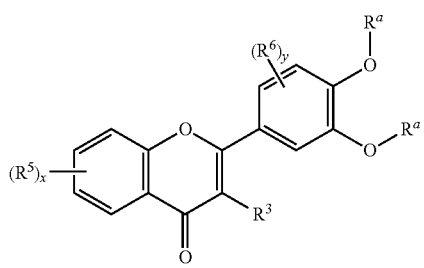

IIIB wherein each $R^a$ is H or $C_{1-6}$alkyl; $R^3$ is H, —OH, —$OC_{1-6}$alkyl or $C_{1-6}$alkyl; each of $R^5$ and $R^6$ is, independently for each occurrence H, $C_{1-6}$alkyl, $C_{3-8}$cycloalkyl, $C_{4-11}$cycloalkylalkyl, —$OR^a$, —O—(C($R^a$)$_2$)$_m$—$OR^a$, —$SR^a$, —$N(R^c)_2$, halo, —$CF_3$, —$CO_2R^a$ or —$C(O)N(R^c)_2$; and each $R^c$ is independently for each occurrence $R^a$, or, alternatively, two $R^c$ are taken together with the nitrogen atom to which they are bonded to form a 3 to 7-membered heteroalicyclyl, and optionally, two of $R^5$, together with the vicinal carbons to which they are attached, combine to form a 6-membered unsaturated aryl ring, said 6-membered aryl ring optionally substituted with one or more $R^a$ and/or $R^b$.

In some embodiments, the compound can be of Formula IIIC or IIID,

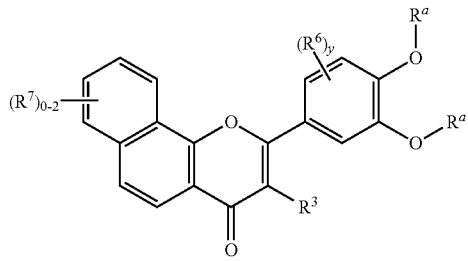

IIIC

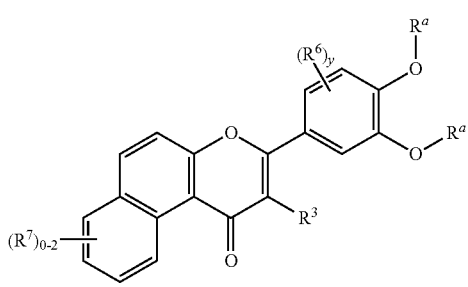

IIID wherein each $R^a$ is H or $C_{1-6}$alkyl; $R^3$ is H, —OH, —OC$_{1-6}$alkyl or $C_{1-6}$alkyl; each of $R^6$ is, independently for each occurrence H, $C_{1-6}$alkyl, —OR$^a$, —SR$^a$, —N(R$^c$)$_2$, or halo; and each $R^c$ is independently for each occurrence $R^a$, or, alternatively, two $R^c$ are taken together with the nitrogen atom to which they are bonded to form a 3 to 7-membered heteroalicyclyl; and $R^7$ is independently for each occurrence H, $C_{1-6}$alkyl, —OR$^a$, —SR$^a$, —N(R$^c$)$_2$, or halo.

In some embodiments, $R^3$ is H, —OH or $C_{1-6}$alkyl; and each of $R^5$ and $R^6$ is, independently for each occurrence H, $C_{1-6}$alkyl, $C_{3-8}$cycloalkyl, $C_{4-11}$cycloalkylalkyl, —OR$^a$, —N(R$^c$)$_2$, halo, —CF$_3$, —CO$_2$R$^a$ or —C(O)N(R$^c$)$_2$.

In some embodiments, the compound can be of Formula IIIE,

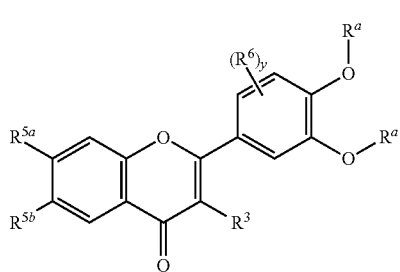

IIIE wherein each of $R^{5a}$ and $R^{5b}$ is independently H or $C_{1-6}$alkyl.

In some embodiments, each $R^a$ is independently H or $C_{1-6}$alkyl, and $R^6$ is, independently for each occurrence H, $C_{1-6}$alkyl, —OH, —OC$_{1-6}$alkyl, —N(R$^c$)$_2$, halo or —CF$_3$.

In some embodiments, one of $R^a$ is H and the other $R^a$ is $C_{1-6}$alkyl.

In some embodiments, both of $R^a$ are H.

In some embodiments, both of $R^a$ are $C_{1-6}$alkyl.

In some embodiments, y is 0, 1 or 2.

In some embodiments, y is 0 or 1.

In some embodiments, the compound can be of Formula IIIF,

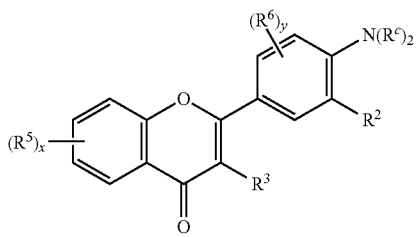

IIIF wherein $R^2$ is H or —OR$^a$; and $R^3$ is H, $C_{1-6}$alkyl or —OR$^a$.

In some embodiments, the compound is according to Formula IIIG,

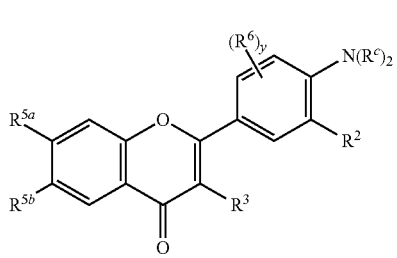

IIIG wherein each of $R^{5a}$ and $R^{5b}$ is independently H or $C_{1-6}$alkyl; and each $R^c$ is independently for each occurrence $R^a$, or, alternatively, two $R^c$ are taken together with the nitrogen atom to which they are bonded to form an optionally substituted 3- to 7-membered heteroalicyclyl.

In some embodiments, $R^6$ is, independently for each occurrence H, $C_{1-6}$alkyl, —OH, —OC$_{1-6}$alkyl, halo or —CF$_3$.

In some embodiments, y is 0, 1 or 2.

In some embodiments, —N(R$^c$)$_2$ is dimethylamino, diethylamino, ethylmethylamino, azirindin-1-yl, azetidin-1-yl, pyrrolidin-1-yl, piperidin-1-yl or 4-C$_{1-6}$alkyl substituted piperazin-1-yl.

In some embodiments, the compound can be of Formula IIIH or IIIJ,

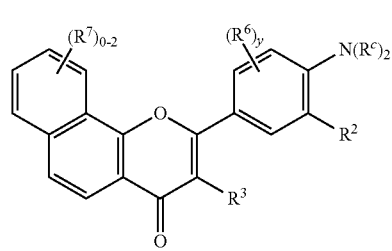

IIIH

-continued

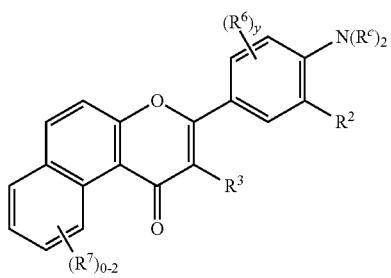

IIIJ wherein R³ is H, —OH, —OC₁₋₆alkyl or C₁₋₆alkyl; each of R⁶ is, independently for each occurrence H, C₁₋₆alkyl, —OR$^a$, —SR$^a$ or halo; and each R$^c$ is independently for each occurrence R$^a$, or, alternatively, two R$^c$ are taken together with the nitrogen atom to which they are bonded to form an optionally substituted 3- to 7-membered heteroalicyclyl; and R⁷ is independently for each occurrence H, C₁₋₆alkyl, —OR$^a$, —SR$^a$, —N(R$^c$)₂, or halo.

In some embodiments, R⁶ is, independently for each occurrence H, C₁₋₆alkyl, —OH, —OC₁₋₆alkyl, halo or —CF₃.

In some embodiments, y is 0, 1 or 2.

In some embodiments, —N(R$^c$)₂ is dimethylamino, diethylamino, ethylmethylamino, azirindin-1-yl, azetidin-1-yl, pyrrolidin-1-yl, piperidin-1-yl or 4-C₁₋₆alkyl substituted piperazin-1-yl.

In various embodiments, the compound can be of Formula IVA,

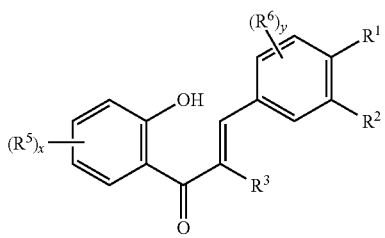

IVA wherein each of R¹ and R², independent of the other, is H, optionally substituted C₁₋₆alkyl, —OR$^a$ or —N(R$^c$)₂; R³ is H, optionally substituted C₁₋₆alkyl or —OR$^a$; and each of R⁵ and R⁶ is, independently for each occurrence H, C₁₋₆alkyl, C₃₋₈cycloalkyl, C₄₋₁₁cycloalkylalkyl, C₆₋₁₀aryl, C₇₋₁₆arylalkyl, —OR$^a$, —O—(C(R$^a$)₂)$_m$—OR$^a$, —SR$^a$, —N(R$^c$)₂, halo, —CF₃, —CO₂R$^a$, —C(O)N(R$^c$)₂; and optionally, two of R⁵, together with the vicinal carbons to which they are attached, combine to form a 6-membered unsaturated aryl ring, said 6-membered aryl ring optionally substituted with one or more R$^a$ and/or R$^b$, provided the compound is not chlorogenic acid.

In some embodiments, each of R¹ and R², independent of the other, is —OR$^a$; and R³ is H, C₁₋₆alkyl or —OR$^a$.

In some embodiments, one of R¹ and R² is optionally substituted C₁₋₆alkyl and the other of R¹ and R² is H, —OR$^a$ or —N(R$^c$)₂; and R³ is H, C₁₋₆alkyl or —OR$^a$.

In some embodiments, one of R¹ and R² is H or —OR$^a$ and the other of R¹ and R² is H or —N(R$^c$)₂, provided at least one of R¹ and R² is not H; and R³ is H, C₁₋₆alkyl or —OR$^a$.

In some embodiments, the compound can be of Formula IVB,

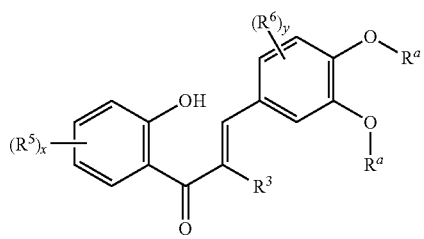

IVB wherein each R$^a$ is H or C₁₋₆alkyl; R³ is H, —OH, —OC₁₋₆alkyl or C₁₋₆alkyl; each of R⁵ and R⁶ is, independently for each occurrence H, C₁₋₆alkyl, C₃₋₈cycloalkyl, C₄₋₁₁cycloalkylalkyl, —OR$^a$, —O—(C(R$^a$)₂)$_m$—OR$^a$, —SR$^a$, —N(R$^c$)₂, halo, —CF₃, —CO₂R$^a$ or —C(O)N(R$^c$)₂; and each R$^c$ is independently for each occurrence R$^a$, or, alternatively, two R$^c$ are taken together with the nitrogen atom to which they are bonded to form a 3 to 7-membered heteroalicyclyl, and optionally, two of R⁵, together with the vicinal carbons to which they are attached, combine to form a 6-membered unsaturated aryl ring, said 6-membered aryl ring optionally substituted with one or more R$^a$ and/or R$^b$.

In some embodiments, the compound can be of Formula IVC or IVD,

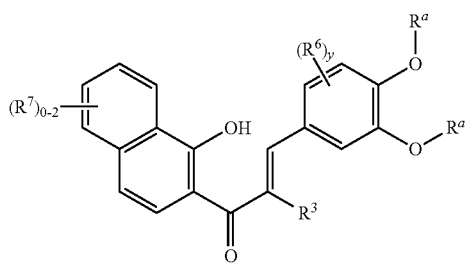

IVC

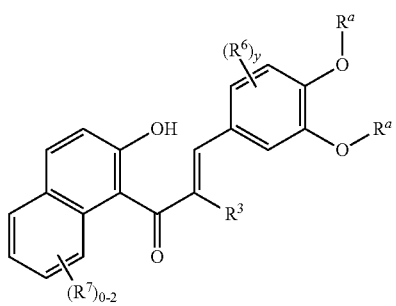

IVD wherein each R$^a$ is H or C₁₋₆alkyl; R³ is H, —OH, —OC₁₋₆alkyl or C₁₋₆alkyl; each of R⁶ is, independently for each occurrence H, C₁₋₆alkyl, —OR$^a$, —SR$^a$, —N(R$^c$)₂, or halo; and each R$^c$ is independently for each occurrence R$^a$, or, alternatively, two R$^c$ are taken together with the nitrogen atom to which they are bonded to form a 3 to 7-membered heteroalicyclyl; and R⁷ is independently for each occurrence H, C₁₋₆alkyl, —OR$^a$, —SR$^a$, —N(R$^c$)₂, or halo.

In some embodiments, R³ is H, —OH or C¹⁻⁶alkyl; and each of R⁵ and R⁶ is, independently for each occurrence H, C₁₋₆alkyl, C₃₋₈cycloalkyl, C₄₋₁₁cycloalkylalkyl, —OR$^a$, —N(R$^c$)₂, halo, —CF₃, —CO₂R$^a$ or —C(O)N(R$^c$)₂.

In some embodiments, the compound can be of Formula IVE,

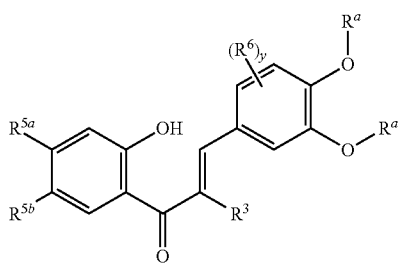

IVE wherein each of $R^{5a}$ and $R^{5b}$ is independently H or $C_{1-6}$alkyl.

In some embodiments, each $R^a$ is independently H or $C_{1-6}$alkyl, and $R^6$ is, independently for each occurrence H, $C_{1-6}$alkyl, —OH, —OC$_{1-6}$alkyl, —N(R$^c$)$_2$, halo or —CF$_3$.

In some embodiments, one of $R^a$ is H and the other $R^a$ is $C_{1-6}$alkyl.

In some embodiments, both of $R^a$ are H.

In some embodiments, both of $R^a$ are $C_{1-6}$alkyl.

In some embodiments, y is 0, 1 or 2.

In some embodiments, y is 0 or 1.

In some embodiments, the compound can be of Formula IVF,

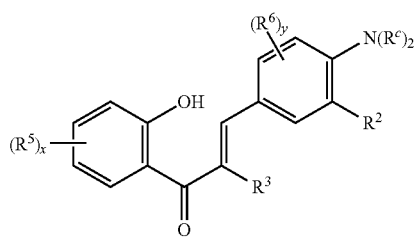

IVF wherein $R^2$ is H or —OR$^a$; and $R^3$ is H, $C_{1-6}$alkyl or —OR$^a$.

In some embodiments, the compound is according to Formula IVG,

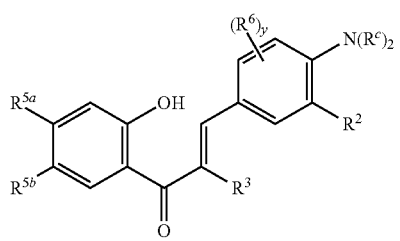

IVG wherein each of $R^{5a}$ and $R^{5b}$ is independently H or $C_{1-6}$alkyl; and each R$^c$ is independently for each occurrence R$^a$, or, alternatively, two R$^c$ are taken together with the nitrogen atom to which they are bonded to form an optionally substituted 3- to 7-membered heteroalicyclyl.

In some embodiments, $R^6$ is, independently for each occurrence H, $C_{1-6}$alkyl, —OH, —OC$_{1-6}$alkyl, halo or —CF$_3$.

In some embodiments, y is 0, 1 or 2.

In some embodiments, —N(R$^c$)$_2$ is dimethylamino, diethylamino, ethylmethylamino, azirindin-1-yl, azetidin-1-yl, pyrrolidin-1-yl, piperidin-1-yl or 4-$C_{1-6}$alkyl substituted piperazin-1-yl.

In some embodiments, the compound is according to Formula IVH or IVJ,

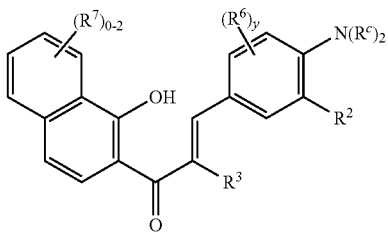

IVH

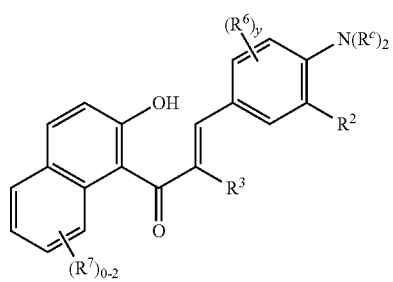

IVJ wherein $R^3$ is H, —OH, —OC$_{1-6}$alkyl or $C_{1-6}$alkyl; each of $R^6$ is, independently for each occurrence H, $C_{1-6}$alkyl, —OR$^a$, —SR$^a$ or halo; and each R$^c$ is independently for each occurrence R$^a$, or, alternatively, two R$^c$ are taken together with the nitrogen atom to which they are bonded to form an optionally substituted 3- to 7-membered heteroalicyclyl; and $R^7$ is independently for each occurrence H, $C_{1-6}$alkyl, —OR$^a$, —SR$^a$, —N(R$^c$)$_2$, or halo.

In some embodiments, $R^6$ is, independently for each occurrence H, $C_{1-6}$alkyl, —OH, —OC$_{1-6}$alkyl, halo or —CF$_3$.

In some embodiments, y is 0, 1 or 2.

In some embodiments, —N(R$^c$)$_2$ is dimethylamino, diethylamino, ethylmethylamino, azirindin-1-yl, azetidin-1-yl, pyrrolidin-1-yl, piperidin-1-yl or 4-$C_{1-6}$alkyl substituted piperazin-1-yl.

In some embodiments, the compound is:
4-methoxy-2-(3,4-dihydroxyphenyl)quinoline (CMS-007);
4-ethoxy-2-(3,4-dihydroxyphenyl)quinoline (CMS-023);
4-isopropoxy-2-(3,4-dihydroxyphenyl)quinoline (CMS-024);
4-isopropoxy-2-(2,4-dihydroxyphenyl)quinoline (CMS-084);
4-cyclopentyloxy-2-(3,4-dihydroxyphenyl)quinoline (CMS-121);
4-methoxy-2-(3-hydroxy, 4-methoxyphenyl)quinoline (CMS-001);
4-methoxy-2-(3,4-diethoxyphenyl)quinoline (CMS-004);
4-methoxy-2-(4-hydroxy, 3-methoxyphenyl)quinoline (CMS-017);
4-methoxy-2-phenylquinoline (CMS-021);
4-methoxy-2-(4-hydroxyphenyl)quinoline (CMS-022);
4-methoxy-2-(2,4-dihydroxyphenyl)quinoline (CMS-083);
4-methoxy-2-(4-dimethylaminophenyl)quinoline (CMS-109);

4-methoxy-2-(4-(pyrrolidin-1-yl)phenyl)quinoline (CMS-110);
4-methoxy-2-(3-hydroxy-4-nitrophenyl)quinoline (CMS-111);
4-isopropoxy-2-(4-dimethylaminophenyl)quinoline (CMS-112); or
4-isopropoxy-2-(4-(pyrrolidin-1-yl)phenyl)quinoline (CMS-113).

In some embodiments, the compound is:
2-(3,4-dihydroxyphenyl)-3-hydroxy-6-methyl-4H-chromen-4-one (PM-010);
2-(3,4-dihydroxyphenyl)-6-ethyl-3-hydroxy-4H-chromen-4-one (PM-013);
2-(3,4-dihydroxyphenyl)-3-hydroxy-6-propyl-4H-chromen-4-one (PM-012);
2-(3,4-dihydroxyphenyl)-3-hydroxy-4H-benzo[h]chromen-4-one (CMS-040);
3-hydroxy-2-(4-hydroxy-3-methoxyphenyl)-6,7-dimethyl-4H-chromen-4-one (CMS-069);
2-(4-(benzyloxy)-3-methoxyphenyl)-3-hydroxy-4H-benzo[h]chromen-4-one (CMS-065);
2-(4-hydroxy-3-methoxyphenyl)-3-methyl-4H-benzo[h]chromen-4-one (CMS-072);
2-(4-(benzyloxy)-3-methoxyphenyl)-3-hydroxy-6,7-dimethyl-4H-chromen-4-one (CMS-059);
2-(4-hydroxy-3-methoxyphenyl)-6,7-dimethyl-4H-chromen-4-one (CMS-064);
2-(4-(chloromethyl)-3-methoxyphenyl)-3-hydroxy-6,7-dimethyl-4H-chromen-4-one (CMS-078);
3-hydroxy-2-(3-hydroxy-4-methoxyphenyl)-6,7-dimethyl-4H-chromen-4-one (CMS-092);
2-(4-(dimethylamino)phenyl)-3-hydroxy-6,7-dimethyl-4H-chromen-4-one (CMS-117);
3-hydroxy-2-(4-(pyrrolidin-1-yl)phenyl)-4H-benzo[h]chromen-4-one (CMS-114);
2-(4-(dimethylamino)phenyl)-3-hydroxy-4H-benzo[h]chromen-4-one (CMS-118);
3-hydroxy-2-(3-methoxy-4-(pyrrolidin-1-yl)phenyl)-4H-benzo[h]chromen-4-one (CMS-139);
3-hydroxy-2-(3-hydroxy-4-(pyrrolidin-1-yl)phenyl)-4H-benzo[h]chromen-4-one (CMS-140);
2-(3,4-diethoxyphenyl)-6,7-dimethyl-4H-chromen-4-one (CMS-018);
2-(3,4-diethoxyphenyl)-3-hydroxy-6,7-dimethyl-4H-chromen-4-one (CMS-025);
2-(3,4-dihydroxyphenyl)-3-hydroxy-6,7-dimethyl-4H-chromen-4-one (CMS-027);
2-(3,4-dihydroxyphenyl)-6,7-dimethyl-4H-chromen-4-one (CMS-028);
2-(3,4-diethoxyphenyl)-3-hydroxy-4H-benzo[h]chromen-4-one (CMS-036);
2-(3,4-diethoxyphenyl)-4H-benzo[h]chromen-4-one (CMS-038);
3-(3,4-dihydroxyphenyl)-2-hydroxy-1H-benzo[f]chromen-1-one (CMS-041);
2-(4-(benzyloxy)-3-methoxyphenyl)-6,7-dimethyl-4H-chromen-4-one (CMS-058);
2-(2,4-dihydroxyphenyl)-3-hydroxy-6,7-dimethyl-4H-chromen-4-one (CMS-093);
2-(2,4-dihydroxyphenyl)-6,7-dimethyl-4H-chromen-4-one (CMS-094);
3-hydroxy-2-(4-hydroxy-3-methoxyphenyl)-4H-benzo[h]chromen-4-one (CMS-070);
2-(4-(pyrrolidin-1-yephenyl)-4H-benzo[h]chromen-4-one (CMS-115);
6,7-dimethyl-2-(4-(pyrrolidin-1-yl)phenyl)-4H-chromen-4-one (CMS-116);
2-(4-(dimethylamino)phenyl)-6,7-dimethyl-4H-chromen-4-one (CMS-119);
2-(4-(dimethylamino)phenyl)-4H-benzo[h]chromen-4-one (CMS-120); or
3-hydroxy-6,7-dimethyl-2-(4-(pyrrolidin-1-yl)phenyl)-4H-chromen-4-one (CMS-122).

In some embodiments, the compound is:
(E)-3-(3,4-dihydroxyphenyl)-1-(2-hydroxy-4,5-dimethylphenyl)prop-2-en-1-one (CMS-011);
(E)-3-(3,4-dihydroxyphenyl)-1-(1-hydroxynaphthalen-2-yl)prop-2-en-1-one (CMS-034);
(E)-3-(3-hydroxy-4-(pyrrolidin-1-yl)phenyl)-1-(1-hydroxynaphthalen-2-yl)prop-2-en-1-one (CMS-138);
(E)-1-(1-hydroxynaphthalen-2-yl)-3-(3-methoxy-4-(pyrrolidin-1-yl)phenyl)prop-2-en-1-one (CMS-137);
(E)-3-(3,4-dihydroxyphenyl)-1-(2-hydroxy-5-isopropylphenyl)prop-2-en-1-one (CMS-129);
(E)-3-(3,4-diethoxyphenyl)-1-(2-hydroxy-4,5-dimethylphenyl)prop-2-en-1-one (CMS-013);
(E)-3-(3,4-diethoxyphenyl)-1-(1-hydroxynaphthalen-2-yl)prop-2-en-1-one (CMS-032);
(E)-3-(4-(benzyloxy)-3-methoxyphenyl)-1-(1-hydroxynaphthalen-2-yl)prop-2-en-1-one (CMS-063);
(E)-3-(3-(benzyloxy)-4-methoxyphenyl)-1-(2-hydroxy-4,5-dimethylphenyl)prop-2-en-1-one (CMS-086);
(E)-3-(2,4-dihydroxyphenyl)-1-(2-hydroxy-4,5-dimethylphenyl)prop-2-en-1-one (CMS-087); or
(E)-1-(2-hydroxy-4,5-dimethylphenyl)-3-(3-hydroxy-4-methoxyphenyl)prop-2-en-1-one (CMS-088).

In a related aspect, the invention provides methods of treatment comprising administration of effective amounts of pharmaceutical compositions comprising one or more compounds, as described herein, and a pharmaceutically acceptable carrier, excipient or vehicle.

In a further aspect, the invention provides methods of treating, reducing, mitigating or preventing one or more symptoms of ischemia in a subject in need thereof comprising administering to the subject an effective amount of one or more compounds, as described herein, or a pharmaceutical composition comprising one or more of the compounds, as described herein.

The invention is directed, in various embodiments, to methods of treatment comprising administering an effective amount of a compound as described below for treatment of ischemia. The invention can provide methods of treating, reducing, mitigating or preventing ischemia or one or more sequelae or symptoms thereof in a patient or subject in need thereof, comprising administering to the subject an effective amount of one or more compounds as disclosed herein. For example, the patient can be a human, or the subject can be another mammal.

In various embodiments, the invention is directed to methods of treatment comprising administering an effective amount of a compound as described below for treatment of (1) ischemic stroke, (2) hemorrhagic stroke, (3) cardiovascular disease (e.g., ischemic heart conditions, patients undergoing heart bypass surgery or heart valve replacement), (4) ischemia related spinal cord injury, (5) ischemia in diabetic patients, and (6) embolic stroke; or any symptoms or sequelae thereof. The compound can also be used for treatment of patients at risk for any of the above-listed conditions.

In some embodiments, the subject has experienced an embolic stroke. In some embodiments, the subject is at risk of experiencing an embolic stroke. In some embodiments, the one or more polyphenol compounds, as described herein, or a pharmaceutical composition comprising one or more of the polyphenol compounds, as described herein, are co-administered with a thrombolytic agent. In various embodiments, the thrombolytic agent can be co-administered in a subtherapeutic dose or amount. For example, the thrombolytic agent can comprise tissue plasminogen activator, tenecteplase, urokinase, desmoteplase, reteplase, alteplase, anistreplase, streptokinase, or combinations thereof.

In various embodiments, the invention provides a method of treating diabetes, Parkinson's disease, Huntington's disease, Alzheimer's disease, non-Alzheimer's dementias, multiple sclerosis, traumatic brain injury, or ALS, comprising administering an effective amount of a compound of the invention as disclosed and claimed herein to a patient in need thereof. In various embodiments, the patient is experiencing or is at risk of experiencing sepsis, trauma and/or shock. For example, the patient can be a human, or can be another mammal.

In other embodiments, the invention provides methods of promoting, increasing, and/or enhancing the protection, growth and/or regeneration of neurons in a subject in need thereof, comprising administering to the subject an effective amount of one or more compounds, as described herein, or a pharmaceutical composition comprising one or more of the compounds, as described herein.

In another aspect, the invention provides methods of promoting, increasing, and/or enhancing the protection, growth and/or regeneration of neurons by maintaining or increasing glutathione (GSH) levels in a subject in need thereof, comprising administering to the subject an effective amount of one or more compounds, as described herein, or a pharmaceutical composition comprising one or more of the compounds, as described herein.

In some embodiments, the one or more compounds are or the pharmaceutical composition is administered over a period of one to three weeks. In some embodiments, the one or more compounds are or the pharmaceutical composition is administered for the remainder of the life of the subject. In some embodiments, the one or more compounds are or the pharmaceutical composition is administered until an efficacious effect is achieved.

In some embodiments, the compounds are or the pharmaceutical composition is administered orally, intravenously, inhalationally, transdermally or subcutaneously.

In some embodiments, the compound is co-administered with tissue plasminogen activator (tPA). For example, the tPA can be co-administered in a subtherapeutic dose or amount.

BRIEF DESCRIPTION OF THE DRAWINGS

FIG. 5A—trophic factor withdrawal. Primary cortical neurons are prepared from 18-day-old rat embryos, and cultured at low cell density 1×10⁶/35 mm dish, in serum containing medium with Baicalein (10-10,000 nM), and viability assayed 2 days later using a live-dead assay.

FIG. 5B—excitotoxicity assay was done with E14 mouse primary cortical neuron cultures. After 11 days of culture, cells were exposed to 10 µM glutamate for 10 min, followed by the addition of varying concentrations of Baicalein (0.2-5 µM). Cell viability was determined 24 hr later with a standard MTT assay.

FIG. 5C—PC12 cells were glucose-deprived then were incubates in the absence or presence of Baicalein. Cell viability was determined 24 hr later using the MTT assay.

FIG. 5D—RGC-5 nerve cells were treated with 30 µM iodoacetic acid for 2 hr in the presence or absence of 5-25 µM Baicalein. In some experiments, Baicalein was added 2 hr after the ischemic event. Cell survival (%) was measured after 24 hr by the MTT assay. Baicalein added before (□) or 2 hr after (●) ischemia.

FIG. 9 illustrates representative chlorogenic acid derivatives.

FIG. 9A illustrates the structure of chlorogenic acid.

FIG. 9B illustrates the structure of caffeic acid.

FIG. 9C illustrates the structure of quinic acid.

FIG. 9D illustrates the structure of cinnamic acid.

FIG. 9E illustrates the structures of certain representative substituted cinnamic acids.

FIG. 9F illustrates the structure of one exemplary cyclohexene carboxylic acid.

FIG. 9G illustrates the structure of a second exemplary cyclohexene carboxylic acid.

FIG. 9H illustrates the structure of one exemplary cyclohexene carboxylic acid diol.

FIG. 9I illustrates the structure of a second exemplary cyclohexene carboxylic acid diol.

FIG. 10 illustrates a synthetic scheme of chalcone derivatives.

FIG. 11 illustrates a synthetic scheme of flavone derivatives.

FIG. 12 illustrates a synthetic scheme of flavonol derivatives.

FIG. 13 illustrates a synthetic scheme of quinoline derivatives.

FIG. 14 provides an illustrative synthetic scheme for compounds PM-001, PM-002, PM-003, and PM-008.

FIG. 15 provides an illustrative synthetic scheme for compounds PM-004, PM-010, PM-012, and PM-013.

DETAILED DESCRIPTION

Definitions

Figure 1:
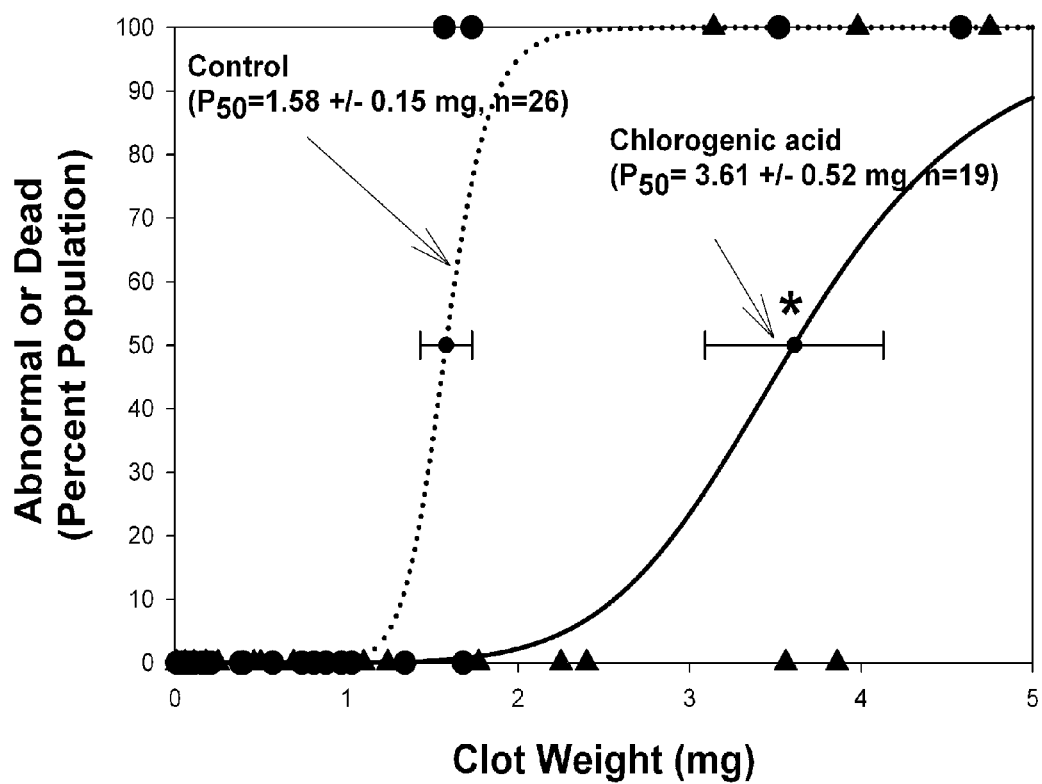
FIG. 1 illustrates behavioral improvements following chlorogenic acid (CGA) treatment in the rabbit small clot embolic stroke model (RSCEM). The cumulative control curve (dotted line) has a $P_{50}$ value of 1.58±0.15 mg (n=26). CGA treatment (50 mg/kg) initiated 5 minutes following embolization increased the $P_{50}$ value to 3.61±0.52 mg (n=19, *P<0.05) (dark solid line). The dark circles ● represent the raw data for the control group and the triangles ▲ represent the raw data for the CGA-treated group. A normal rabbit for a specific clot weight is represented by a symbol plotted at 0% on the y-axis, whereas an abnormal rabbit for a specific clot weight is represented by a symbol plotted at 100% on the y-axis.

The following words and phrases are intended to have the meanings as set forth below, except to the extent that the context in which they are used indicates otherwise or they are expressly defined to mean something different.

As used herein, "administering" refers to local and systemic administration, e.g., including enteral and parenteral administration. Routes of administration for the compounds described herein include, e.g., oral ("po") administration, administration as a suppository, topical contact, intravenous ("iv"), intraperitoneal ("ip"), intramuscular ("im"), intralesional, intranasal, or subcutaneous ("sc") administration, or the implantation of a slow-release device e.g., a mini-osmotic pump, a depot formulation, etc., to a subject. Administration can be by any route including parenteral and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, ionophoretic and intracranial. Other modes of delivery include, but are not limited to, the use of liposomal formulations, intravenous infusion, transdermal patches, etc.

The terms "systemic administration" and "systemically administered" refer to a method of administering a compound or composition to a mammal so that the compound or composition is delivered to sites in the body, including the targeted site of pharmaceutical action, via the circulatory system. Systemic administration includes, but is not limited to, oral, intranasal, rectal and parenteral (i.e., other than through the alimentary tract, such as intramuscular, intravenous, intra-arterial, transdermal and subcutaneous) administration.

The term "co-administering" or "concurrent administration", when used, for example with respect to the polyphenol compounds described herein and another active agent (e.g. a cognition enhancer), refers to administration of a polyphenol compound described and a second active agent such that both can simultaneously achieve a physiological effect. The two agents, however, need not be administered together. In certain embodiments, administration of one agent can precede administration of the other. Simultaneous physiological effect need not necessarily require presence of both agents in the circulation at the same time. However, in certain embodiments, co-administering typically results in both agents being simultaneously present in the body (e.g. in the plasma) at a significant fraction (e.g. 20% or greater, preferably 30% or 40% or greater, more preferably 50% or 60% or greater, most preferably 70% or 80% or 90% or greater) of their maximum serum concentration for any given dose.

As used herein, the terms "treating" and "treatment" refer to delaying the onset of, retarding or reversing the progress of, reducing the severity of, or alleviating or preventing either the disease or condition to which the term applies (e.g., ischemia and/or ischemic stroke), or one or more symptoms of such disease or condition.

The term "mitigating" refers to reduction or elimination of one or more symptoms of that pathology or disease, and/or a reduction in the rate or delay of onset or severity of one or more symptoms of that pathology or disease, and/or the prevention of that pathology or disease.

As used herein, the phrase "consisting essentially of" refers to the genera or species of active pharmaceutical agents included in a method or composition, as well as any excipients inactive for the intended purpose of the methods or compositions. In some embodiments, the phrase "consisting essentially of" expressly excludes the inclusion of one or more additional active agents other than a polyphenol compound, as described herein.

The terms "subject," "individual," and "patient" interchangeably refer to a mammal, preferably a human or a non-human primate, but also domesticated mammals (e.g., canine or feline), laboratory mammals (e.g., mouse, rat, rabbit, hamster, guinea pig) and agricultural mammals (e.g., equine, bovine, porcine, ovine). In various embodiments, the subject can be a human (e.g., adult male, adult female, adolescent male, adolescent female, male child, female child) under the care of a physician or other healthworker in a hospital, psychiatric care facility, as an outpatient, or other clinical context. In certain embodiments the subject may not be under the care or prescription of a physician or other healthworker.

"Ischemia" or "ischemic event" as used herein refers to diseases and disorders characterized by inadequate blood supply (i.e., circulation) to a local area due to blockage of the blood vessels to the area. Ischemia includes for example, strokes and transient ischemic attacks. Strokes include, e.g., ischemic stroke (including, but not limited to, cardioembolic strokes, atheroembolic or atherothrombotic strokes, i.e., strokes caused by atherosclerosis in the carotid, aorta, heart, and brain, small vessel strokes (i.e., lacunar strokes), strokes caused by diseases of the vessel wall, i.e., vasculitis, strokes caused by infection, strokes caused by hematological disorders, strokes caused by migraines, and strokes caused by medications such as hormone therapy), hemorrhagic ischemic stroke, intracerebral hemorrhage, and subarachnoid hemorrhage.

The term "effective amount" or "therapeutically effective amount" refers to the amount of an active agent sufficient to induce a desired biological result (e.g., prevention, delay, reduction or inhibition of ischemia or symptoms associated with ischemia). That result may be alleviation of the signs, symptoms, or causes of a disease, or any other desired alteration of a biological system. The term "therapeutically effective amount" is used herein to denote any amount of the formulation which causes a substantial improvement in a disease condition when applied to the affected areas repeatedly over a period of time. The amount will vary with the condition being treated, the stage of advancement of the condition, and the type and concentration of formulation applied. Appropriate amounts in any given instance will be readily apparent to those skilled in the art or capable of determination by routine experimentation.

"Subtherapeutic dose" refers to a dose of a pharmacologically active agent(s), either as an administered dose of pharmacologically active agent, or actual level of pharmacologically active agent in a subject that functionally is insufficient to elicit the intended pharmacological effect in itself (e.g., to dissolve an embolic clot), or that quantitatively is less than the established therapeutic dose for that particular pharmacological agent (e.g., as published in a reference consulted by a person of skill, for example, doses for a pharmacological agent published in the Physicians' Desk Reference, 66th Ed., 2011, Thomson Healthcare or Brunton, et al., Goodman & Gilman's The Pharmacological Basis of Therapeutics, 11th edition, 2006, McGraw-Hill Professional). A "subtherapeutic dose" can be defined in relative terms (i.e., as a percentage amount (less than 100%) of the amount of pharmacologically active agent conventionally administered). For example, a subtherapeutic dose amount can be about 1% to about 75% of the amount of pharmacologically active agent conventionally administered. In some embodiments, a subtherapeutic dose can be about 75%, 50%, 30%, 25%, 20%, 10% or less, than the amount of pharmacologically active agent conventionally administered.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The symbol "—" means a single bond, "=" means a double bond, "≡" means a triple bond. The symbol " $\sim\!\sim\!\sim$ " refers to a group on a double-bond as occupying either position on the terminus of the double bond to which the symbol is attached; that is, the geometry, E- or Z-, of the double bond is ambiguous and both isomers are meant to be included. When a group is depicted removed from its parent formula, the " $\sim$ " symbol will be used at the end of the bond which was theoretically cleaved in order to separate the group from its parent structural formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes particular atom in a structure is described in textual formula as having a hydrogen or hydrogens as substitution (expressly defined hydrogen), for example, $CH_2CH_2$. It would be understood by one of ordinary skill in the art that the aforementioned descriptive techniques are common in the chemical arts to provide brevity and simplicity to description of otherwise complex structures.

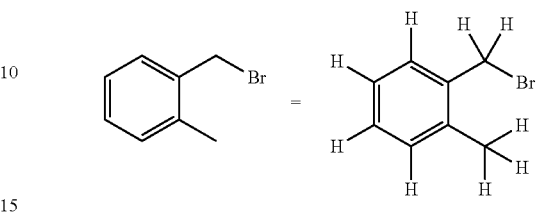

In this application, some ring structures are depicted generically and will be described textually. For example, in the schematic below if ring A is used to describe a phenyl, there are at most four hydrogens on ring A (when R is not H).

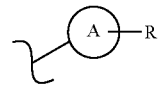

If a group R is depicted as "floating" on a ring system, as for example in the group:

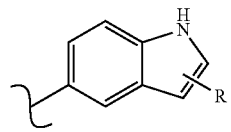

then, unless otherwise defined, a substituent R can reside on any atom of the fused bicyclic ring system, excluding the atom carrying the bond with the " " symbol, so long as a stable structure is formed. In the example depicted, the R group can reside on an atom in either the 5-membered or the 6-membered ring of the indolyl ring system.

When there are more than one such depicted "floating" groups, as for example in the formulae:

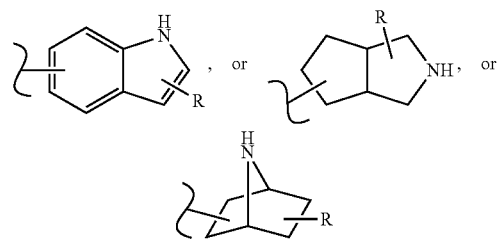

where there are two groups, namely, the R and the bond indicating attachment to a parent structure; then, unless otherwise defined, the "floating" groups can reside on any atoms of the ring system, again assuming each replaces a depicted, implied, or expressly defined hydrogen on the ring system and a chemically stable compound would be formed by such an arrangement.

When a group R is depicted as existing on a ring system containing saturated carbons, as for example in the formula:

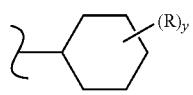

where, in this example, y can be more than one, assuming each replaces a currently depicted, implied, or expressly defined hydrogen on the ring; then, unless otherwise defined, two R's can reside on the same carbon. A simple example is when R is a methyl group; there can exist a geminal dimethyl on a carbon of the depicted ring (an "annular" carbon). In another example, two R's on the same carbon, including that same carbon, can form a ring, thus creating a spirocyclic ring (a "spirocyclyl" group) structure. Using the previous example, where two R's form, e.g. a piperidine ring in a spirocyclic arrangement with the cyclohexane, as for example in the formula:

"Alkyl" in its broadest sense is intended to include linear, branched, or cyclic hydrocarbon structures, and combinations thereof. Alkyl groups can be fully saturated or with one or more units of unsaturation, but not aromatic. Generally alkyl groups are defined by a subscript, either a fixed integer or a range of integers. For example, "$C_8$alkyl" includes n-octyl, iso-octyl, 3-octynyl, cyclohexenylethyl, cyclohexylethyl, and the like; where the subscript "8" designates that all groups defined by this term have a fixed carbon number of eight. In another example, the term "$C_{1-6}$alkyl" refers to alkyl groups having from one to six carbon atoms and, depending on any unsaturation, branches and/or rings, the requisite number of hydrogens. Examples of $C_{1-6}$alkyl groups include methyl, ethyl, vinyl, propyl, isopropyl, butyl, s-butyl, t-butyl, isobutyl, isobutenyl, pentyl, pentynyl, hexyl, cyclohexyl, hexenyl, and the like. When an alkyl residue having a specific number of carbons is named generically, all geometric isomers having that number of carbons are intended to be encompassed. For example, either "propyl" or "$C_3$alkyl" each include n-propyl, c-propyl, propenyl, propynyl, and isopropyl. Cycloalkyl is a subset of alkyl and includes cyclic hydrocarbon groups of from three to thirteen carbon atoms. Examples of cycloalkyl groups include c-propyl, c-butyl, c-pentyl, norbornyl, norbornenyl, c-hexenyl, adamantyl and the like. As mentioned, alkyl refers to alkanyl, alkenyl, and alkynyl residues (and combinations thereof)—it is intended to include, e.g., cyclohexylmethyl, vinyl, allyl, isoprenyl, and the like. An alkyl with a particular number of carbons can be named using a more specific but still generic geometrical constraint, e.g. "$C_{3-6}$cycloalkyl" which means only cycloalkyls having between 3 and 6 carbons are meant to be included in that particular definition. Unless specified otherwise, alkyl groups, whether alone or part of another group, e.g. —C(O)alkyl, have from one to twenty carbons, that is $C_{1-20}$alkyl. In the example "—C(O)alkyl," where there were no carbon count limitations defined, the carbonyl of the —C(O)alkyl group is not included in the carbon count, since "alkyl" is designated generically. But where a specific carbon limitation is given, e.g. in the term "optionally substituted $C_{1-20}$alkyl," where the optional substitution includes "oxo" the carbon of any carbonyls formed by such "oxo" substitution are included in the carbon count since they were part of the original carbon count limitation. However, again referring to "optionally substituted $C_{1-20}$alkyl," if optional substitution includes carbon-containing groups, e.g. $CH_2CO_2H$, the two carbons in this group are not included in the $C_{1-20}$alkyl carbon limitation.

When a carbon number limit is given at the beginning of a term which itself comprises two terms, the carbon number limitation is understood as inclusive for both terms. For example, for the term "$C_{7-14}$arylalkyl," both the "aryl" and the "alkyl" portions of the term are included the carbon count, a maximum of 14 in this example, but additional substituent groups thereon are not included in the atom count unless they incorporate a carbon from the group's designated carbon count, as in the "oxo" example above. Likewise when an atom number limit is given, for example "6-14 membered heteroarylalkyl," both the "heteroaryl" and the "alkyl" portion are included the atom count limitation, but additional substituent groups thereon are not included in the atom count unless they incorporate a carbon from the group's designated carbon count. In another example, "$C_{4-10}$cycloalkylalkyl" means a cycloalkyl bonded to the parent structure via an alkylene, alkylidene or alkylidyne; in this example the group is limited to 10 carbons inclusive of the alkylene, alkylidene or alkylidyne subunit. As another example, the "alkyl" portion of, e.g. "$C_{7-14}$arylalkyl" is meant to include alkylene, alkylidene or alkylidyne, unless stated otherwise, e.g. as in the terms "$C_{7-14}$arylalkylene" or "$C_{6-10}$aryl—$CH_2CH_2$—."

"Alkylene" refers to straight, branched and cyclic (and combinations thereof) divalent radical consisting solely of carbon and hydrogen atoms, containing no unsaturation and having from one to ten carbon atoms, for example, methylene, ethylene, propylene, n-butylene and the like. Alkylene is like alkyl, referring to the same residues as alkyl, but having two points of attachment and, specifically, fully saturated. Examples of alkylene include ethylene (—$CH_2CH_2$—), propylene (—$CH_2CH_2CH_2$—), dimethylpropylene (—$CH_2C(CH_3)_2CH_2$—), cyclohexan-1,4-diyl and the like.

"Alkylidene" refers to straight, branched and cyclic (and combinations thereof) unsaturated divalent radical consisting solely of carbon and hydrogen atoms, having from two to ten carbon atoms, for example, ethylidene, propylidene, n-butylidene, and the like. Alkylidene is like alkyl, referring to the same residues as alkyl, but having two points of attachment and, specifically, at least one unit of double bond unsaturation. Examples of alkylidene include vinylidene (—CH=CH—), cyclohexylvinylidene (—CH=C($C_6H_{13}$)—), cyclohexen-1,4-diyl and the like.

"Alkylidyne" refers to straight, branched and cyclic (and combinations thereof) unsaturated divalent radical consisting solely of carbon and hydrogen atoms having from two to ten carbon atoms, for example, propylid-2-ynyl, n-butylid-1-ynyl, and the like. Alkylidyne is like alkyl, referring to the same residues as alkyl, but having two points of attachment and, specifically, at least one unit of triple bond unsaturation.

Any of the above radicals" "alkylene," "alkylidene" and "alkylidyne," when optionally substituted, can contain alkyl substitution which itself can contain unsaturation. For example, 2-(2-phenylethynyl-but-3-enyl)-naphthalene (IUPAC name) contains an n-butylid-3-ynyl radical with a vinyl substituent at the 2-position of the radical. Combinations of alkyls and carbon-containing substitutions thereon are limited to thirty carbon atoms.

"Alkoxy" refers to the group —O-alkyl, where alkyl is as defined herein. Alkoxy includes, by way of example, methoxy, ethoxy, n-propoxy, isopropoxy, n-butoxy, t-butoxy, sec-butoxy, n-pentoxy, cyclohexyloxy, cyclohexenyloxy, cyclopropylmethyloxy, and the like.

"Haloalkyloxy" refers to the group —O-alkyl, where alkyl is as defined herein, and further, alkyl is substituted with one or more halogens. By way of example, a haloC$_{1-3}$alkyloxy" group includes —OCF$_3$, —OCF$_2$H, —OCHF$_2$, —OCH$_2$CH$_2$Br, —OCH$_2$CH$_2$CH$_2$I, —OC(CH$_3$)$_2$Br, —OCH$_2$Cl and the like.

"Acyl" refers to the groups —C(O)H, —C(O)alkyl, —C(O)aryl and C(O)heterocyclyl.

"α-Amino Acids" refer to naturally occurring and commercially available α-amino acids and optical isomers thereof. Typical natural and commercially available α-amino acids are glycine, alanine, serine, homoserine, threonine, valine, norvaline, leucine, isoleucine, norleucine, aspartic acid, glutamic acid, lysine, ornithine, histidine, arginine, cysteine, homocysteine, methionine, phenylalanine, homophenylalanine, phenylglycine, ortho-tyrosine, meta-tyrosine, para-tyrosine, tryptophan, glutamine, asparagine, proline and hydroxyproline. A "side chain of an α-amino acid" refers to the radical found on the α-carbon of an α-amino acid as defined above, for example, hydrogen (for glycine), methyl (for alanine), benzyl (for phenylalanine), etc.

"Amino" refers to the group NH$_2$.

"Amide" refers to the group C(O)NH$_2$ or —N(H)acyl.

"Aryl" (sometimes referred to as "Ar") refers to a monovalent aromatic carbocyclic group of, unless specified otherwise, from 6 to 15 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, 9,10-dihydrophenanthrenyl, indanyl, tetralinyl, and fluorenyl and the like), provided that the point of attachment is through an atom of an aromatic portion of the aryl group and the aromatic portion at the point of attachment contains only carbons in the aromatic ring. If any aromatic ring portion contains a heteroatom, the group is a heteroaryl and not an aryl. Aryl groups are monocyclic, bicyclic, tricyclic or tetracyclic.

"Arylene" refers to an aryl that has at least two groups attached thereto. For a more specific example, "phenylene" refers to a divalent phenyl ring radical. A phenylene, thus can have more than two groups attached, but is defined by a minimum of two non-hydrogen groups attached thereto.

"Arylalkyl" refers to a residue in which an aryl moiety is attached to a parent structure via one of an alkylene, alkylidene, or alkylidyne radical. Examples include benzyl, phenethyl, phenylvinyl, phenylallyl and the like. When specified as "optionally substituted," both the aryl, and the corresponding alkylene, alkylidene, or alkylidyne portion of an arylalkyl group can be optionally substituted. By way of example, "C$_{7-11}$arylalkyl" refers to an arylalkyl limited to a total of eleven carbons, e.g., a phenylethyl, a phenylvinyl, a phenylpentyl and a naphthylmethyl are all examples of a "C$_{7-11}$arylalkyl" group.

"Aryloxy" refers to the group —O-aryl, where aryl is as defined herein, including, by way of example, phenoxy, naphthoxy, and the like.

"Carboxyl," "carboxy" or "carboxylate" refers to CO$_2$H or salts thereof.

"Carboxyl ester" or "carboxy ester" or "ester" refers to the group —CO$_2$alkyl, —CO$_2$aryl or —CO$_2$heterocyclyl.

"Carbonate" refers to the group —OCO$_2$alkyl, —OCO$_2$aryl or —OCO$_2$heterocyclyl.

"Carbamate" refers to the group —OC(O)NH$_2$, —N(H)carboxyl or —N(H)carboxyl ester.

"Cyano" or "nitrile" refers to the group —CN.

"Formyl" refers to the specific acyl group —C(O)H.

"Halo" or "halogen" refers to fluoro, chloro, bromo and iodo.

"Haloalkyl" and "haloaryl" refer generically to alkyl and aryl radicals that are substituted with one or more halogens, respectively. By way of example "dihaloaryl," "dihaloalkyl," "trihaloaryl" etc. refer to aryl and alkyl substituted with a plurality of halogens, but not necessarily a plurality of the same halogen; thus 4-chloro-3-fluorophenyl is a dihaloaryl group.

"Heteroalkyl" refers to an alkyl where one or more, but not all, carbons are replaced with a heteroatom. A heteroalkyl group has either linear or branched geometry. By way of example, a "2-6 membered heteroalkyl" is a group that can contain no more than 5 carbon atoms, because at least one of the maximum 6 atoms must be a heteroatom, and the group is linear or branched. Also, for the purposes of this invention, a heteroalkyl group always starts with a carbon atom, that is, although a heteroalkyl may contain one or more heteroatoms, the point of attachment to the parent molecule is not a heteroatom. A 2-6 membered heteroalkyl group includes, for example, —CH$_2$XCH$_3$, —CH$_2$CH$_2$XCH$_3$, —CH$_2$CH$_2$XCH$_2$CH$_3$, C(CH$_2$)$_2$XCH$_2$CH$_3$ and the like, where X is O, NH, NC$_{1-6}$alkyl and S(O)$_{0-2}$, for example.

"Perhalo" as a modifier means that the group so modified has all its available hydrogens replaced with halogens. An example would be "perhaloalkyl." Perhaloalkyls include —CF$_3$, —CF$_2$CF$_3$, perchloroethyl and the like.

"Hydroxy" or "hydroxyl" refers to the group —OH.

"Heteroatom" refers to O, S, N, or P.

"Heterocyclyl" in the broadest sense includes aromatic and non-aromatic ring systems and more specifically refers to a stable three- to fifteen-membered ring radical that consists of carbon atoms and from one to five heteroatoms. For purposes of this description, the heterocyclyl radical can be a monocyclic, bicyclic or tricyclic ring system, which can include fused or bridged ring systems as well as spirocyclic systems; and the nitrogen, phosphorus, carbon or sulfur atoms in the heterocyclyl radical can be optionally oxidized to various oxidation states. In a specific example, the group —S(O)$_{0-2}$—, refers to —S— (sulfide), —S(O)— (sulfoxide), and —SO$_2$— (sulfone) linkages. For convenience, nitrogens, particularly but not exclusively, those defined as annular aromatic nitrogens, are meant to include their corresponding N-oxide form, although not explicitly defined as such in a particular example. Thus, for a compound having, for example, a pyridyl ring; the corresponding pyridyl-N-oxide is meant to be included in the presently disclosed compounds. In addition, annular nitrogen atoms can be optionally quaternized.

"Heterocycle" includes heteroaryl and heteroalicyclyl, that is a heterocyclic ring can be partially or fully saturated or aromatic. Thus a term such as "heterocyclylalkyl" includes heteroalicyclylalkyls and heteroarylalkyls. Examples of heterocyclyl radicals include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, diazabicycloheptane, diazapane, diazepine, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Heteroaryl" refers to an aromatic group having from 1 to 10 annular carbon atoms and 1 to 4 annular heteroatoms. Heteroaryl groups have at least one aromatic ring component, but heteroaryls can be fully unsaturated or partially unsaturated. If any aromatic ring in the group has a heteroatom, then the group is a heteroaryl, even, for example, if other aromatic rings in the group have no heteroatoms. For example, 2H-pyrido[3,2-b][1,4]oxazin-3(4H)-one-7-yl, indolyl and benzimidazolyl are "heteroaryls." Heteroaryl groups can have a single ring (e.g., pyridinyl, imidazolyl or furyl) or multiple condensed rings (e.g., indolizinyl, quinolinyl, benzimidazolyl or benzothienyl), where the condensed rings may or may not be aromatic and/or contain a heteroatom, provided that the point of attachment to the parent molecule is through an atom of the aromatic portion of the heteroaryl group. In one embodiment, the nitrogen and/or sulfur ring atom(s) of the heteroaryl group are optionally oxidized to provide for the N-oxide (N→O), sulfinyl, or sulfonyl moieties. Compounds described herein containing phosphorous, in a heterocyclic ring or not, include the oxidized forms of phosphorous. Heteroaryl groups are monocyclic, bicyclic, tricyclic or tetracyclic.

"Heteroaryloxy" refers to O-heteroaryl.

"Heteroarylene" generically refers to any heteroaryl that has at least two groups attached thereto. For a more specific example, "pyridylene" refers to a divalent pyridyl ring radical. A pyridylene, thus can have more than two groups attached, but is defined by a minimum of two non-hydrogen groups attached thereto.

"Heteroalicyclic" refers specifically to a non-aromatic heterocyclyl radical. A heteroalicyclic may contain unsaturation, but is not aromatic. As mentioned, aryls and heteroaryls are attached to the parent structure via an aromatic ring. So, e.g., 2H-1,4-benzoxazin-3(4H)-one-4-yl is a heteroalicyclic, while 2H-1,4-benzoxazin-3(4H)-one-7-yl is an aryl. In another example, 2H-pyrido[3,2-b][1,4]oxazin-3 (4H)-one-4-yl is a heteroalicyclic, while 2H-pyrido[3,2-b][1,4]oxazin-3(4H)-one-7-yl is a heteroaryl.

"Heterocyclylalkyl" refers to a heterocyclyl group linked to the parent structure via e.g an alkylene linker, for example (tetrahydrofuran-3-yl)methyl- or (pyridin-4-yl)methyl

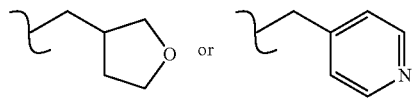

"Heterocyclyloxy" refers to the group —O—heterocycyl.
"Nitro" refers to the group —NO$_2$.
"Oxo" refers to a double bond oxygen radical, =O.
"Oxy" refers to —O.radical (also designated as →O), that is, a single bond oxygen radical. By way of example, N-oxides are nitrogens bearing an oxy radical.

When a group with its bonding structure is denoted as being bonded to two partners; that is, a divalent radical, for example, —OCH$_2$—, then it is understood that either of the two partners can be bound to the particular group at one end, and the other partner is necessarily bound to the other end of the divalent group, unless stated explicitly otherwise. Stated another way, divalent radicals are not to be construed as limited to the depicted orientation, for example "—OCH$_2$—" is meant to mean not only "—OCH$_2$—" as drawn, but also "—CH$_2$O—."

"Optional" or "optionally" means that the subsequently described event or circumstance may or may not occur, and that the description includes instances where said event or circumstance occurs and instances in which it does not. One of ordinary skill in the art would understand that, with respect to any molecule described as containing one or more optional substituents, that only synthetically feasible compounds are meant to be included. "Optionally substituted" refers to all subsequent modifiers in a term, for example in the term "optionally substituted arylC$_{1-8}$alkyl," optional substitution may occur on both the "C$_{1-8}$alkyl" portion and the "aryl" portion of the arylC$_{1-8}$alkyl group. Also by way of example, optionally substituted alkyl includes optionally substituted cycloalkyl groups. The term "substituted," when used to modify a specified group or radical, means that one or more hydrogen atoms of the specified group or radical are each, independently of one another, replaced with the same or different substituent groups as defined below. Thus, when a group is defined as "optionally substituted" the definition is meant to encompass when the groups is substituted with one or more of the radicals defined below, and when it is not so substituted.

Substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —N(R$^{80}$)$_2$, perhaloalkyl, —OCN, —SCN, —NO, —NO$_2$, =N$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —P(O)(O$^-$)$_2$(M$^+$)$_2$, —P(O)(O$^-$)$_2$M$^{2+}$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)N(R$^{80}$)$_2$, —C(NR$^{70}$) (R$^{80}$)$_2$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S) R$^{70}$, —NR$^{70}$CO$_2^-$M$^+$, —NR$^{70}$CO$_2$R$^{70}$, —NR$^{70}$C(S)OR$^{70}$, —NR$^{70}$C(O)N(R$^{80}$)$_2$, —NR$^{70}$C(NR$^{70}$)R$^{70}$ and —NR$^{70}$C (NR$^{70}$)N(R$^{80}$)$_2$, where R$^{60}$ is C$_{1-6}$alkyl, 3 to 10-membered heterocyclyl, 3 to 10-membered heterocyclylC$_{1-6}$alkyl, C$_{6-10}$aryl or C$_{6-10}$arylC$_{1-6}$alkyl; each R$^{70}$ is independently for each occurence hydrogen or R$^{60}$; each R$^{80}$ is independently for each occurence R$^{70}$ or alternatively, two R$^{80}$'s, taken together with the nitrogen atom to which they are bonded, form a 3 to 7-membered heteroalicyclyl which optionally includes from 1 to 4 of the same or different additional heteroatoms selected from O, N and S, of which N optionally has H or C$_1$-C$_3$alkyl substitution; and each M$^+$ is a counter ion with a net single positive charge. Each M$^+$ is independently for each occurence, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ (a "subscript 0.5 means e.g. that one of the counter ions for such divalent alkali earth ions can be an ionized form of a compound described herein and the other a typical counter ion such as chloride, or two ionized compounds can serve as counter ions for such divalent alkali earth ions, or a doubly ionized compound can serve as the counter ion for such divalent alkali earth ions). As specific examples, —N($R^{80}$)$_2$ is meant to include —NH$_2$, —NH-alkyl, —NH-pyrrolidin-3-yl, N-pyrrolidinyl, N-piperazinyl, 4N-methyl-piperazin-1-yl, N-morpholinyl and the like.

Substituent groups for replacing hydrogens on unsaturated carbon atoms in groups containing unsaturated carbons are, unless otherwise specified, —$R^{60}$, halo, —O$^-$M$^+$, —OR$^{70}$, —SR$^{70}$, —S$^-$M$^+$, —N($R^{80}$)$_2$, perhaloalkyl, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_3^{-2}$(M$^+$)$_2$, —PO$_3^{-2}$M$^{2+}$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)N(R$^{80}$)$_2$, —OC(O)R$^{70}$, —OC(S)R$^{70}$, —OCO$_2^{31}$ M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)N(R$^{80}$)$_2$, —NR$^{70}$C(NR$^{70}$)R$^{70}$ and —NR$^{70}$C(NR$^{70}$)N(R$^{80}$)$_2$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

Substituent groups for replacing such hydrogens on nitrogen atoms in groups containing such nitrogen atoms are, unless otherwise specified, —R$^{60}$, —O$^-$M$^+$, —OR$^{70}$, —SR$^{70}$, —S$^-$M$^+$, —N(R$^{80}$)$_2$, perhaloalkyl, —CN, —NO, —NO$_2$, —S(O)$_2$R$^{70}$, —SO$_3^-$M$^+$, —SO$_3$R$^{70}$, —OS(O)$_2$R$^{70}$, —OSO$_3$_M$^+$, —OSO$_3$R$^{70}$, —PO$_3^{2-}$(M$^+$)$_2$, —PO$_3^{2-}$M$^{2+}$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —CO$_2$R$^{70}$, —C(S)OR$^{70}$, —C(O)NR$^{80}$R$^{80}$, —C(NR$^{70}$)NR$^{80}$R$^{80}$, OC(O)R$^{70}$, —OC(S)R$^{70}$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$R$^{70}$, —NR$^{70}$C(S)OR$^{70}$, —NR$^{70}$C(O)N(R$^{80}$)$_2$, —NR$^{70}$C(NR$^{70}$)R$^{70}$ and —NR$^{70}$C(NR$^{70}$)N(R$^{80}$)$_2$, where R$^{60}$, R$^{70}$, R$^{80}$ and M$^+$ are as previously defined.

In one embodiment, a group that is substituted has 1, 2, 3, or 4 substituents, 1, 2, or 3 substituents, 1 or 2 substituents, or 1 substituent.

It is understood that in all substituted groups, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such case that the language permits such multiple substitutions, the maximum number of such iterations of substitution is three.

"Sulfonamide" refers to the group —SO$_2$NH$_2$, —N(H)SO$_2$H, —N(H)SO$_2$alkyl, —N(H)SO$_2$aryl, or —N(H)SO$_2$heterocyclyl.

"Sulfonyl" refers to the group —SO$_2$H, —SO$_2$alkyl, —SO$_2$aryl, or —SO$_2$heterocyclyl.

"Sulfanyl" refers to the group: —SH, —S-alkyl, —S-aryl, or —S-heterocyclyl.

"Sulfinyl" refers to the group: —S(O)H, —S(O)alkyl, —S(O)aryl or —S(O)heterocyclyl.

"Suitable leaving group" is defined as the term would be understood by one of ordinary skill in the art; that is, a group on a carbon, where upon reaction a new bond is to be formed, the carbon loses the group upon formation of the new bond. A typical example employing a suitable leaving group is a nucleophilic substitution reaction, e.g., on a sp$^3$ hybridized carbon (SN$_2$ or SN$_1$), e.g. where the leaving group is a halide, such as a bromide, the reactant might be benzyl bromide. Another typical example of such a reaction is a nucleophilic aromatic substitution reaction (SNAr). Another example is an insertion reaction (for example by a transition metal) into the bond between an aromatic reaction partner bearing a leaving group followed by reductive coupling. "Suitable leaving group" is not limited to such mechanistic restrictions. Examples of suitable leaving groups include halogens, optionally substituted aryl or alkyl sulfonates, phosphonates, azides and —S(O)$_{0-2}$R where R is, for example optionally substituted alkyl, optionally substituted aryl, or optionally substituted heteroaryl. Those of skill in the art of organic synthesis will readily identify suitable leaving groups to perform a desired reaction under different reaction.

"Stereoisomer" and "stereoisomers" refer to compounds that have the same atomic connectivity but different atomic arrangement in space. Stereoisomers include cis-trans isomers, E and Z isomers, enantiomers and diastereomers. Compounds described herein, or their pharmaceutically acceptable salts can contain one or more asymmetric centers and can thus give rise to enantiomers, diastereomers, and other stereoisomeric forms that can be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers can be prepared using chiral synthons, chiral reagents, or resolved using conventional techniques, such as by: formation of diastereoisomeric salts or complexes which can be separated, for example, by crystallization; via formation of diastereoisomeric derivatives which can be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer can be synthesized by asymmetric synthesis using optically active reagents, substrates, catalysts or solvents, or by converting on enantiomer to the other by asymmetric transformation. For a mixture of enantiomers, enriched in a particular enantiomer, the major component enantiomer can be further enriched (with concomitant loss in yield) by recrystallization.

When the compounds described herein contain olefinic double bonds or other centers of geometric asymmetry, and unless specified otherwise, it is intended that the compounds include both E and Z geometric isomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible and contemplated herein.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. Pharmaceutically acceptable acid addition salts are those salts that retain the biological effectiveness of the free bases while formed by acid partners that are not biologically or otherwise undesirable, e.g., inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Pharmaceutically acceptable base addition salts include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.).

"Prodrug" refers to compounds that are transformed in vivo to yield the parent compound, for example, by hydrolysis in the gut or enzymatic conversion in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) where the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention can be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8$^{th}$ Ed., Pergamon Press, Gilman et al. (eds), 1990 which is herein incorporated by reference). The metabolite of a compound described herein or its salt can itself be a biologically active compound in the body. While a prodrug described herein would meet this criteria, that is, form a described biologically active parent compound in vivo, "metabolite" is meant to encompass those compounds not contemplated to have lost a progroup, but rather all other compounds that are formed in vivo upon administration of a compound described herein which retain the biological activities described herein. Thus one aspect of the invention is a metabolite of a compound described herein. For example, a biologically active metabolite is discovered serendipitously, that is, no prodrug design per se was undertaken. Stated another way, biologically active compounds inherently formed as a result of practicing methods of the invention, are contemplated and disclosed herein. "Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. The compounds described herein can exist in unsolvated as well as solvated forms with solvents, pharmaceutically acceptable or not, such as water, ethanol, and the like. Solvated forms of the presently disclosed compounds are contemplated herein and are encompassed by the invention, at least in generic terms.

It is understood that the above definitions are not intended to include impermissible substitution patterns (e.g., methyl substituted with 5 fluoro groups). Such impermissible substitution patterns are easily recognized by a person having ordinary skill in the art.

Detailed Description

1. Introduction a. Acute Ischemic Stroke Cascade

During the last 50 years, experimental stroke research has identified many factors responsible for the death of neurons and glial cells following ischemic stroke. One of the primary causes of cell death is "energy failure", or depletion of high-energy phosphates, which occurs quickly after ischemia [5, 16, 26-29]. In embolic strokes, impairment of the microcirculation may also be a contributing factor to the evolution of ischemia distal to the infarct [30] Immediately following an embolic stroke, excitatory amino acid (EAA) neurotransmitters are released in quantity from presynaptic terminals. Some EAAs, especially glutamate, can propagate the ischemic response and also cause "delayed neuronal death" or the protracted necrosis of neurons [31-35]. Of importance are the roles of free-radical species, oxygen free radicals and superoxides, which are produced in abundance following ischemic injury and have been identified as possible mediators of ischemic necrosis and vascular damage [5, 36-38]. Following a stroke, a cascade of mechanisms are activated, which cause substantial injury not only to the core, but also the "ischemic penumbra", defined as a zone or portion of brain tissue that is potentially salvageable [39, 40] by appropriate treatment, if administered in a timely fashion. The cells in the "ischemic penumbra" appear to be a valid target for neuroprotective agents, since they may survive if the deleterious actions of specific mediators of the ischemic cascade, such as free radicals are suppressed or blocked.

b. Neuroprotective Polyphenol Compounds for the Treatment of Neurological Disorders Polyphenolic compounds are micronutrients which have become of interest because they are found in fruits and vegetables and their products such as tea, coffee, red wine and olive oil [41-46]. The plant-derived natural products have been postulated to reduce the risk of cardiovascular diseases [45-49]. Recently, the "French Paradox" has received a great deal of attention pointing to the possible benefits of the Mediterranean diet, which includes high amounts of fresh fruits and vegetables as well as red wine [41-44]. The pharmacological basis of the Mediterranean diet may lie in the abundance of polyphenolic compounds in the natural products of the diet [45, 48, 49]. There has been some interest in the potential protective mechanisms of the polyphenolic molecules in neurodegenerative disease and neuronal cell death [47, 50-52]. Using an oxidative stress model, Maher and colleagues [53] as well as other investigators [47, 50, 54] have shown that Fisetin (3,3',4',7-tetrahydroxyflavone) can modulate intracellular signals and reduce oxidation-induced apoptotic mechanisms. A rodent study showed that quercetin (3,3',4',5,7 pentahydroxyflavone) could reduce neurological deficits and cerebral infarction area following an ischemic event [55], and resveratrol (5-[(E)-2-(4-hydroxyphenyl)-ethenyl]benzene-1,3-diol) may be useful in the treatment of stroke [56-58]. Thus, it appears that several polyphenolic compounds with diverse structural elements can reduce ischemia-induced neuronal degeneration and neurological deficits.

i. Chlorogenic Acid (CGA)

Many foods such as artichokes, blueberries and coffee contain high amounts of chlorogenic acid [(1,3,4,5-tetrahydroxy-cyclohexanecarboxylic acid 3-(3,4-dihydroxycinnamate), CGA [31, 59, 60] a polyphenol ester of caffeic acid and quinic acid [45, 46, 61, 62]. The polyphenolic phenylpropanoid ester CGA has long thought to have antioxidant properties [59, 63, 64] and thus may be beneficial in the treatment of stroke. The recent scientific literature on CGA suggests that it may produce beneficial effects via multiple mechanisms of action. Besides being an antioxidant, CGA has anti-inflammatory properties in rats [65] and it has also recently been described as a high affinity (or strong) metalloproteinase-9 (MMP-9) inhibitor [66]. Considering the importance of all three mechanisms in the progression of stroke [67-74], CGA appears to be a strong drug candidate for investigation as a therapeutic to reduce or attenuate the detrimental behavioral consequences of embolic stroke. Results show that CGA effectively improves behavior following in the rabbit small clot embolic stroke model (RSCEM) (FIG. 1).

ii. Fisetin

Figure 2:
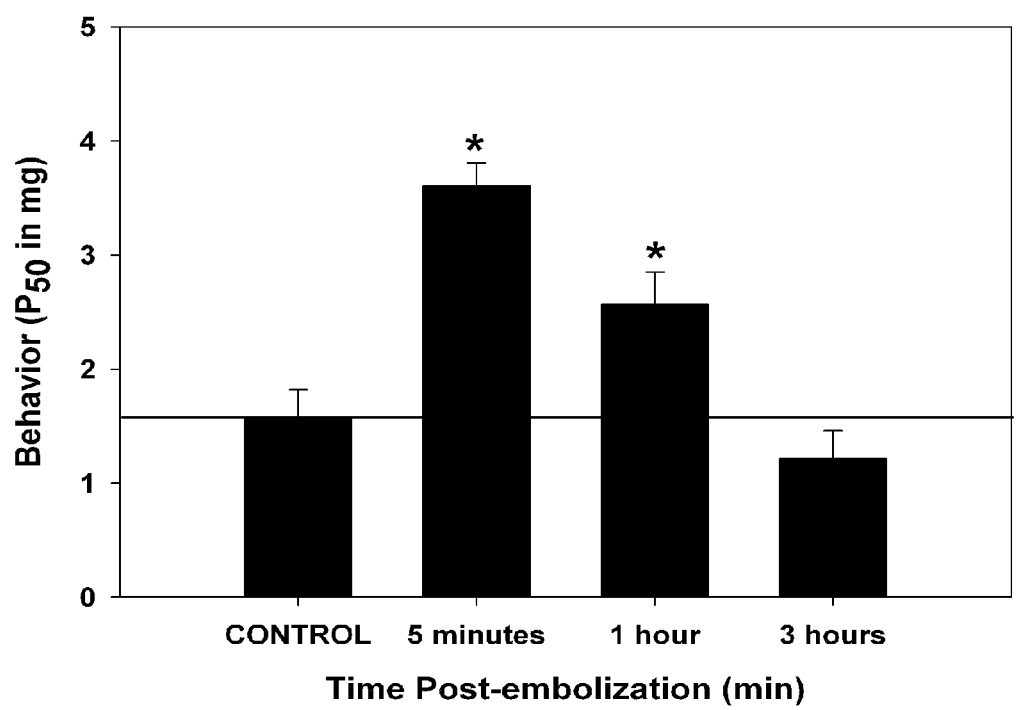
FIG. 2 illustrates that the therapeutic window for CGA when administered following embolic strokes in rabbits is 60 minutes. The graph shows Behavior ($P_{50}$ value) as a function of Time post-embolization (minutes). CGA effectively increased the $P_{50}$ value when administered 5 and 60 minutes following embolization (P<0.05 compared to a vehicle-treated control group).

Fisetin (3,7,3', 4'-Tetrahydroxyflavone) is a member of the flavonoid family of structurally heterogeneous, polyphenolic compounds which are thought to have potent antioxidant and free radical scavenging properties [75]. Flavonoids protect nerve cells from oxidative stress by three distinct mechanisms, only one of which is directly related to their antioxidant activity [53]. In addition to preventing the accumulation of reactive oxygen species (ROS), flavonoids can block the early loss of cellular glutathione (GSH) or the late influx of $Ca^{+2}$ into cells. More recently, it has been found that specific flavonoids possess neurotrophic activities and can promote the development, maintenance and regeneration of nerve cells. The ability of flavonoids to induce neurite outgrowth in PC12 cells using a well-studied model of neuronal differentiation. It was found that a small subset of the flavonoids which were neuroprotective could also induce neurite outgrowth and the best of these was the flavone, Fisetin [53]. The induction of neurite outgrowth by Fisetin is dependent upon activation of the Ras—Raf-ERK pathway. Fisetin was also tested for its ability to enhance memory using the object discrimination test, a well-established model for studying memory in mice. It was found that an oral dose of Fisetin potentiates memory equally as well as rolipram [76]. These results indicate that certain flavonoids could be very useful for promoting the recovery of damaged nerves as well as preventing nerve cell death. As a result of these neuroprotective actions, it was determined whether Fisetin was effective in reducing ischemic damage. FIG. 2 shows that Fisetin is also neuroprotective in the RSCEM.

iii. Baicalein

Lipoxygenases (LOXs) are dioxygenases that incorporate molecular oxygen into polyunsaturated fatty acids and, based on the site of insertion of the oxygen, are generally classified as 5-, 12-, or 15-LOXs [77]. Recent evidence suggests that 12-LOX may play a role in ischemia-induced nerve cell loss and edema, which is a major complication associated with unfavorable outcome after ischemic stroke [78]. There is a correlation between an early reduction in GSH levels in ischemia and the activation of 12-LOX [79, 80]. Using in vitro cell culture assays, 12-LOX inhibitors have been shown to block glutamate-induced cell death [80] and both 5- and 12-LOX inhibitors block ischemic injury in hippocampal slice cultures [81]. Baicalein (5,6,7trihydroxyflavone) is also a 12/15-LOX inhibitor that reduces neutrophil-mediated inflammatory reactions in rat brain ischemia [82]. Baicalein is a potent free radical scavenger and xanthine oxidase inhibitor [83, 84]. In addition to 12-LOX, Baicalein has a weak inhibitory effect on 5-LOX and leukotriene synthesis [85]. It has, in fact, been observed that many flavonoids have the ability to inhibit both LOX and COX subtypes [86]. Taken together, it appears that 12/15-LOX are important enzymes that may mediate neurodegeneration following ischemia. Preliminary evidence showing that the 12/15-LOX inhibitor reduces infarct volume following a stroke has been published [82, 87].

While the inhibition of 12-LOX by Baicalein is neuroprotective and Baicalein works well in the rabbit stroke model and a rodent stroke model, Baicalein functions, at least in part, by the inhibition of 12-LOX. While it has been shown that the products of 12-LOX are toxic, others have demonstrated that a product of the LOX enzymes, 19,17S-docasatriene (NPD1), is neuroprotective in various models, including mouse ischemia [88]. While NPD1 is primarily derived from fatty acid metabolism through 15-LOX [88], Baicalein is primarily an inhibitor of 12-LOX and therefore the synthesis of this important pro-survival molecule should not be significantly altered in the presence of Baicalein. Another LOX metabolite is arachidonic acid, HETE, is angiogenic, and it is advantageous to promote new blood vessel growth following stroke [89]. However, as with NPD1, HETE made by 15-LOX, 15(S)-HETE is much more potent than 5(S)-HETE or 12(S)-HETE [89]. Therefore, the inhibition of 12-LOX by Baicalein should not have a significant effect on neovascularization following ischemia.

Recently, Lo and colleagues have published a series of studies showing that LOX inhibitors such as Baicalein may be neuroprotective to neurons and also prevent vascular damage and edema following ischemic strokes [78, 90]. In fact, a recent report from van Leyen and colleagues have suggested that the group is undertaking a drug development approach to treat stroke by virtual screening of libraries in order to identify new LOX inhibitor candidates [78, 90]. Taken together, the results from preclinical studies from Lo and colleagues along preclinical studies further support LOX as a valuable target to treat stroke.

The three drug classes described above were studied. Chlorogenic acid, Fisetin and Baicalein are all members of the polyphenolic family of compounds that have antioxidant activity. Moreover, there is substantial information in the literature describing the multifunctionality of each of the compounds. The evidence shows that the three polyphenolic compounds with diverse structural elements can reduce ischemia-induced neuronal degeneration and neurological deficits. On the basis of strong in vitro and in vivo preliminary data, the polyphenol compounds described herein were studies and new derivatives for testing were synthesized, which can be more effective than the parent compounds.

2. Subjects Amenable to Treatment

Various embodiments of the present invention provide for a methods of treating ischemia or a condition where ischemia occurs, comprising administering the polyphenol analog to a subject in need thereof. The method may further comprise identifying the subject in need of treatment or prevention for ischemia or the condition where ischemia occurs.

Subjects amenable to treatment include those who have experienced an ischemic event, for example, an embolic stroke. In a subject known to have experienced ischemia or an ischemic event, the polyphenol compound(s) are generally administered within 24 hours of the estimated occurrence of the ischemic event, for example, within 20 hours, 18 hours, 16 hours, 12 hours, 10 hours, 8 hours, 5 hours, 3 hours, 1 hour, or less, of the estimated occurrence of the ischemic event. In various embodiments, the polyphenol compound(s) can be administered 5, 10, 20, 30, 45, 60, 75, 90, 105, and/or 120 minutes after the ischemic event. In various embodiments, the polyphenol compound(s) can be administered within 2, 3, 4, 5 and/or 6 hours after the ischemic event. In various embodiments, the polyphenol compound(s) can be administered up to 6 hours, for example, up to 12 hours or 24 hours, after the ischemic event.

In some embodiments, the subject is at risk for developing an ischemia, and the polyphenol compound(s) are administered prophylactically to prevent the occurrence of an ischemic event. For example, the subject may be scheduled to undergo major surgery, in which the surgical procedure exposes the subject to risk of an ischemic event, e.g., an embolic stroke. In various embodiments, the polyphenol compound(s) can be administered to a subject undergoing cardiac surgery, e.g., cardiac bypass surgery, to reduce the risk or prevent the occurrence of the subject experiencing an ischemic event. The compounds can be administered prior to, during and/or after surgery in order to prevent or mitigate the occurrence of ischemia.

3. Conditions Subject to Treatment

The polyphenol compound(s) can be useful for the treatment of ischemia, including cardiovascular ischemia and ischemic stroke. In some embodiments, the subject has experienced or is at risk of experiencing an embolic stroke, e.g., a cardioembolic or an atherothrombotic stroke.

Ischemia is the result of low to no blood flow resulting in clinically recognizable deficits. There is one underlying commonality between all types of ischemia, the activation of the "ischemic cascade". Key components of the cascade include reduced tissue metabolism, depletion of energy stores, and, depending upon the duration of the initial insult, triggering of a cascade of excitotoxicity, free radical formation, inflammation, vascular injury and programmed cell death, which results in cell death.

For example, in stroke, reduced blood flow and severe oxygen deficiency leads to an ischemic brain area, comprised of a central core of severely ischemic tissue that will die, surrounded by a tissue zone consisting of moderate ischemic tissue with preserved cellular metabolism and viability. For a yet undefined period of time after a stroke, there appears to be a region of salvageable tissue commonly referred to as a "penumbra" to target with novel therapies such as polyphenols in order to improve cellular and clinical functions.

Free radical species appear to be important mediators in the progression of the ischemic cascade resulting in cell death and clinical deficits. This is central to many diseases where there is an ischemic component. Free radicals are chemical compounds having one or more unpaired electrons, which makes them highly reactive with a variety of brain substrates. Free radicals can be classified by their core reactive species, oxygen, nitrogen or sulfur. Reactive oxygen species (ROS) usually refers to oxygen-based molecules such as superoxide, hydrogen peroxide ($H_2O_2$), hydroxyl radical, singlet oxygen, whereas a reactive nitrogen species can include nitric oxide (NO) and peroxynitrite. Sulfur free radicals may take the form of GS., which are generated from glutathione (GSH), hydrated sulfur dioxide or sulfur trioxide anion radicals (($.)SO(3)(-)$). Increased levels of oxygen, nitrogen or sulfur-based free radicals can cause damage to virtually all cellular components, including membranes, DNA, lipid bilayers, and proteins, which are components of all cell types.

Polyphenolic compounds have external antioxidant activities that can reduce the effects of free radicals, thus blocking tissue damage and clinical deficits. Internally, due to the ability of polyphenols to increase intracellular GSH as a mechanism of action, they can also reduce or attenuate free radical damage. In addition, many polyhenolic compounds have anti-excitotoxic effects (i.e.: the ability to counteract glutamate-induced damage on cells). Glutamate toxicity is one of the primary initiators of the ischemic cascade. Since polyphenols can block this deleterious action, they can act as neuroprotective compounds. These activities of polyphenols can be applied to a variety of diseases such as embolic stroke, Ischemic stroke, Hemorrhagic stroke, Ischemic heart conditions (patients undergoing heart bypass surgery, heart valve replacement) and Ischemia related spinal cord injury.

The polyphenol compound(s) can also be used for the treatment of diabetes and symptoms thereof, multiple sclerosis (MS) and symptoms thereof, dementia (Alzheimer's and non-Alzheimer's) and symptoms thereof, traumatic brain injury and symptoms thereof, and spinal cord injury and symptoms thereof. The compound(s) can also be used to treat patients at risk for any of these conditions.

The complications of diabetes are the major cause of both morbidity and mortality in patients with the disease. Chronic hyperglycemia is thought to be a major cause of these complications and the downstream consequences of hyperglycemia include multiple pathophysiological processes including protein glycation, reactive oxygen species (ROS) production and inflammation. Using a genetic model of type 1 diabetes, the Akita mouse, we recently showed that fisetin reduces two major complications of diabetes (Maher et al. PLoS One 6:e21226, 2011). Although fisetin had no effect on the elevation of blood sugar, it reduced kidney hypertrophy and albuminuria and maintained normal levels of locomotion in the open field test. This correlated with a reduction in proteins glycated by MG in the blood, kidney and brain of fisetin-treated animals along with an increase in glyoxalase 1 enzyme activity and an elevation in the expression of the rate-limiting enzyme for the synthesis of glutathione, a co-factor for glyoxalase 1. The expression of the receptor for advanced glycation end products (RAGE), serum amyloid A and serum C-reactive protein, markers of protein oxidation, glycation and inflammation, were also increased in diabetic Akita mice and reduced by fisetin. It is concluded that fisetin lowers the elevation of MG-protein glycation that is associated with diabetes and ameliorates multiple complications of the disease. Therefore, fisetin or a synthetic derivative may have potential therapeutic use for the treatment of diabetic complications. Accordingly, the invention provides methods of treating, reducing, mitigating, preventing diabetes, or one or more sequelae or symptoms thereof.

Multiple sclerosis (MS) is a complex, chronic inflammatory and demyelinating disease of the central nervous system (CNS). Its precise cause is unclear and its pathogenesis in incompletely understood. Chronic disability in multiple sclerosis (MS) is due to neuronal degeneration which is only incompletely amenable to immunomodulatory therapy. The mechanisms remain elusive, but there is accumulating evidence that oxidative stress may play a key role. Dimethyl-fumarate (DMF) is a promising novel oral therapeutic which reduces disease activity and progression in patients with relapsing-remitting multiple sclerosis. These effects are presumed to originate from both immunomodulatory and neuroprotective mechanisms. We recently showed that the protective effects of DMF are mediated by a combination of its ability to upregulate glutathione metabolism and its anti-inflammatory activity (Albrecht et al. J. Neuroinflammation 9:163, 2012). These two properties are shared by fisetin and a number of the fisetin derivatives suggesting that these compounds have the potential to be effective in the treatment of MS. Furthermore, compounds closely related to fisetin such as the flavonoid luteolin have shown some efficacy in animal models of MS (Theoharides, J. Neuroinflammation 6:29, 2009). Accordingly, the invention provides methods of treating, reducing, mitigating, preventing MS, or one or more sequelae or symptoms thereof.

Dementia is a progressive decline in cognitive function resulting in impairments in memory, thinking, language and judgment and alterations in behavior. There are many different types of dementia. In addition to Alzheimer's disease (AD), other common forms include vascular dementia, frontotemporal lobe dementia, semantic dementia and dementia with Lewy bodies. Fisetin is effective in multiple cell-based models that mimic many of the factors that contribute to the loss of brain function in AD as well as other dementias such as decreases in neurotrophic factors and increases in oxidative stress, protein aggregation and inflammation Importantly, fisetin is able both to prevent memory loss and to restore memory in mouse models of AD. Together, these results suggest that fisetin and fisetin derivatives could be effective against other types of dementia, especially as many dementias are associated with increased age and fisetin is effective at reducing age-related changes in nerve cell function both in cell culture models and in animals. Accordingly, the invention provides methods of treating, reducing, mitigating, preventing diabetes, or one or more sequelae or symptoms thereof.

Traumatic brain injury (TBI) is a leading cause of death and disability in civilian and military individuals aged 45 years and younger. TBI results in cognitive deficits in humans that can be reproduced in animal models. There are no effective treatments to reduce the consequences of TBI. TBI is associated with decreases in neurotrophic factors as well as molecules involved in synaptic plasticity and neuronal signaling and increases in oxidative stress. Fisetin is effective in multiple cell-based models that mimic many of the factors that contribute to the impairment of brain function in TBI. Furthermore, it is able to enhance synaptic plasticity and neuronal signaling in animals. Thus, it is likely that fisetin and fisetin derivatives could be effective in reducing the impact of TBI in humans.

In some embodiments, the subject has experienced an ischemic event. The ischemia treated by the methods of the present invention may occur in a variety of ways. In various embodiments, the ischemia may occur during a vascular occlusion in the body. The vascular occlusion may be caused by a variety of conditions, including, but not limited to extramural compression, arterial spasm, diseases of the vessel wall, thrombosis, embolism, and blood clot. In various embodiments, the ischemia can occur during or as a result of a stroke. In other embodiments, the ischemia can occur during or as a result of a cardiac event; such as, an arrhythmia or heart attack. In other embodiments, the ischemia can occur during cardiovascular surgery. In other embodiments, the ischemia can occur during or as a result of traumatic brain injury. In particular embodiments, subjects with acute ischemic stroke are treated by the methods of the present invention. Accordingly, the invention provides methods of treating, reducing, mitigating, preventing traumatic brain injury, or one or more sequelae or symptoms thereof.

In some embodiments, the subject is at risk of experiencing an ischemic event. As discussed above, the polyphenol compound(s) can be administered to a subject before, during or after major surgery, for example, cardiovascular surgery, to prevent or mitigate the occurrence of ischemia.

4. Compounds for Use in Treating and Preventing Ischemia

Various embodiments of the present invention provide for polyphenol analogs. In various embodiments, the polyphenol analogs are derived from chlorogenic acid, Fisetin, Baicalein or combinations thereof. The polyphenol analogs are not chlorogenic acid, Fisetin, or Baicalein themselves, however. In various embodiments, the polyphenol analogs structurally comprise a flavonol, a quinoline or a cinnamate. In various embodiments, the polyphenol analogs structurally comprise a flavonol or a quinolone.

Functionally, polyphenol analogs of interest can function as neuroprotective compounds and can be administered to a subject for the treatment and prevention of ischemia and symptoms associated with ischemia. The compounds provided herein provide improved neuroprotective activity in comparison to the parent compounds, i.e., in comparison to chlorogenic acid, Fisetin or Baicalein. The polyphenol analogs described herein can provide equivalent neuroprotective effects in comparison to the parent compounds at low doses, for example, at a dose that is about 75%, 50%, 25%, or less, of the dose of the parent compound required to achieve an equivalent neuroprotective effect. In various embodiments, the polyphenol analogs described herein inhibit MMP-9 (e.g., like chlorogenic acid). In some embodiments the polyphenol analogs described herein have anti-inflammatory and/or anti-oxidant properties. For example, like other flavonoid compounds, the polyphenol analogs described herein can protect nerve cells from oxidative stress, e.g., by preventing the accumulation of reactive oxygen species (ROS), blocking the early loss of cellular glutathione (GSH), and/or the late influx of $Ca^{+2}$ into cells. In some embodiments, the polyphenol analogs possess neurotrophic activities and can promote the development, maintenance and regeneration of nerve cells, including induction or promotion of neurite outgrowth (e.g., like Fisetin). In some embodiments, the polyphenol analogs can inhibit 12-LOX, scavenge free radical, and/or inhibit xanthine oxidase (e.g., like Baicalein). Preferred polyphenol analogs have the ability to penetrate and cross the blood-brain-barrier.

Structurally, in various embodiments, the compounds can comprise a structure of any one of Formulae I, IIA, IIB, IIIA, IIIB, IIIC, IIID, IIIE, IIIF, IIIG, IIIH, and/or IIIJ, as described herein, wherein the compound is not Fisetin, Baicalein, PM-001, PM-002, PM-003, PM-004, PM-008 and/or PM-014. In various embodiments, the compounds can comprise a structure of any one of Formulae IVA, IVB, IVC, IVD, IVE, IVF, IVG, IVH, IVJ, as described herein, wherein the compound is not chlorogenic acid.

In various embodiments, the polyphenol analog is
4-methoxy-2-(3,4-dihydroxyphenyl)quinoline (CMS-007);
4-ethoxy-2-(3,4-dihydroxyphenyl)quinoline (CMS-023);
4-isopropoxy-2-(3,4-dihydroxyphenyl)quinoline (CMS-024);
4-isopropoxy-2-(2,4-dihydroxyphenyl)quinoline (CMS-084);
4-cyclopentyloxy-2-(3,4-dihydroxyphenyl)quinoline (CMS-121);
4-methoxy-2-(3-hydroxy,4-methoxyphenyl)quinoline (CMS-001);
4-methoxy-2-(3,4-diethoxyphenyl)quinoline (CMS-004);
4-methoxy-2-(4-hydroxy,3-methoxyphenyl)quinoline (CMS-017);
4-methoxy-2-phenylquinoline (CMS-021);
4-methoxy-2-(4-hydroxyphenyl)quinoline (CMS-022);
4-methoxy-2-(2,4-dihydroxyphenyl)quinoline (CMS-083);
4-methoxy-2-(4-dimethylaminophenyl)quinoline (CMS-109);
4-methoxy-2-(4-(pyrrolidin-1-yl)phenyl)quinoline (CMS-110);
4-methoxy-2-(3-hydroxy-4-nitrophenyl)quinoline (CMS-111);
4-isopropoxy-2-(4-dimethylaminophenyl)quinoline (CMS-112); or
4-isopropoxy-2-(4-(pyrrolidin-1-yl)phenyl)quinoline (CMS-113).

In various embodiments, the polyphenol analog is
2-(3,4-dihydroxyphenyl)-3-hydroxy-6-methyl-4H-chromen-4-one (PM-010);
2-(3,4-dihydroxyphenyl)-6-ethyl-3-hydroxy-4H-chromen-4-one (PM-013);
2-(3,4-dihydroxyphenyl)-3-hydroxy-6-propyl-4H-chromen-4-one (PM-012);
2-(3,4-dihydroxyphenyl)-3-hydroxy-4H-benzo[h]chromen-4-one (CMS-040);
3-hydroxy-2-(4-hydroxy-3-methoxyphenyl)-6,7-dimethyl-4H-chromen-4-one (CMS-069);
2-(4-(benzyloxy)-3-methoxyphenyl)-3-hydroxy-4H-benzo[h]chromen-4-one (CMS-065);
2-(4-hydroxy-3-methoxyphenyl)-3-methyl-4H-benzo[h]chromen-4-one (CMS-072);
2-(4-(benzyloxy)-3-methoxyphenyl)-3-hydroxy-6,7-dimethyl-4H-chromen-4-one (CMS-059); 2-(4-hydroxy-3-methoxyphenyl)-6,7-dimethyl-4H-chromen-4-one (CMS-064);
2-(4-(chloromethyl)-3-methoxyphenyl)-3-hydroxy-6,7-dimethyl-4H-chromen-4-one (CMS-078);
3-hydroxy-2-(3-hydroxy-4-methoxyphenyl)-6,7-dimethyl-4H-chromen-4-one (CMS-092);
2-(4-(dimethylamino)phenyl)-3-hydroxy-6,7-dimethyl-4H-chromen-4-one (CMS-117);
3-hydroxy-2-(4-(pyrrolidin-1-yl)phenyl)-4H-benzo[h]chromen-4-one (CMS-114);
2-(4-(dimethylamino)phenyl)-3-hydroxy-4H-benzo[h]chromen-4-one (CMS-118);
3-hydroxy-2-(3-methoxy-4-(pyrrolidin-1-yl)phenyl)-4H-benzo[h]chromen-4-one (CMS-139);
3-hydroxy-2-(3-hydroxy-4-(pyrrolidin-1-yl)phenyl)-4H-benzo[h]chromen-4-one (CMS-140);
2-(3,4-diethoxyphenyl)-6,7-dimethyl-4H-chromen-4-one (CMS-018);
2-(3,4-diethoxyphenyl)-3-hydroxy-6,7-dimethyl-4H-chromen-4-one (CMS-025);
2-(3,4-dihydroxyphenyl)-3-hydroxy-6,7-dimethyl-4H-chromen-4-one (CMS-027);
2-(3,4-dihydroxyphenyl)-6,7-dimethyl-4H-chromen-4-one (CMS-028);
2-(3,4-diethoxyphenyl)-3-hydroxy-4H-benzo[h]chromen-4-one (CMS-036);
2-(3,4-diethoxyphenyl)-4H-benzo[h]chromen-4-one (CMS-038);
3-(3,4-dihydroxyphenyl)-2-hydroxy-1H-benzo[f]chromen-1-one (CMS-041);
2-(4-(benzyloxy)-3-methoxyphenyl)-6,7-dimethyl-4H-chromen-4-one (CMS-058);
2-(2,4-dihydroxyphenyl)-3-hydroxy-6,7-dimethyl-4H-chromen-4-one (CMS-093);
2-(2,4-dihydroxyphenyl)-6,7-dimethyl-4H-chromen-4-one (CMS-094);
3-hydroxy-2-(4-hydroxy-3-methoxyphenyl)-4H-benzo[h]chromen-4-one (CMS-070);
2-(4-(pyrrolidin-1-yl)phenyl)-4H-benzo[h]chromen-4-one (CMS-115);
6,7-dimethyl-2-(4-(pyrrolidin-1-yl)phenyl)-4H-chromen-4-one (CMS-116);
2-(4-(dimethylamino)phenyl)-6,7-dimethyl-4H-chromen-4-one (CMS-119);
2-(4-(dimethylamino)phenyl)-4H-benzo[h]chromen-4-one (CMS-120); or
3-hydroxy-6,7-dimethyl-2-(4-(pyrrolidin-1-yl)phenyl)-4H-chromen-4-one (CMS-122).

In various embodiments, the polyphenol analog is
(E)-3-(3,4-dihydroxyphenyl)-1-(2-hydroxy-4,5-dimethylphenyl)prop-2-en-1-one (CMS-011);
(E)-3-(3,4-dihydroxyphenyl)-1-(1-hydroxynaphthalen-2-yl)prop-2-en-1-one (CMS-034);
(E)-3-(3-hydroxy-4-(pyrrolidin-1-yl)phenyl)-1-(1-hydroxynaphthalen-2-yl)prop-2-en-1-one (CMS-138);
(E)-1-(1-hydroxynaphthalen-2-yl)-3-(3-methoxy-4-(pyrrolidin-1-yl)phenyl)prop-2-en-1-one (CMS-137);
(E)-3-(3,4-dihydroxyphenyl)-1-(2-hydroxy-5-isopropylphenyl)prop-2-en-1-one (CMS-129);
(E)-3-(3,4-diethoxyphenyl)-1-(2-hydroxy-4,5-dimethylphenyl)prop-2-en-1-one (CMS-013);
(E)-3-(3,4-diethoxyphenyl)-1-(1-hydroxynaphthalen-2-yl)prop-2-en-1-one (CMS-032);
(E)-3-(4-(benzyloxy)-3-methoxyphenyl)-1-(1-hydroxynaphthalen-2-yl)prop-2-en-1-one (CMS-063);
(E)-3-(3-(benzyloxy)-4-methoxyphenyl)-1-(2-hydroxy-4,5-dimethylphenyl)prop-2-en-1-one (CMS-086);
(E)-3-(2,4-dihydroxyphenyl)-1-(2-hydroxy-4,5-dimethylphenyl)prop-2-en-1-one (CMS-087); or
(E)-1-(2-hydroxy-4,5-dimethylphenyl)-3-(3-hydroxy-4-methoxyphenyl)prop-2-en-1-one (CMS-088).

In various embodiments, the polyphenol analog is selected from the polyphenol compounds provided in Table 1, Table 2, Table 3, Table 4, Table 6, Table 7 and/or Table 8.

In various embodiments, the polyphenol analog is selected from the group consisting of PM-010, PM-013, PM-012, CMS-007, CMS-011, CMS-023, CMS-024, CMS-034, CMS-040, CMS-059, CMS-069, and combinations thereof (i.e., selected from the compounds listed in Table 6). In various embodiments, the polyphenol analog is selected from the group consisting of CMS-034, CMS-040, CMS-065, CMS-072, PM-010, PM-013, PM-012, CMS-011, CMS-059, CMS-064, CMS-069, CMS-078, CMS-092, CMS-007, CMS-023, CMS-024, CMS-084, and combinations thereof (i.e., selected from the compounds listed in Table 7). In various embodiments, the polyphenol analog is selected from the group consisting of CMS-034, CMS-092, CMS-114, CMS-117, CMS-118, CMS-121, CMS-129, CMS-137, CMS-138, CMS-139, CMS-140, and combinations thereof (i.e., selected from the compounds listed in Table 8). In various embodiments, the polyphenol analog is selected from the group consisting of CMS-007, CMS-011, CMS-023, CMS-024, CMS-034, CMS-040, CMS-069 and combinations thereof. In other embodiments, the polyphenol analog is selected from the group consisting of CMS-023, CMS-024, CMS-040, CMS-069 and combinations thereof. In some embodiments, the polyphenol analog is CMS-023.

In various embodiments, Fisetin, Baicalein, chlorogenic acid, PM-001, PM-002, PM-003, PM-004, PM-008 and PM-014 are expressly excluded, e.g., from the claimed compositions and from use in the present methods.

5. Screening Assays for Identification of Polyphenol Compounds Useful to Treat and Prevent Ischemia Polyphenol analogs of interest for their neuroprotective properties and their use in treating, preventing and/or mitigating one or more symptoms of ischemia can be identified by testing compounds in in vitro and/or in vivo screening assays.

Numerous in vitro assays are known in the art and find use. Test compounds can be screened for their ability to inhibit nerve cell death one or more neurotoxicity paradigms, including without limitation, trophic factor withdrawal (TFW), excitotoxicity, glucose starvation, and chemically-induced ischemia. For example, the compounds can be contacted with hippocampal cells cultured in vitro in the presence of iodoacetic acid (IAA), an irreversible inhibitor of glyceraldehyde 3-phosphate dehydrogenase (G3PDH), in an established in vitro stroke model. Compounds of interest preserve the survival of at least 80% of the cultured hippocampal cells in the presence of IAA. The neuroprotective properties of compound of interest can also be screened in an in vitro excitotoxicity assay. Such in vitro neuron excitotoxicity assays are known in the art (see, e.g., Ishige, et al., *Free Radic Biol Med*, (2001) 30(4): p. 433-46). Compounds of interest preserve the survival of at least 35% of primary cultured neurons in the presence of glutamate. In vitro assays for determining neuronal cell survival when subjected to trophic factor withdrawal are known in the art and described, e.g., in Abe, *Japan J. Pharmacol.*, (1990) 53: p. 221-227. Cell survival can be measured using any method known in the art, including, e.g., MTT (3-(4,5-dimethylthiazol-2-yl)-2,5-diphenyltetrazolium bromide) assays, annexin assays, differential staining cytotoxicity (DiSC) assays, ATP assays to determine the loss of cellular ATP, fluorescein diacetate assays, which measure the loss of cell membrane esterase activity and cell membrane integrity, and propidium iodide assays.

The ability of polyphenol analogs to treat, prevent and/or mitigate one or more symptoms of stroke can also be evaluated in in vivo assays. Such assays are known in the art and find use. One applicable in vivo screening assay is the rabbit clot embolic stroke model, discussed, e.g., in Lapchak, et al., *Stroke* (2002) 33(9):2279-84 and Lapchak, *Exp Neurol*. (2007) 205(2):407-13. The rabbit small clot embolic stroke model (RSCEM) and rabbit large clot embolic stroke model (RLCEM) can be used to determine the potential neuroprotective properties and safety profile of test polyphenol analogs after an embolic stroke. Rabbits are embolized by injecting small blood clots (RSCEM) or large blood clots (RLCEM) into the cerebral circulation. Behavioral analysis is conducted 24 hours later, allowing for determination of the effective stroke dose (ES50) or clot amount (milligrams) that produces severe neurological deficits in 50% of rabbits. A drug is considered neuroprotective if it increases the ES50 compared with the vehicle-treated control group.

Compounds determined to be neuroprotective in in vitro and/or in vivo assays can be further tested for their appropriateness for administration to a subject, e.g., for mutagenicity, cytotoxicity and ability to penetrate and cross the blood brain barrier. Such assays are well known in the art and find use. For example, the mutagenic properties of a compound can be evaluated using the Ames mutagenicity assay (see, e.g., Mortelmans, et al., *Mutat. Res.* (2000) 455(1-2): 29-60), cytotoxity can be determined using cytochrome P450 assays and Blood Brain Barrier (BBB) penetration can be determined using a MDCK cell assay (see, e.g., Wang, et al., *Intl. J. Pharmaceutics* (2005) 288(2): 349-359 and Rubin, et al, *J. Cell Biol* (1991) 115(6):1725-35). Compounds of interest are not mutagenic in the Ames mutagenicity assay at a concentration less than 10 µM; have an $IC_{50}$ for CYP450 inhibition at a concentration greater than 10 µM; and have a moderate to high potential to penetrate and cross the blood-brain-barrier. The potential for BBB penetration is considered high if the efflux ration for transport into the brain or central nervous system (CNS), Papp A→B is equal to or greater than $3.0 \times 10^{-6}$ cm/s and efflux out of the brain or CNS is less than 3.0, as measured in the MDCK cell assay. The potential for BBB penetration is considered moderate if the efflux ration for transport into the brain or central nervous system (CNS), Papp A→B is equal to or greater than $3.0 \times 10^{-6}$ cm/s and 10>efflux≥$3.0 \times 10^1$ cm/s, as measured in the MDCK cell assay.

Compounds determined to be neuroprotective, and to have desired properties for administration to a subject (low or no mutagenicity, low or no cytochrome P450 cytotoxicity and moderate to high ability to penetrate and cross the blood-brain-barrier) can be further tested for cytotoxicity. Any cytotoxicity assays known in the art can be used. In various embodiments, compounds that show promise can be further subjected to a CeeTox™ panel, to determine a $C_{tox}$ ranking.

CeeTox™ quantitative measures can include one or more of the following:
(1) Membrane Integrity (GST or Adenylate Kinase leakage)
(2) Mitochondrial Function measuring MTT and ATP levels
(3) Cell Proliferation, e.g., using propidium iodide
(4) Oxidative Stress measuring both GSH and 8-isoprostane
(5) Apoptosis measuring caspase 3 activation
(6) Pgp interaction
(7) Solubility; and
(8) Microsomal metabolic stability The use of CeeTox™ quantitative measures is described, e.g., in McKim, *Comb Chem High Throughput Screen.* (2010) 13(2):188-206; McKim, et al., *Cutan Ocul Toxicol.* (2010) 29(3):171-92; and Lapchak and McKim, *Transl Stroke Res.* (2011) 2(1):51-59. Based upon a CeeTox™ algorithm, results from the CeeTox™ Panel of the first 7 assays described above can be used to assign a cytotoxicity value and determine relative cytotoxic potential of the polyphenol compound. CeeTox™ quantitative measures can be used to identify potential subcellular targets and mechanisms of toxicity, and to provide an estimated concentration (the $C_{tox}$ value) where toxicity would be expected to occur in a rat 14-day in vivo repeat dose study.

The microsomal metabolic stability assay (i.e., assay 8, above) can be conducted to determine the stability of the drug candidates and to help with compound prioritization. Desirable polyphenol compounds will demonstrate a probability of in vivo effects and a Ctox ranking (µM) of greater than 21 µM, preferably greater than 51 µM.

6. Formulation and Administration a. Formulation

In various embodiments, the present invention provides pharmaceutical compositions including a pharmaceutically acceptable excipient along with a therapeutically effective amount of the polyphenol compound(s) of the present invention. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Transdermal" administration may be accomplished using a topical cream or ointment or by means of a transdermal patch. "Parenteral" refers to a route of administration that is generally associated with injection, including intraorbital, infusion, intraarterial, intracarotid, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. In some embodiments, the compounds are administered by an appropriate route, for example, orally, parenterally, (intravenously (IV), intramuscularly (IM), depo-IM, subcutaneously (SQ), and depo-SQ), sublingually, intranasally (inhalation), intrathecally, topically, ionophoretically or rectally. Preferably, the compounds are administered by a route such that the compounds cross the blood-brain-barrier, e.g., for delivery to cerebral tissue. Dosage forms known to those of skill in the art are suitable for delivery of the compound.

Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the parenteral route, the compositions may be in the form of solutions or suspensions for infusion or for injection. Via the topical route, the pharmaceutical compositions based on compounds according to the invention may be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication. Via the ocular route, they may be in the form of eye drops.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

Compositions are provided that contain therapeutically effective amounts of the polyphenol. The compounds are preferably formulated into suitable pharmaceutical preparations such as tablets, capsules, or elixirs for oral administration or in sterile solutions or suspensions for parenteral administration. Typically the compounds described above are formulated into pharmaceutical compositions using techniques and procedures well known in the art.

The compounds can be administered in the "native" form or, if desired, in the form of salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

Methods of formulating such derivatives are known to those of skill in the art. For example, the disulfide salts of a number of delivery agents are described in PCT Publication WO 2000/059863 which is incorporated herein by reference. Similarly, acid salts of therapeutic peptides, peptoids, or other mimetics, and can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the active agents herein include halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. In certain embodiments basic salts include alkali metal salts, e.g., the sodium salt, and copper salts.

For the preparation of salt forms of basic drugs, the pKa of the counterion is preferably at least about 2 pH lower than the pKa of the drug. Similarly, for the preparation of salt forms of acidic drugs, the pKa of the counterion is preferably at least about 2 pH higher than the pKa of the drug. This permits the counterion to bring the solution's pH to a level lower than the pHmax to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (i.e., break down into the individual entities of drug and counterion) in an aqueous environment.

Preferably, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

In various embodiments preparation of esters typically involves functionalization of hydroxyl and/or carboxyl groups that are present within the molecular structure of the active agent. In certain embodiments, the esters are typically acyl-substituted derivatives of free alcohol groups, i.e., moieties that are derived from carboxylic acids of the formula RCOOH where R is alkyl, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine About 1 mg to about 1000 mg of one or more of the compounds described herein or a physiologically acceptable salt or ester thereof is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions are preferably formulated in a unit dosage form, each dosage containing from about 1-1000 mg, 2-800 mg, 5-500 mg, 10-400 mg, 50-200 mg, e.g., about 5 mg, 10 mg, 15 mg, 20 mg, 25 mg, 30 mg, 35 mg, 40 mg, 45 mg, 50 mg, 60 mg, 70 mg, 80 mg, 90 mg, 100 mg, 200 mg, 300 mg, 400 mg, 500 mg, 600 mg, 700 mg, 800 mg, 900 mg or 1000 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

To prepare compositions, the compounds are mixed with a suitable pharmaceutically acceptable carrier. Upon mixing or addition of the compound(s), the resulting mixture may be a solution, suspension, emulsion, or the like. Liposomal suspensions may also be suitable as pharmaceutically acceptable carriers. These may be prepared according to methods known to those skilled in the art, e.g., involving milling, mixing, granulation, and compressing, when necessary, for tablet forms; or milling, mixing and filling for hard gelatin capsule forms. When a liquid carrier is used, the preparation can be in the form of a syrup, an elixir, an emulsion or an aqueous or non-aqueous suspension. Such a liquid formulation may be administered directly p.o. or filled into a soft gelatin capsule. The form of the resulting mixture depends upon a number of factors, including the intended mode of administration and the solubility of the compound in the selected carrier or vehicle. The effective concentration is sufficient for lessening or ameliorating at least one symptom of the disease, disorder, or condition treated and may be empirically determined.

Pharmaceutical carriers or vehicles suitable for administration of the compounds provided herein include any such carriers known to those skilled in the art to be suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

Where the compounds exhibit insufficient solubility, methods for solubilizing may be used. Such methods are known and include, but are not limited to, using cosolvents such as dimethylsulfoxide (DMSO), using surfactants such as Tween™, using a solubilizer such as Solutol® (ethylene oxide and 12-hydroxy stearic acid), and dissolution in aqueous sodium bicarbonate. Derivatives of the compounds, such as salts or prodrugs may also be used in formulating effective pharmaceutical compositions.

The concentration of the compound is effective for delivery of an amount upon administration that lessens or ameliorates at least one symptom of the disorder for which the compound is administered and/or that is effective in a prophylactic context. Typically, the compositions are formulated for single dosage (e.g., daily) administration.

The compound may be prepared with carriers that protect them against rapid elimination from the body, such as time-release formulations or coatings. Such carriers include controlled release formulations, such as, but not limited to, microencapsulated delivery systems. The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder. A therapeutically or prophylactically effective dose can be determined by first administering a low dose, and then incrementally increasing until a dose is reached that achieves the desired effect with minimal or no undesired side effects.

In various embodiments, the compound can be enclosed in multiple or single dose containers. The enclosed compounds and compositions can be provided in kits, for example, including component parts that can be assembled for use. For example, a compound inhibitor in lyophilized form and a suitable diluent may be provided as separated components for combination prior to use. A kit may include a compound inhibitor and a second therapeutic agent for co-administration. The inhibitor and second therapeutic agent may be provided as separate component parts. A kit may include a plurality of containers, each container holding one or more unit dose of the polyphenol compound(s). The containers are preferably adapted for the desired mode of administration, including, but not limited to tablets, gel capsules, sustained-release capsules, and the like for oral administration; depot products, pre-filled syringes, ampules, vials, and the like for parenteral administration; and patches, medipads, creams, and the like for topical administration.

The concentration and/or amount of active compound in the drug composition will depend on absorption, inactivation, and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound can be provided in a formulation that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

In various embodiments, the tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action.

Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

In various embodiments, the compounds are formulated for intravenous administration. When administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known for example, as described in U.S. Pat. No. 4,522,811. In some embodiments, the compounds are formulated in Solutol HS15 in saline, for example, using 70% Solutol HS15 and 30% saline as a vehicle for intravenous administration.

The active compounds may be prepared with carriers that protect the compound against rapid elimination from the body, such as time-release formulations or coatings.

Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

b. Administration and Dosing

Administering the polyphenol analog may be performed before, during or after ischemia occurs or the condition where ischemia occurs. For instance, in various embodiments, the polyphenol analog can be administered prior to a surgery (e.g., cardiovascular surgery) for beneficial effects (e.g., neuroprotective and/or neurotrophic effects); administration of the polyphenol analog can be continued during surgery; and administration of the polyphenol analog can be continued after surgery. In other embodiments, the polyphenol analog can be administered after a subject suffers a vascular occlusion. In particular embodiments, the vascular occlusion is a stroke. In various embodiments, the polyphenol analog can be administered 5, 10, 20, 30, 45, 60, 75, 90, 105, and/or 120 minutes after the vascular occlusion. In various embodiments, the polyphenol analog can be administered 2, 3, 4, 5 and/or 6 hours after the vascular occlusion. In various embodiments, the polyphenol analog can be administered up to 6 hours after the vascular occlusion. In various embodiments, the polyphenol analog may be administered up to 12 hours after the vascular occlusion. In various embodiments, the polyphenol analog may be administered up to 24 hours after the vascular occlusion.

In various embodiments, there may be an initial dose of the polyphenol analog administered to the subject followed by one or more maintenance doses of the polyphenol analog administered to the subject. In other embodiments, the polyphenol analog can be continuously administered to the subject.

In various embodiments, the polyphenol analogs can be administered by an appropriate route, for example, orally, parenterally (IV, IM, depo-IM, SQ, and depo-SQ), sublingually, intranasally (inhalation), intrathecally, topically, or rectally. Dosage forms known to those skilled in the art are suitable for delivery of polyphenol analogs.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see, e.g., *Remington: The Science and Practice of Pharmacy*, University of the Sciences in Philadelphia (Editor), 21$^{st}$ Edition, 2005, Lippincott Williams & Wilkins; and Sinko, *Martin's Physical Pharmacy and Pharmaceutical Sciences*, 6$^{th}$ Edition, 2010, Lippincott Williams & Wilkins.

Typical dosages of an effective polyphenol analog of the present invention can be in the as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied ischemic tissue, or the responses observed in the appropriate animal models.

In various embodiments, the polyphenol analogs may be administered enterally or parenterally. When administered orally, the polyphenol analogs can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, it is preferred that they be of the sustained release type so that the polyphenol analogs need to be administered only once or twice daily.

The oral dosage forms can be administered to the patient 1, 2, 3, or 4 times daily. It is preferred that the polyphenol analogs be administered either three or fewer times, more preferably once or twice daily. Hence, it is preferred that the polyphenol analogs be administered in oral dosage form. It is preferred that whatever oral dosage form is used, that it be designed so as to protect the polyphenol analogs from the acidic environment of the stomach. Enteric coated tablets are well known to those skilled in the art. In addition, capsules filled with small spheres each coated to protect from the acidic stomach, are also well known to those skilled in the art.

When administered orally, an administered amount therapeutically effective to inhibit symptoms of ischemia and/or prevent an ischemic event is from about 10 mg/day to about 1000 mg/day, for example, from about 20 mg/day to about 500 mg/day, for example, from about 50 mg/day to about 200 mg/day. In some embodiments, the subject is administered polyphenol analogs compound(s) at a dose of about 5.0 to about 200 mg/kg, for example, about 10.0 to about 100 mg/kg, for example, about 10 mg/kg, 15 mg/kg, 20 mg/kg, 50 mg/kg, 75 mg/kg, 100 mg/kg, 125 mg/kg, 150 mg/kg, 175 mg/kg or 200 mg/kg. It is understood that while a patient may be started at one dose, that dose may be varied (increased or decreased, as appropriate) over time as the patient's condition changes. Depending on outcome evaluations, higher doses may be used. For example, in certain embodiments, up to as much as 1000 mg/day can be administered, e.g., 200 mg/day, 300 mg/day, 400 mg/day, 500 mg/day, 600 mg/day, 700 mg/day, 800 mg/day, 900 mg/day or 1000 mg/day.

The polyphenol analogs may also be advantageously delivered in a nano crystal dispersion formulation. Preparation of such formulations is described, for example, in U.S. Pat. No. 5,145,684. Nano crystalline dispersions of HIV protease inhibitors and their method of use are described in U.S. Pat. No. 6,045,829. The nano crystalline formulations typically afford greater bioavailability of drug compounds.

In various embodiments, the polyphenol analogs can be administered parenterally, for example, by IV, IM, depo-IM, SC, or depo-SC. When administered parenterally, a therapeutically effective amount of about 5.0 to about 500 mg/day, preferably from about 10 to about 200 mg daily can be delivered. When a depot formulation is used for injection once a month or once every two weeks, the dose should be about 5.0 mg/day to about 500 mg/day, or a monthly dose of from about 10 mg to about 200 mg. In various embodiments, the parenteral dosage form can be a depo formulation.

In various embodiments, the polyphenol analogs can be administered sublingually. When given sublingually, the polyphenol analogs analog can be given one to four times daily in the amounts described above for parenteral administration.

In various embodiments, the polyphenol analogs can be administered intranasally. When given by this route, the appropriate dosage forms are a nasal spray or dry powder, as is known to those skilled in the art. The dosage of the polyphenol analogs for intranasal administration is the amount described above for parenteral administration.

In various embodiments, the polyphenol analogs can be administered intrathecally. When given by this route the appropriate dosage form can be a parenteral dosage form as is known to those skilled in the art. The dosage of the polyphenol analogs for intrathecal administration is the amount described above for parenteral administration.

In certain embodiments, the polyphenol analogs can be administered topically. When given by this route, the appropriate dosage form is a cream, ointment, or patch. When administered topically, the dosage is from about 5.0 mg/day to about 500 mg/day.

Because the amount that can be delivered by a patch is limited, two or more patches may be used. The number and size of the patch is not important, what is important is that a therapeutically effective amount of the polyphenol analogs be delivered as is known to those skilled in the art. The polyphenol analogs can be administered rectally by suppository as is known to those skilled in the art. When administered by suppository, the therapeutically effective amount is from about 5.0 mg to about 500 mg.

In various embodiments, the polyphenol analogs can be administered by implants as is known to those skilled in the art. When administering polyphenol analogs by implant, the therapeutically effective amount is the amount described above for depot administration.

It should be apparent to one skilled in the art that the exact dosage and frequency of administration will depend on the particular condition being treated, the severity of the condition being treated, the age, weight, general physical condition of the particular patient, and other medication the individual may be taking as is well known to administering physicians who are skilled in this art.

7. Combination Therapies

The polyphenol analogs described herein can be used in combination with currently employed therapeutic regimes for preventing, treating and ameliorating ischemia. In various embodiments, the polyphenol analogs can be co-administered with a regime of tissue plasminogen activator (tPA). Since optimal doses of rtPA do not eliminate brain damage, co-administration of one or more of the polyphenol analogs described herein can be beneficial to the subject, particularly to increase the treatment window for tPA (which is so short that many subjects do not benefit from its administration). Co-administration of one or more of the polyphenol analogs with tPA is of particular use to patients receiving care within 6 hours, e.g., within 5, 4, 3, 2, 1 hours, of an ischemic event. The tPA may be purified or recombinant Numerous recombinant versions of tPA are available for co-administration, including without limitation, alteplase, reteplase, tenecteplase (TNKase), and desmoteplase. In some embodiments, one or more of the polyphenol analogs are co-administered with a subtherapeutic dose of tPA.

In patients who have experienced or are at risk of experiencing cardioembolic stroke, the polyphenol analogs can be co-administered with a regime of an anticoagulant. Exemplary anticoagulants include aspirin, heparin, warfarin, and dabigatran.

In patients who have experienced or are at risk of experiencing carotid stenosis, the polyphenol analogs can be co-administered with a regime of an anti-platelet drug. The most frequently used anti-platelet medication is aspirin. An alternative to aspirin is the anti-platelet drug clopidogrel (Plavix). Some studies indicate that aspirin is most effective in combination with another anti-platelet drug. In some embodiments, the patient is prescribed a combination of low-dose aspirin and the anti-platelet drug dipyridamole (Aggrenox), to reduce blood clotting. Ticlopidine (Ticlid) is another anti-platelet medication that finds use. Patients having a moderately or severely narrowed neck (carotid) artery, may require or benefit from carotid endarterectomy. This preventive surgery clears carotid arteries of fatty deposits (atherosclerotic plaques) to prevent a first or subsequent strokes. In some embodiments, the patient may require or benefit from carotid angioplasty, or stenting. Carotid angioplasty involves using a balloon-like device to open a clogged artery and placing a small wire tube (stent) into the artery to keep it open.

In patients who have experienced or are at risk of experiencing atrial fibrillation, the polyphenol analogs can be co-administered with a regime of an anti-coagulant (to prevent stroke) and/or a pharmacological agent to achieve rate control. Exemplary anticoagulants include aspirin, heparin, warfarin, and dabigatran. Exemplary rate control drugs include beta blockers (e.g., metoprolol, atenolol, bisoprolol), non-dihydropyridine calcium channel blockers (e.g., diltiazem or verapamil), and cardiac glycosides (e.g., digoxin).

As appropriate, the polyphenol analogs also can be administered to patients receiving transcranial laser therapy or ultrasound.

8. Kits

The present invention is also directed to a kit to treat ischemia. The kits are useful for practicing the inventive method of treating, preventing and/or mitigating ischemia and providing neuroprotective effects. The kit is an assemblage of materials or components, including at least one of the polyphenol analogs described herein. Thus, in some embodiments the kit contains a composition including one or more polyphenol analogs of the present invention.

The exact nature of the components configured in the inventive kit depends on its intended purpose. For example, some embodiments are configured for the purpose of treating stroke patients or cardiovascular patients. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat ischemia. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing a polyphenol analog. The packaging material generally has an external label which indicates the contents and/or purpose of the kit and/or its components.

EXAMPLES

The following examples are offered to illustrate, but not to limit the claimed invention.

Example 1

Chlorogenic acid Improves Neurological Performance Following Embolic Strokes in Rabbits Either vehicle or bolus injections of chlorogenic acid were administered intravenously over 1 minute starting 5 minutes following embolization using a suspension of small-sized blood clots. In this series of studies, CGA was administered at 50 mg/kg [65]. Behavioral analysis was conducted at 24 hours following treatment, which allowed for the construction of quantal dose-response analysis curves. FIG. 1 shows a graphical representation of the raw data that is superimposed on the theoretical quantal analysis curves. For the superimposed graphs, normal animals are plotted on the y-axis at 0% and abnormal animals are plotted at 100%. The figure shows that there is positive correlation between the data (circles or triangles) and the statistically fitted quantal curve. Moreover, CGA increased the $P_{50}$ value (the clot dose that produces abnormality in 50% of a treatment group) compared to vehicle control. For a detailed discussion of the methods used to fit the quantal data to a sigmoidal curve, see Zivin and Waud [91]. The pharmacology of chlorogenic acid in the rabbit small clot embolic stroke model (RSCEM) has been published (Lapchak, *Exp Neurol.* 2007 205(2):407-13). In the manuscript, it is shown that CGA has a therapeutic window of 60 minutes in the RSCEM. FIG. 2 presents the therapeutic window data.

Example 2

Fisetin is Neuroprotective in vitro and in vivo

Figure 3:
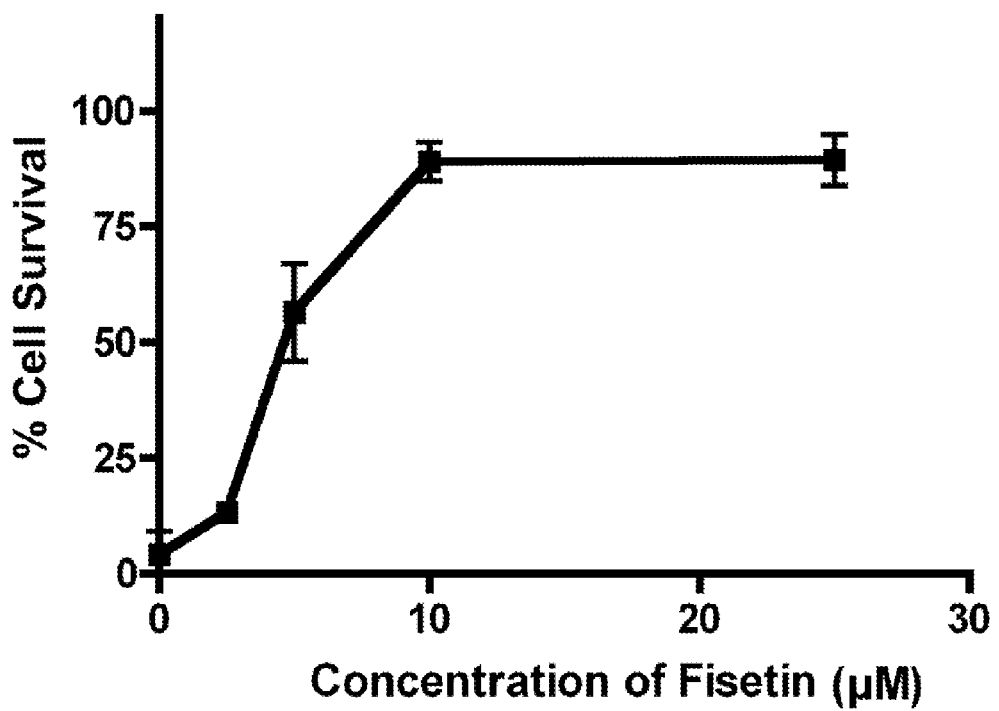
FIG. 3 illustrates the pharmacological effects of Fisetin on cultured HT22 mouse hippocampal cells. In this stroke in vitro assay, HT22 cells were treated with 20 µM iodoacetic acid (IAA) for 2 hr alone or in the presence of varying concentrations of Fisetin. At 24 hours, cell survival was measured using a standard MTT assay. Cell survival was also confirmed by light microscopy. In the absence of a neuroprotective, <95% of the cell population dies off within 24 hours. The graph shows that Fisetin is neuroprotective over the concentration range of 5-25 µM, increasing survival by greater than 85%.

For these studies, cultured HT22 mouse hippocampal cells were used as an in vitro stroke assay [80]. HT22 cells were treated with iodoacetic acid (IAA), an irreversible inhibitor of glyceraldehyde 3-phosphate dehydrogenase (G3PDH) for 2 hr alone or in the presence of varying concentrations of Fisetin. G3PDH is an enzyme of the glycolysis pathway, which catalyzes the synthesis of 1,3-bisphosphoglycerate, a "high energy" intermediate used for the synthesis of ATP. Cell survival was measured using a standard colorimetric MTT (3-(4,5-dimethylthiazol-2-yl)-2, 5-diphenyltetrazolium bromide) assay for cell survival MTT is a pale yellow substrate that is cleaved by living cells to yield a dark blue formazan product. This process requires active mitochondria, and even freshly dead cells do not cleave significant amounts of MTT. The graph (FIG. 3) shows that there is a dose-dependent effect of Fisetin on the survival of HT22 cells.

Using the RSCEM assay described above for CGA, the effects of Fisetin (50 mg/kg) on behavioral outcome measured 24 hours following embolization is tested.

Figure 4:
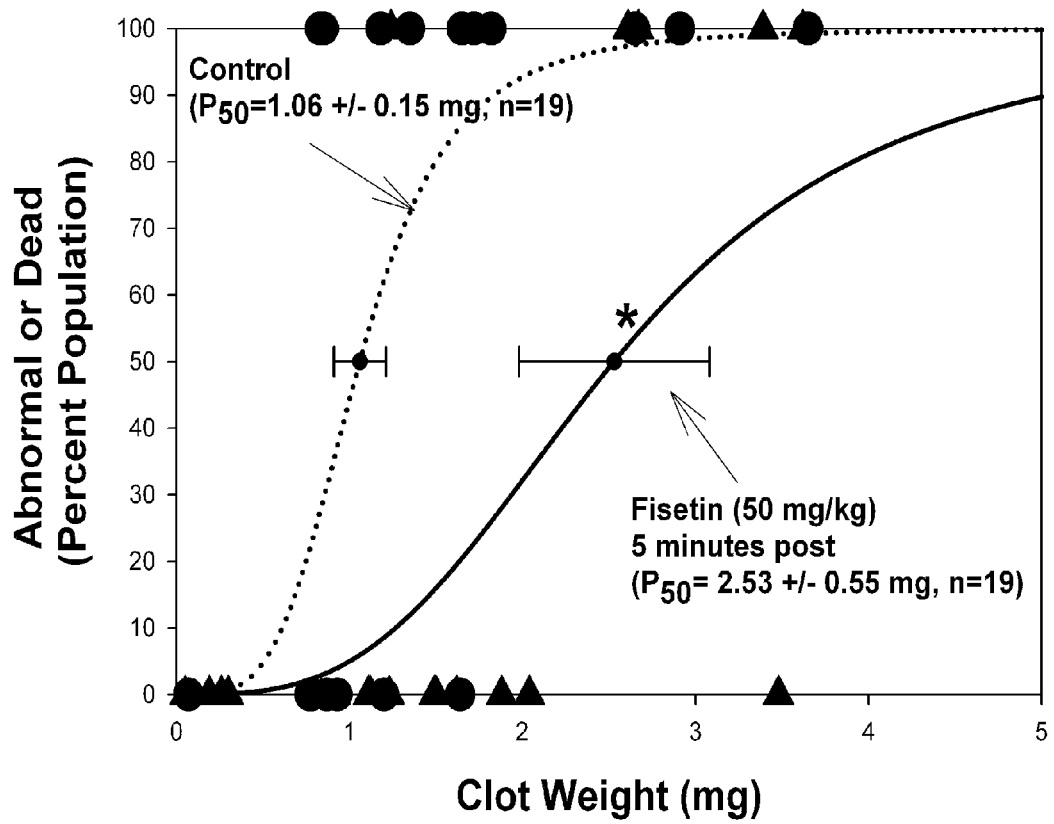
FIG. 4 illustrates behavioral improvement following Fisetin treatment in the rabbit small clot embolic stroke model (RSCEM). The control curve (dotted line) has a $P_{50}$ value of 1.06±0.15mg (n=19). Fisetin treatment (50 mg/kg intravenously (IV)) initiated 5 minutes following embolization increased the $P_{50}$ value to 2.53±0.55mg (n=19, *P<0.05) (dark solid line). The dark circles ● represent the raw data from the control group and the triangles ▲ represent the raw data for the Fisetin-treated group. A normal rabbit for a specific clot weight is represented by a symbol plotted at 0% on the y-axis, whereas an abnormal rabbit for a specific clot weight is represented by a symbol plotted at 100% on the y-axis.

FIG. 4 shows that Fisetin administration also increased behavioral function when the drug was given 5 minutes following embolization. The extent of the increase in $P_{50}$ produced by Fisetin is lower than that for CGA (see above), nevertheless, the increase is statistically significant from the vehicle control curve shown in the graph. The differences between these initial findings may simply be caused by dosing differences and may not reflect true differences in optimal neuroprotection capability.

The pharmacology of Fisetin and other flavonoids using NT22 cells and in the RSCEM has been published (Maher, et al., *Brain Res.* 2007,1173:117-25). In the manuscript, it is shown that Fisetin and Baicalein are effective neuroprotective agents in the HT22 cell assay and that Fisetin improves behavior following embolic strokes using the RSCEM.

Example 3

Neuroprotective Effects of the 12-LOX Inhibitor Baicalein in vitro

FIGS. 5A-5D show that Baicalein is able to inhibit nerve cell death in four additional neurotoxicity paradigms. These include trophic factor withdrawal (TFW), excitotoxicity, glucose starvation, and most importantly, in a chemical ischemia model. Baicalein dramatically promotes the survival of freshly plated, low-density cultured rat cortical neurons in serum-containing medium, an assay for trophic factor withdrawal [92] (FIG. 5A). Using a published excitotoxicity assay [53], Baicalein rescues about 35% of the cells (FIG. 5B).

Baicalein is also neuroprotective in glucose starvation assays [93], and these results using PC12 cells were duplicated. When these cells are starved for glucose, there is approximately 70% maximal survival in the presence of NGF. Baicalein promotes over 80% survival (FIG. 5C). Finally, Baicalein prevents cell death in a chemical ischemia model using the irreversible inhibitor of G3PDH, IAA as described above for Fisetin, even when added 2 hrs after the ischemic insult (FIG. 5D).

Figure 6:
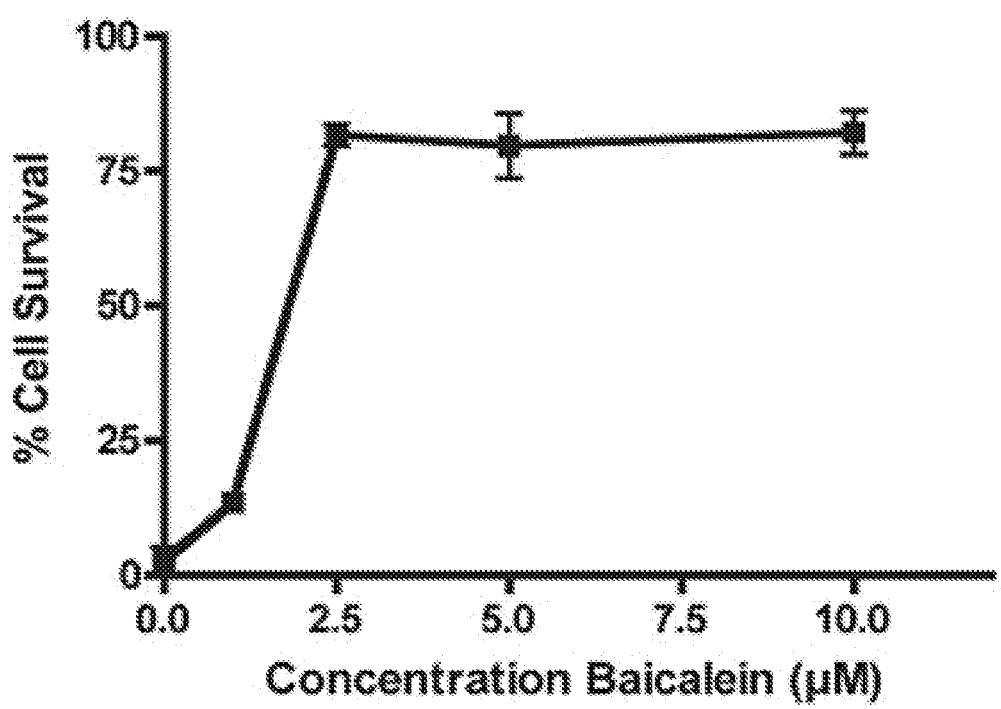
FIG. 6 depicts pharmacological effects of Baicalein on cultured HT22 mouse hippocampal cells. In the stroke in vitro assay, HT22 cells were treated with 20 µM iodoacetic acid (an irreversible inhibitor of G3PDH for 2 hr alone or in the presence of varying concentrations of Baicalein. At 24 hours, cell survival was measured using a standard MTT assay. Cell survival was also confirmed by light microscopy. In the absence of a neuroprotective, >95% of the cell population dies off within 24 hours. The graph shows that Baicalein is neuroprotective over the concentration range of 2.5-10 µM, where the drug increased survival by greater than 80%.
Figure 7:
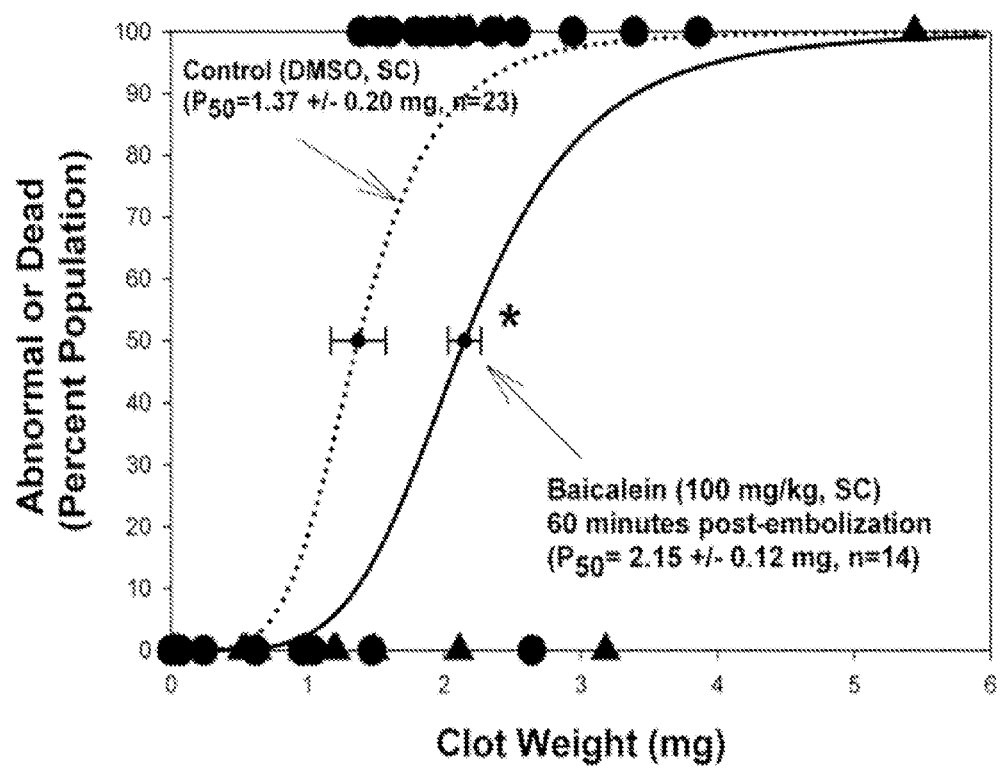
FIG. 7 illustrates behavioral improvement following Baicalein treatment given 60 minutes post-embolization in the rabbit small clot embolic stroke model (RSCEM). The control curve (dotted line) has a $P_{50}$ value of 1.37±0.20 mg (n=21). Baicalein treatment (100 mg/kg subcutaneously (SC)) initiated 60 minutes following embolization increased the $P_{50}$ value to 2.15±0.12 mg (n=14, *P<0.05) (dark solid line). The dark circles ● represent the raw data from the control group and the triangles ▲ represent the raw data for the Baicalein-treated group. A normal rabbit for a specific clot weight is represented by a symbol plotted at 0% on the y-axis, whereas an abnormal rabbit for a specific clot weight is represented by a symbol plotted at 100% on the y-axis.

FIG. 6 shows that Baicalein is also effective at promoting cell survival of HT22 hippocampal cells in vitro. The effective doses for Baicalein-induced cell survival are lower than those required for Fisetin-induced cell survival using the same culture model. FIG. 7 shows that Baicalein significantly (p<0.05) improved stroke-induced behavioral deficits and increased the P50 value when administered 60 minutes following embolization The Baicalein-induced improvement in behavior is directly correlated with an increase in the number of animals which are behaviorally "normal" as shown on the y-axis plotted at 0. The pharmacology of Baicalein in the RSCEM has been published (Lapchak, et al., *Neuroscience.* 2007, 150(3):585-91). In the manuscript, it is shown show that the compound has a minimum therapeutic window of 60 minutes in the RSCEM.

Results show that the lead compounds are neuroprotective in HT22 cells in vitro stroke model, the primary in vitro screen for this program or in vivo using the RSCEM, the primary in vivo drug development screen. Fisetin and Baicalein promotes cell survival in vitro using hippocampal cells. Baicalein is also effective at increasing cell survival using 4 different in vitro paradigms, including excitotoxicity. CGA, Fisetin and Baicalein are also effective at reducing stroke-induced behavioral deficits or improving behavior in the rabbit small clot embolic stroke model (Lapchak, *Exp Neurol.* 2007 205(2):407-13 and Maher, et al., *Brain Res.* 2007,1173:117-25). Both CGA and Baicalein are effective at improving behavior when administered 1 hour following embolization, but neither improve behavior when administered 3 hours following embolization.

Overall, the results show that the three compound classes have significant efficacy in vitro and in vivo. The three parent compounds described above were used to form the basis for chemical optimization using a focused diversity library approach that covers various substitution positions on the parent backbone (scaffold) of CGA, Fisetin and Baicalein.

Example 4

Diversity Oriented Synthesis of Libraries

The following example outlines a chemical synthesis program to synthesize small libraries of 30-40 compounds based upon Fisetin, Baicalein and CGA. Resulting novel compounds were screened using the in vitro stroke HT22 cell assay so that high efficacy compounds can be identified. For a compound to be considered for advancement to the in vivo RSCEM screening process, it should have an $EC_{50}$ value in the range of 10-100 nM. The compounds with the lowest $EC_{50}$ values are advanced to the RSCEM for study.

Example 5

Illustrative Synthetic Scheme of Flavones

Figure 8:
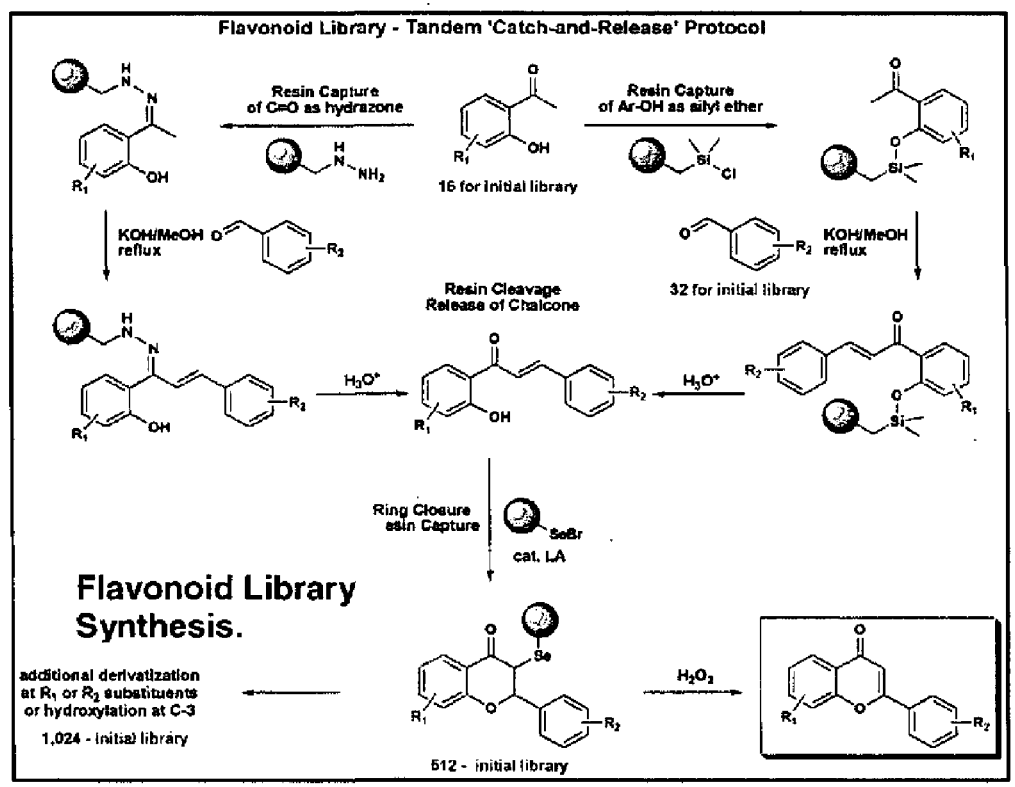
FIG. 8 illustrates a method of flavonoid library synthesis.
Figure 16:
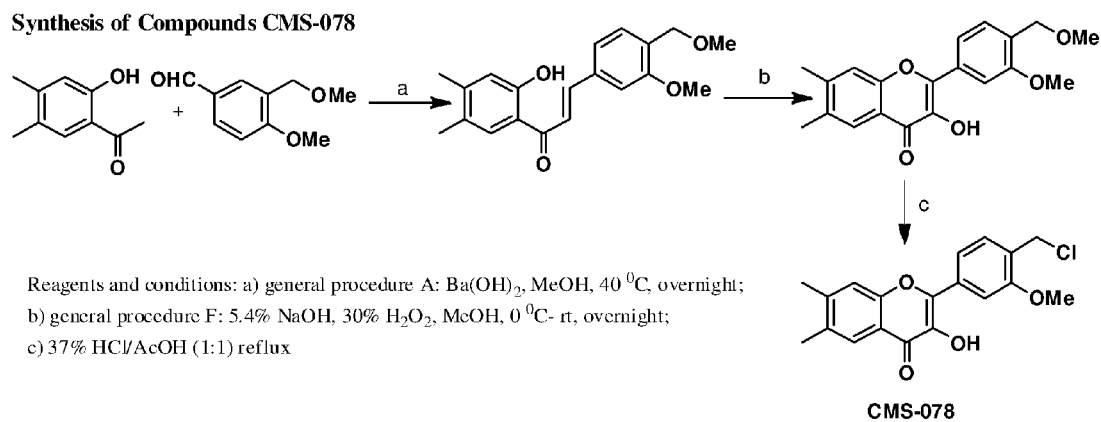
FIG. 16 provides an illustrative synthetic scheme for compound CMS-078.
Figure 17:
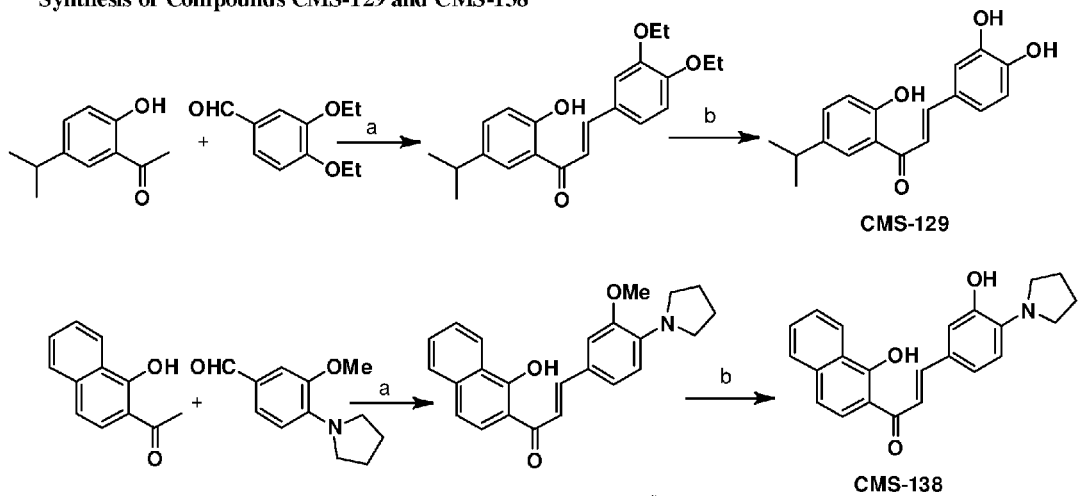
FIG. 17 provides an illustrative synthetic scheme for compounds CMS-129 and CMS-138.

To synthesize flavones, a tandem 'catch and release' protocol via solid-phase synthesis that utilizes simple building blocks (FIG. 8) was employed. These building blocks include 2-hydroxyacetone phenones, phenols (for conversion to corresponding acetophenones), and benzaldehydes.

A chemical biology approach was used to develop a small and focused diversity oriented synthetic library around the requisite 5, 6 and 7-hydroxyl groups of Baicalein and the 3, 3'and 4'-hydroxyl groups of Fisetin. These groups impart activity to both compounds as determined by structure-activity relationships in multiple assays [see, for example, [101] and Maher, *Free Radical Research*, (2006) 40(10): 1105-1111). The libraries were made according to the principles of Diversity Oriented Synthesis (DOS,) and seek to improve upon the pharmacological properties of the flavones with a goal of an $EC_{50}$ between 10-100 nM in vitro [102]. The synthetic protocol shown in FIG. 8 incorporates these building blocks into two sub-libraries that represent the products derived from acetophenones and benzaldehydes. This leaves the C-3 position to be combinatorialized so that the 5, 6 and 7-trihydroxyl groups of Baicalein and 3, 3' and 4'-hydroxyl groups of Fisetin are maintained.

This synthetic scheme draws from several known flavonoid synthesis methodologies [83, 103], and incorporating advantages from each. Beginning with a 2-hydroxy-acetophenone, this building block was captured on a solid-support (a polystyrene-based resin) using a linker, e.g., a silylether linkage (right arrow) or hydrazone linkage (left arrow). Both of these resin-capture methods are well characterized for parallel and combinatorial libraries [104], although other linkers known to one of ordinary skill in the art would suffice. The silylether pathway has significant advantages during the preparation of some derivatives, but the hydrazone pathway is a preferred method for the synthesis of the derivatives that maintain the flavone hydroxyl groups of the natural products. Hydrazone formation is selective for the acetophenone moiety, because this is the only carbonyl with which the hydrazine-resin can form a Schiff base [105]. The silylether protocol as depicted is designed to selectively silylate the 2-hydroxy position. Subsequent Claisen-Schmidt condensation (under basic conditions) yields the resin-bound chalcones [106]. Mild acidic release of the supported chalcones is followed by selenium-mediated cyclative recapture with selenium bromide resin [83].

By employing this tandem capture-react-release-recapture process, enrichment and purity of the final products without the need for post-synthesis purification is achieved. Final release was afforded via treatment with hydrogen peroxide for the C-3=H derivatives, and further oxidation of these products generates the C-3=OH derivative in parallel [107]. These syntheses were carried out on a 0.05 mmol scale, yielding 10-15 mg of each compound.

The small diversity libraries based upon the Fisetin and Baicalein scaffolds employed building blocks with additional functional groups to improve biological activity in our assays. Substitutions such as F, Cl, OMe, OAc, NHMe, NHAc, CN, $CF_3$, and OH were explored, in the nonhydroxylated positions of Fisetin and Baicalein. Since F can participate in hydrogen bonding [108] some F for OH substitutions in the 5, 6 or 7 hydroxyls of Baicalein and 3, 7, 3', or 4'-hydroxyls of Fisetin were also included. Various constraints, filters and diversity metrics can be used to select the library as outlined in [109] to reduce the number of derivatives to between 30 and 40 each for Baicalein and Fisetin.

Example 6

Illustrative Synthetic Scheme of CGA Derivatives

The efficient synthesis of CGA (FIG. 9A) (65% yield) from caffeic (FIG. 9B) and quinic (FIG. 9C) acids has been described [110]. This synthetic scheme allows for the synthesis of a wide variety of CGA derivatives based upon the commercial availability of substituted cinnamic acid (FIGS. 9D and 9E) and cyclohexene carboxylic acids (FIGS. 9F and 9G).

Initially, substituents on the caffeic acid half of chlorogenic acid were varied. 2 or 3-monohydroxy cinnamic, 2, 3 or 4-methyl cinnamic, 2, 3 or 4-nitro cinnamic, 2,3-chloro or 2,3,4-fluoro, or 4-amino cinnamic acids (FIG. 9E) were used as the starting materials. These were reacted with the protected form of quinic acid as described by Sefkow [110] to generate a first class of chlorogenic acid derivatives. To synthesize the chlorogenic acid derivatives based upon the quinic acid portion of the molecule, and to maintain the carboxylic acid group, a variety of commercially available substituted cyclohexene carboxylic acids (FIGS. 9F and 9G), were bis-hydroxylated at the olefinic bonds to generate the dihydroxy cyclohexane carboxylic acid (FIGS. 9H and 9I). Dihydroxy cyclohexanes (FIGS. 9H and 9I) were used as starting materials. Published hydroxy group protection procedures [110] were used to synthesize the quinic acid substituted derivatives. The number of compounds can be substantially increased by using combinations of the quinic and cinnamic acid derivatives synthesized as described above, and by using substituted hexanols in place of the cyclohexene carboxylic acids.

Initial studies consisted of the in vitro screening of compounds from each of the libraries synthesized using the schemes described above. Derivatives from each library were selected on the basis of potency using the in vitro stroke model described below. The most effective compounds, demonstrating neuroprotective activity along with acceptable $EC_{50}$ values were advanced to in vivo optimization.

Example 7

Illustrative Synthetic Schemes

Chemistry: General Methods. All reagents and anhydrous solvents were obtained from commercial sources and used as received. $^1$H NMR and $^{13}$C NMR were recorded at 500 and 125 MHz, respectively, on a Varian, VNMRS-500 spectrometer, using the indicated solvent. Chemical shift ($\delta$) is given in parts per million (ppm) relative to tetramethylsilane (TMS) as an internal standard. Coupling constants (J) are expressed in hertz (Hz), and conventional abbreviations used for signal shape are: s=singlet; d=doublet; t=triplet; m=multiplet; dd, doublet of doublets; brs=broad singlet. Mass spectrometry (LC/MS) was carried out using Shimadzu LC-20AD spectrometer and electro spray ionization (ESI) mass analysis by Thermo Scientific LTQ Orbitrap-XL spectrometer. All tested compounds had a purity of at least 95%. Thinlayer chromatography (TLC) used EMD silica gel F-254 plates (thickness 0.25 mm) Flash chromatography used EMD silica gel 60, 230-400 mesh.

The synthesis of substituted chalcones CMS-013, 032, 033, 057, 063, 085, 086, 086A, 105-108 and 137 was carried out by condensation of 2'-hydroxy acetophenones with appropriately substituted aldehydes using Ba(OH)$_2$ in methanol (Sogawa, et al., *J. Med. Chem.* (1993) 36 (24), 3904-3909) (Scheme 1). The tri-hydroxy chalcones CMS-011, 034 and 087 were prepared from the corresponding chalcones by treatment with BBr$_3$ in dichloromethane (Chu, et al., *Tetrahedron*. (2004) 60 (11), 2647-2655) and the di-hydroxy chalcone CMS-088 was synthesized by tetrahydropyran (THP) deprotection using para-toluene sulfonic acid (pTSA) in methanof from the corresponding chalcone. The substituted flavones CMS-018, 038, 058, 068, 089, 115, 116, 119 and 120 were synthesized from the corresponding chalcones using 12 in DMSO (Cabrera, et al., *Bioorganic & Medicinal Chemistry*.(2007) 15 (10), 3356-3367) (Scheme 2). The hydroxy flavones CMS-02P (a.k.a, PM-002), 028, 064, 072 and 094 were obtained from the corresponding chalcones by de-methylation/de-ethylation or de-benzylation using BBr$_3$ in dichloromethane (Chu, et al., *Tetrahedron*. (2004), supra) or H$_2$, Pd/C in EtOAc/methanol (Horie, et al., *J. Med. Chem.* (1986) 29 (11), 2256-2262), respectively.

Substituted flavonols CMS-025, 036, 037, 059, 065, 090, 091, 114, 117, 118, 122 and 139 were prepared (Scheme 3) using 5.4% NaOH, 30% H$_2$O$_2$ in methanol (Qin, et al., *J. Med. Chem.* (2008) 51 (6), 1874-1884) from the corresponding aldehydes. The known compounds Fisetin, CMS-02P (a.k.a, PM-002) and CMS-04P (a.k.a, PM-004) were purchased from Indofine Chemicals and the other hydroxy flavonols CMS-027, 040, 041, 069, 070, 092, 093 and 140 were obtained from their corresponding flavonols (Scheme 3) by de-methylation/de-ethylation (BBr$_3$ in dichloromethane) (Chu, et al., *Tetrahedron*. (2004), supra) or de-benzylation (H$_2$, Pd/C in EtOAc/methanol) (Horie, et al., *J. Med. Chem.* (1986) supra) methods. The substituted quinolines CMS-001, 004, 007, 017, 021-024, 083, 084, 109-113 and 121 were synthesized (Scheme 4) by condensation of 2'-amino acetophenones with appropriately substituted aldehydes using H$_2$SO$_4$ in methanol (Wang, et al., *Tetrahedron Letters*. (2009) 50 (19), 2261-2265).

General Procedure A for the Synthesis of Chalcone Derivatives CMS-013, 032, 033, 057, 063, 085, 086, 105-108 and 137. A mixture of 2'-hydroxy acetophenone (1 eq), aryl aldehyde (1 eq) and Ba(OH)$_2$ (1 eq) in MeOH (3 mL/mmol) was stirred for 12 h at 40° C. Methanol was evaporated and the residue was diluted with water, neutralized with 1N HCl and extracted with ethyl acetate. The organic layer was washed with brine solution, dried (Na$_2$SO$_4$) and evaporated. Solid residues were recrystallized from CH$_2$Cl$_2$/Hexane, liquid residues were purified by flash chromatography using silica gel (230-400 mesh) with 10-30% EtOAc/Hexane gave chalcones with 30-90% yield.

General Procedure B (methyl/ethyl deprotection) for the Synthesis of Compounds CMS-02P (a.k.a, PM-002), 011, 027, 028, 034, 041, 087, 093, 094 and 140. To a stirred and cooled 0° C. solution of suitably protected starting material (1 eq) in CH$_2$Cl$_2$ (5 mL/mmol) was added BBr$_3$ (2 eq/alkoxy group) and the mixture was stirred for overnight at room temperature under nitrogen atmosphere. The reaction mixture was quenched by adding 5% Na$_2$HPO$_4$ solution, extracted with CH$_2$Cl$_2$, combined organic extracts were washed with brine, dried (Na$_2$SO$_4$) and evaporated. The resulting solids were recrystallized from methanol.

Method C for the Synthesis of Chalcone CMS-088. To a stirred solution of chalcone CMS-086A (74.7 mg, 0.203 mmol) in MeOH (2 ml) was added p-toluenesulfonic acid (77.3 mg, 0.407 mmol). The reaction mixture was stirred for 3 h at room temperature, after completing the reaction solvent was evaporated, the residue was diluted with water (20 mL), then neutralized with saturated NaHCO$_3$, and extracted with EtOAc. Combined extracts were washed with brine, dried (Na$_2$SO$_4$), and evaporated. The residue was purified by flash chromatography using silica gel (230-400 mesh) with 20% EtOAc/Hexane gave CMS-088 94% yield, as a yellow solid.

General Procedure D (debenzylation) for the Synthesis of Compounds CMS-64, 069, 070, 072 and 092. The benzyl protected flavones and flavonols were dissolved in 1:1 EtOAc/Ethanol (10 mL/mmol) then treated with 5% palladium on charcoal (5% w/w) and the mixture was stirred under hydrogen atmosphere (balloon pressure) for overnight. The reaction mixture was filtered and the solvent was evaporated, the resulting solids were recrystallized from dichloromethane/methanol.

General Procedure E for the Synthesis of Flavone Derivatives CMS-018, 038, 058, 068, 089, 115, 116, 119 and 120. A solution of chalcone (1 eq) and iodine (0.01 eq) in DMSO (1 mL/mmol) was heated at 130° C. for 3-6 h. Reaction mixture was cooled and diluted with water, extracted with CH$_2$Cl$_2$, washed with aqueous saturated Na$_2$S$_2$O$_3$, dried (Na$_2$SO$_4$) and evaporated. Solid residues were recrystallized from CH$_2$Cl$_2$/Hexane liquid residues were purified by flash chromatography using silica gel (230-400 mesh) with 30-80% EtOAc/hexane gave flavones with 50-95% yield.

General Procedure F for the Synthesis Flavonol Derivatives CMS-025, 036, 037, 059, 065, 090, 091, 114, 117, 118, 122 and 139. To a stirred and cooled 0° C. solution of chalcone in MeOH (5 mL/mmol) was added 5.4% NaOH (3 2 mL/mmol) followed by 30% H$_2$O$_2$ (0.37 mL/mmol) drop wise, and the mixture was stirred for 3 h at 0° C., then the ice bath was left in place but not recharged, and stirring was continued overnight. The reaction mixture was acidified with 2M HCl, and the resulting precipitate was collected by filtration and washed with water and recrystallized from dichloromethane gave flavonols with 40-90% yield.

General Procedure G for the Synthesis of Quinoline Derivatives CMS-001, 004, 007, 017, 021-024, 083, 084, 109-113 and 121. To a stirred solution of 2'-amino acetophenone (1 eq) and aromatic aldehyde (1 to 3 eq) in alcohol (3 mL/mmol) was added H$_2$SO$_4$ (0.75 eq) and the mixture was refluxed for 12-24 h. The reaction mixture was cooled, the solvent evaporated and the residue was diluted with water. The aqueous solution was neutralized with 5% aqueous NaHCO$_3$ solution and extracted with ethyl acetate. The organic combines were washed with brine, dried (Na$_2$SO$_4$) and evaporated. Flash chromatography of the resulting residue over silica gel using 10-50% EtOAc/hexane gave 4-alkoxy 2-aryl quinolines with 15-50% yield.

Analytical data for selective compounds (CMS-011, CMS-121, and CMS-140): (E)-3-(3,4-dihydroxyphenyl)-1-(2-hydroxy-4,5-dimethylphenyl)prop-2-en-1-one (CMS-011). Following general procedure B, obtained CMS-011 from chalcone CMS-013 as an orange solid (95% yield); $^1$H NMR (DMSO-d$_6$, 500 MHz) δppm 2.23 (s, 3H), 2.24 (s, 3H), 6.78 (s, 1H) 6.82 (d, J=8.0 Hz, 1H), 7.23 (dd, J=8.5, 2.0 Hz, 1H), 7.31 (d, J=2.0 Hz, 1H), 7.72 (q, J=15.5 Hz, 2H), 8.02 (s, 1H), 9.11 (br s, OH), 9.81 (br s, OH), 12.79 (s, OH); $^{13}$C NMR (DMSO-d$_6$, 125 MHz) δppm 18.72, 20.46, 116.18, 116.36, 117.94, 118.45, 118.69, 123.19, 126.65, 127.59, 130.91, 146.04, 146.12, 146.92, 149.59, 161.23, 193.36; LCMS: m/z calcd for $C_{17}H_{16}O_4$ ([M]$^+$) 284; found 285 ([M+H]$^+$).

4-(4-(cyclopentyloxy) quinolin-2-yl) benzene-1, 2-diol (CMS-121). Following general procedure G, obtained CMS-121 as a yellow solid (16% yield); $^1$HNMR (DMSO-d$_6$, 500 MHz) δppm 1.66 (m, 2H), 1.79 (m, 2H), 1.89 (m, 2H), 2.07 (m, 2H), 5.30 (m, 2H), 6.85 (d, J=8.5 Hz, 1H), 7.31 (s, 1H), 7.44 (t, J=8.0 Hz, 1H), 7.54 (dd, J=8.5, 2.0 Hz, 1H), 7.67 (t, J=8.0 Hz, 1H), 7.75 (d, J=2.0 Hz, 1H), 7.88 (d, J=8.0 Hz, 1H), 8.04 (d, J=7.5 Hz, 1H), 9.21 (brs, OH); $^{13}$C NMR (DMSO-d$_6$, 125 MHz) δppm 24.19, 32.71, 80.12, 99.28, 115.02, 115.99, 119.41, 120.60, 121.97, 125.21, 128.93, 130.30, 131.11, 145.88, 147.71, 149.11, 157.92, 160.73; MS (ESI): m/z calcd for $C_{20}H_{19}NO_3$ ([M+H]$^+$) 322.1437; found 322.1412 ([M+H]$^+$).

3-hydroxy-2-(3-hydroxy-4-(pyrrolidin-1-yl)phenyl)-4H-benzo[h]chromen-4-one (CMS-140). Following general procedure B, obtained CMS-140 from compound CMS-139 as an orange-red solid (50% yield); $^1$HNMR (DMSO-d$_6$, 500 MHz) δppm 1.88 (s, 4H), 3.45 (s, 4H), 6.74 (d, J=8.5 Hz, 1H), 7.85 (m, 5H), 8.04 (d, J=8.5 Hz, 1H), 8.11 (d, J=8.5 Hz, 1H), 8.68 (d, J=7.5 Hz, 1H), 9.37 (s, 1H); $^{13}$C NMR (DMSO-d$_6$, 125 MHz) δppm 25.16, 50.19, 114.38, 114.69, 117.94, 120.61, 120.74, 120.99, 122.54, 124.10, 124.87, 128.06, 128.87, 129.77, 135.37, 139.19, 140.29, 146.34, 146.44, 151.65, 172.19; MS (ESI): m/z calcd for $C_{23}H_{19}NO_4$ ([M+H]$^+$) 374.1386; found 374.1402 ([M+H]$^+$).

Example 8

Structure-Activity Relationship and Neuroprotective Activity Analysis of Fisetin Derivatives Methods Biology: Cell culture. Fetal calf serum (FCS) and dialyzed FCS (DFCS) were from Hyclone (Logan, Utah). Dulbecco's Modified Eagle's Medium (DMEM) was purchased from Invitrogen (Carlsbad, Calif.). HT22 cells (Maher, et al., *Brain Research*. (2007) 1173, 117-125) were grown in DMEM supplemented with 10% FCS and antibiotics. PC12 cells were grown in DMEM supplemented with 10% FCS, 5% horse serum and antibiotics. N9 microglial cells were grown in DMEM supplemented with 10% FCS, 1x non-essential amino acids, 1x essential amino acids and antibiotics.

Cytotoxicity assay. Cell viability was determined by a modified version of 3-(4,5-dimethylthiazol-2-yl)-2,5-diphenyl tetrazolium bromide (MTT) assay based on the standard procedure (Maher, et al., *Brain Research*. (2007), supra). Cells were seeded onto 96-well microtiter plates at a density of $5\times10^3$ cells per well. For the in vitro ischemia assay, the next day, the medium was replaced with DMEM supplemented with 7.5% DFCS and the cells were treated with 20 μM iodoacetic acid (IAA) alone or in the presence of the different derivatives. After 2 hr the medium in each well was aspirated and replaced with fresh medium without IAA but containing the derivatives. 20 hr later, the medium in each well was aspirated and replaced with fresh medium containing 2.5 μg/ml MTT. After 4 hr of incubation at 37° C., the cells were solubilized with 100 μl of a solution containing 50% dimethylformamide and 20% SDS (pH 4.7). The absorbance at 570 nm was measured on the following day with a microplate reader (Molecular Devices). Results were confirmed by visual inspection of the wells. Controls included compound alone to test for toxicity and compound with no cells to test for interference with the assay chemistry.

Differentiation assay. PC$_{12}$ cells in N$_2$ medium were treated with the derivatives (1-10 μM) or Fisetin (10 μM) as a positive control for 24 hr at which time the cells were scored for the presence of neurites. PC$_{12}$ cells produce neurites much more rapidly when treated in N$_2$ medium than when treated in regular growth medium. For each treatment, 100 cells in each of three separate fields were counted. Cells were scored positive if one or more neurites >1 cell body diameter in length were observed.

Anti-inflammatory assay. Mouse N9 microglial cells plated in DME with 7.5% DFCS were treated with 10 μg/ml bacterial lipopolysaccharide (Sigma) alone or in the presence of the Fisetin derivatives (1-10 μM) or Fisetin (10 μM) as a positive control. After 24 hr the medium was removed, spun briefly to remove floating cells and 100 μl assayed for NO using 100 μl of the Griess Reagent (Sigma) in a 96 well plate. After incubation for 10 min at room temperature the absorbance at 550 nm was read on a microplate reader.

Total glutathione. Total intracellular glutathione was determined by a chemical assay as described (Maher, P. et al., *Free Radical Research*. (2006) 40 (10), 1105-1111).

SDS-PAGE and immunoblotting. For immunoblotting of Nrf2, nuclear extracts were prepared as described (Schreiber, et al., *Nucleic Acids Res*. (1989) 17 (15), 6419) from untreated cells and cells treated with the Fisetin derivatives for 1, 2 and 4 hr. Fisetin was used as a positive control. For each derivative, the concentration which was most effective at preventing cell death was used. Protein concentrations were determined using the BCA protein assay (Pierce). Equal amounts of protein were solubilized in 2.5× SDS-sample buffer, separated on 10% SDS-polyacrylamide gels and transferred to nitrocellulose. Equal loading and transfer of the samples was confirmed by staining the nitrocellulose with Ponceau-S. Transfers were blocked for 1 hr at room temperature with 5% nonfat milk in TBS/0.1% Tween 20 and then incubated overnight at 4° C. in the primary antibody diluted in 5% BSA in TBS/0.05% Tween 20. The primary antibodies used were: anti-Nrf2 (#SC13032; 1/1000) from Santa Cruz Biotechnology (Santa Cruz, Calif.) and anti-β-actin (#5125; 1/20,000) from Cell Signaling (Beverly, Mass.). The transfers were rinsed with TB S/0.05% Tween 20 and incubated for 1 hr at room temperature in horseradish peroxidase-goat anti-rabbit or goat anti-mouse (Biorad, Hercules, Calif.) diluted 1/5000 in 5% nonfat milk in TBS/0.1% Tween 20. The immunoblots were developed with the Super Signal reagent (Pierce, Rockford, Ill.).

Determination of the Trolox Equivalent Activity Concentration (TEAC). TEAC values for the flavonoids were determined as described (Maher, P. et al., *Free Radical Research*. (2006), supra). Briefly, 250 μl of 2,2'-azinobis(3-ethylbenzothiazoline6-sulfonate) (ABTS) treated overnight with potassium persulfate and diluted to an OD of ~0.7 at 734 nm was added to 2.5 μl of a derivative solution in ethanol. The change in absorbance due to the reduction of the ABTS radical cation was measured at 734 nm for 4 min. To calculate the TEAC, the gradient of the plot of the percentage inhibition of absorbance vs. concentration for the derivative in question was divided by the gradient of the plot for Trolox.

Results

Various embodiments described herein are based, in part, on the discovery of Fisetin analogs that display improved potency over Fisetin based upon the activation of multiple neuroprotective pathways while also maintaining or improving desirable physicochemical properties in comparison to successful CNS drugs (molecular weight≤400, tPSA≤5, tPSA≤90, HBD≤3, HBA≤7) (Hitchcock, et al., *J. Med. Chem.* (2006) 49 (26), 7559-7583; and Pajouhesh, et al., *NeuroRx.* (2005) 2, 541-553), to increase brain penetration, and to better understand its SAR. Two approaches to the improvement of Fisetin were explored. In the first, removal/modification/replacement of the different hydroxyl groups in a systematic manner was explored. In the second approach, modification of the flavone scaffold by changing it to a quinoline while at the same time maintaining key structural elements was explored.

For a primary screen, an in vitro ischemia model in combination with the HT22 nerve cell line (Maher, et al., *Brain Research.* (2007) 1173, 117-125) was chosen. For this screen, a cut-off for the $EC_{50}$ of 1 μM was chosen. To induce ischemia in the HT22 cells we used iodoacetic acid (IAA), a well-known, irreversible inhibitor of the glycolytic enzyme glyceraldehyde 3-phosphate dehydrogenase (G3PDH) (Winkler, et al., *Exp. Eye Res.* (2003) 76, 715-723). IAA has been used in a number of other studies to induce ischemia in nerve cells (Reshef, et al., *Neurosci. Lett.* (1997) 238, 37-40; Sperling, et al., *Neursci. Lett.* (2003) 351, 137-140; Rego, et al., *Neurochem. Res.* (1999) 24, 351-358; Sigalov, et al,. *J. Mol. Neurosci.* (2000) 15, 147-154; and Reiner, et al., *Neurosci. Lett.* (1990) 119, 175-178), including several recent screens for neuroprotective molecules (Biraboneye, et al., *J. Med. Chem.* (2009) 52 (14), 4358-4369; Biraboneye, et al., *Chem. Med. Chem.* (2010) 5 (1), 79-85). The changes following IAA treatment of neural cells are very similar to those seen in animal models of ischemic stroke (Lipton, et al., *Physiol. Rev.* (1999) 79, 1431-1568) and include alterations in membrane potential (Reiner, et al., *Neurosci. Lett.* (1990) 119, 175-178), breakdown of phospholipids (Taylor, et al., *J. Pharmacol. Exp. Ther.* (1996) 276, 1224-1231), loss of ATP (Winkler, et al., *Exp. Eye Res.* (2003) 76, 715-723; Sperling, et al., *Neursci. Lett.* (2003) 351, 137-140) and an increase in reactive oxygen species (ROS) (Taylor, et al., *J. Pharmacol. Exp. Ther.* (1996), supra; and Sperling, et al., *Neursci. Lett.* (2003) 351, 137-140).

Three secondary screens allowed assessment of three key activities of Fisetin that are highly relevant to stroke, as well as other neurological disorders: maintenance of glutathione (GSH), the major endogenous cellular antioxidant, inhibition of LPS-induced microglial activation, an indicator of anti-inflammatory activity and PC12 cell differentiation, a measure of neurotrophic activity. All of these activities are relevant to the nerve cell loss seen in stroke (Gelderblom, et al., *Stroke.* 2009, 40 (5), 1849-1857; Pandya, et al., *Cent. Nerv. Syst. Agents. Med. Chem.* (2011) Apr. 27; Lewerenz, et al., *J. Neurochem.* (2010) 113 (2), 502-504). Previous and ongoing studies suggest that these activities of Fisetin are mediated via distinct pathways but that all three may be important for the neuroprotective effects of Fisetin in vivo (Maher, P. *Genes. Nutr.* (2009) Sep. 10). To assess GSH maintenance, total intracellular GSH levels after a 24 hr treatment with the compound both in the absence and presence of glutamate, an inducer of GSH loss and oxidative stress (Tan, et al., *Curr. Top. Med. Chem.* (2001) 1, 497-506; Maher, et al., *Free Radical Research.* (2006) 40 (10), 1105-1111) was measured Inhibition of LPS-induced microglial activation was determined by treating N9 mouse microglial cells with LPS alone and in the presence of the compounds and assaying NO release into the medium 24 hr later (Zheng, et al., *Int. Immunopharmacol.* (2008) 8, (3), 484-494). PC12 cell differentiation was determined by treating PC12 cells with the compounds and looking at neurite outgrowth after 24 hr. In all cases, Fisetin was used as a positive control (Sagara, et al., *J. Neurochem.* (2004) 90, 1144-1155).

Structure Activity Relationships

Hydrogen bonding properties of drugs can significantly influence their CNS uptake profiles, polar molecules are generally poor CNS agents, low lipophilicity (CLogP) and high hydrogen bonding decreases BBB penetration (Pajouhesh, et al., NeuroRx. (2005) 2, 541-553). The roles of the four different hydroxyl groups in the activity of Fisetin were studied. It was found that removal of the 7-hydroxyl (CMS-04P (a.k.a, PM-004)) improved the neuroprotective activity ~6-fold over Fisetin in the primary screen of in vitro ischemia without loss of either the GSH-maintaining activity or PC12 cell differentiation, and also enhanced lipophilicity (from CLogP 1.24 to 1.82 (Table 1)). Further, this modification did not alter the anti-inflammatory activity relative to Fisetin (Table 1). Tables 1-3 show half maximal effective concentrations ($EC_{50}$s) for protection in the in vitro ischemia assay were determined by exposing HT22 cells to different doses of each derivative in the presence of 20 μM IAA for 2 hr (HT22/IAA). Cell viability was determined after 24 hr by the MTT assay. The ability to maintain GSH (GSH) was determined by treating HT22 cells with different doses of each derivative (1-10 μM) in the presence of 5 mM glutamate. After 24 hr cell extracts were prepared and analyzed for total GSH. Fisetin (10 μM) was used as a positive control. The ability to induce PC12 cell differentiation (PC12 diff'n) was determined by treating PC12 cells in $N_2$ medium with different doses of each derivative (1-10 μM) for 24 hr. Differentiation was assessed by visual inspection with Fisetin (10 μM) as a positive control. Anti-inflammatory activity (microglia) was assessed in N9 microglial cells treated with bacterial lipopolysaccharide alone or in the presence different doses of each derivative (1-10 μM) for 24 hr. Fisetin was used as a positive control. TEAC values, a measure of direct antioxidant activity, were determined using the ABTS+ decolorization assay.

TABLE 1

| Compound | M. Wt | tPSA | CLogP | Structure | $EC_{50}$ in vitro ischemia (μM) | GSH | PC12 diff'n | microglia | TEAC |
|---|---|---|---|---|---|---|---|---|---|
| Fisetin | 286 | 107 | 1.24 | 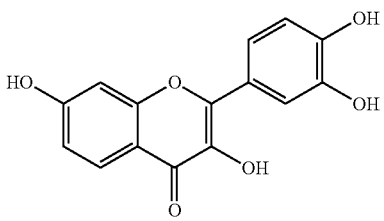 [SMILES: O=c1c(O)c(-c2ccc(O)c(O)c2)oc2cc(O)ccc12] | 3 | yes | yes | 80% | 3 |

TABLE 1-continued

| Compound | M. Wt | tPSA | CLogP | Structure | EC$_{50}$ in vitro ischemia (μM) | GSH | PC12 diff'n | microglia | TEAC |
|---|---|---|---|---|---|---|---|---|---|
| CMS-02P | 304 | 67 | 3.52 | 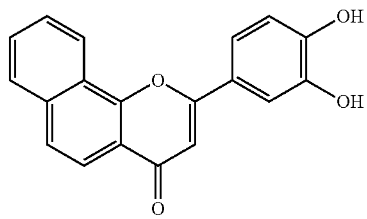 [SMILES: O=c1cc(-c2ccc(O)c(O)c2)oc2c1ccc1ccccc12] | 0.08 | no | yes | 55% | 0.18 |
| CMS-04P | 270 | 87 | 1.82 | 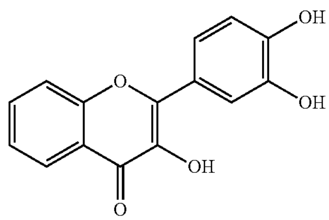 [SMILES: O=c1c(O)c(-c2ccc(O)c(O)c2)oc2ccccc12] | 0.5 | yes | yes | 80% | 2 |
| CMS-018 | 338 | 45 | 5.16 | 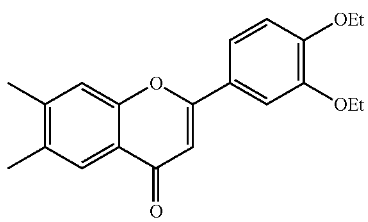 [SMILES: CCOc1ccc(-c2cc(=O)c3cc(C)c(C)cc3o2)cc1OCC] | no | no | no | 2% | 0.15 |
| CMS-025 | 354 | 65 | 4.71 | 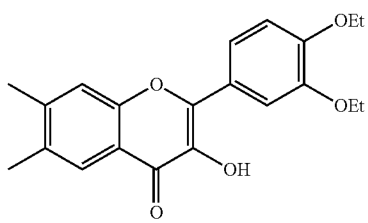 [SMILES: CCOc1ccc(-c2oc3cc(C)c(C)cc3c(=O)c2O)cc1OCC] | 0.5 | no | no | 11% | 0.84 |
| CMS-027 | 298 | 87 | 2.77 | 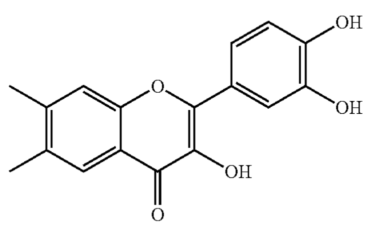 [SMILES: Cc1cc2oc(-c3ccc(O)c(O)c3)c(O)c(=O)c2cc1C] | 0.5 | no | no | 82% | 1.89 |
| CMS-028 | 282 | 67 | 3.30 | 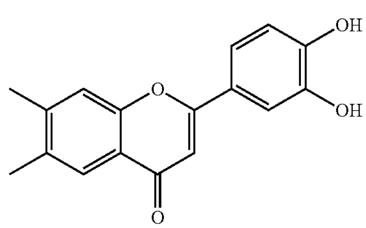 [SMILES: Cc1cc2oc(-c3ccc(O)c(O)c3)cc(=O)c2cc1C] | 0.25 | no | no | 93% | 0.27 |

TABLE 1-continued

| Compound | M. Wt | tPSA | CLogP | Structure | EC$_{50}$ in vitro ischemia (μM) | GSH | PC12 diff'n | microglia | TEAC |
|---|---|---|---|---|---|---|---|---|---|
| CMS-036 | 376 | 65 | 4.94 | 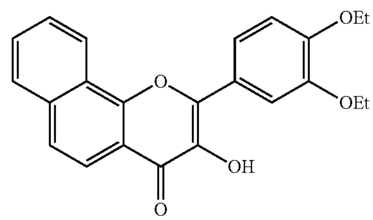 [SMILES: CCOc1ccc(-c2oc3c(ccc4ccccc43)c(=O)c2O)cc1OCC] | 0.3 | no | no | 13% | 0.15 |
| CMS-038 | 360 | 45 | 5.39 | 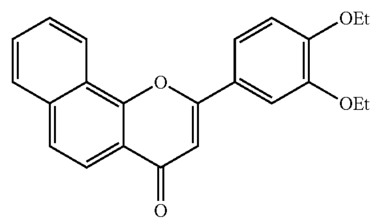 [SMILES: CCOc1ccc(-c2cc(=O)c3ccc4ccccc4c3o2)cc1OCC] | no | no | no | 2% | 0.2 |
| CMS-040 | 320 | 87 | 2.99 | 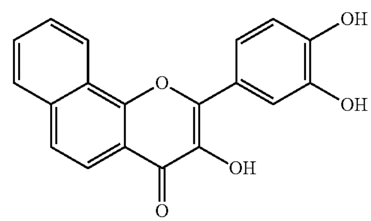 [SMILES: O=c1c(O)c(-c2ccc(O)c(O)c2)oc2c1ccc1ccccc12] | 0.09 | no | yes | 91% | 2.4 |
| CMS-041 | 320 | 87 | 2.99 | 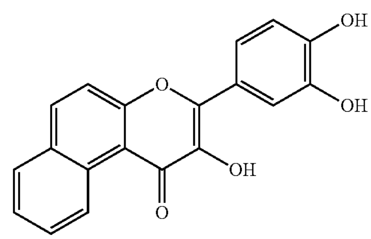 [SMILES: O=c1c(O)c(-c2ccc(O)c(O)c2)oc2ccc3ccccc3c12] | 0.25 | no | yes | 87% | 1.26 |
| CMS-058 | 386 | 45 | 5.87 | 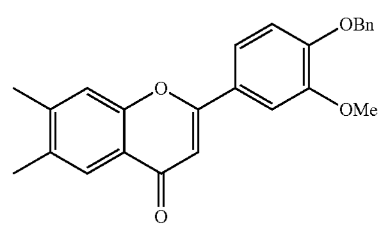 | 0.5 | no | no | 83% | 0.09 |
| CMS-059 | 402 | 65 | 5.42 | 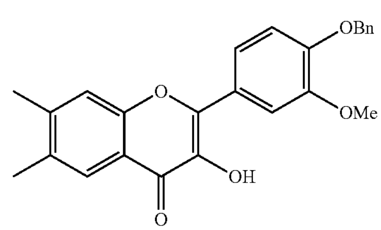 | 0.17 | no | no | 14% | 0.27 |

TABLE 1-continued

| Compound | M. Wt | tPSA | CLogP | Structure | EC$_{50}$ in vitro ischemia (μM) | GSH | PC12 diff'n | microglia | TEAC |
|---|---|---|---|---|---|---|---|---|---|
| CMS-064 | 296 | 56 | 3.66 | 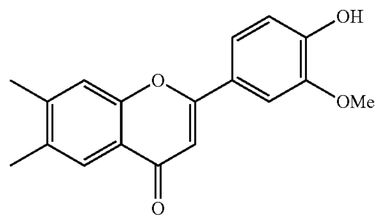 [SMILES: COc1cc(-c2cc(=O)c3cc(C)c(C)cc3o2)ccc1O] | 0.03 | no | no | 41% | 0.12 |
| CMS-065 | 424 | 65 | 5.65 | 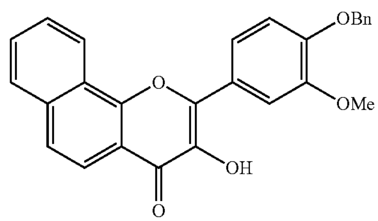 [SMILES: COc1cc(-c2oc3c(ccc4ccccc43)c(=O)c2O)ccc1OCc1ccccc1] | 0.08 | no | yes | 88% | 0 |
| CMS-069 | 312 | 76 | 3.19 | 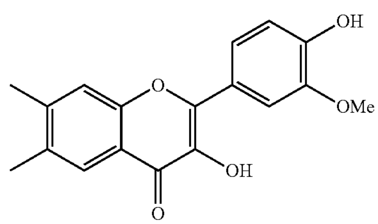 [SMILES: COc1cc(-c2oc3cc(C)c(C)cc3c(=O)c2O)ccc1O] | 0.04 | no | no | 77% | 1.89 |
| CMS-070 | 334 | 76 | 3.41 | 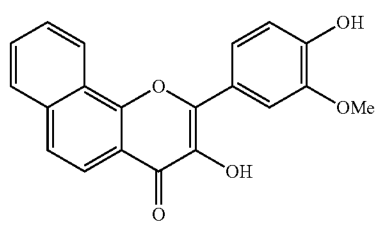 [SMILES: COc1cc(-c2oc3c(ccc4ccccc43)c(=O)c2O)ccc1O] | >0.5 | no | yes | 78% | 0.63 |
| CMS-072 | 318 | 56 | 3.88 | 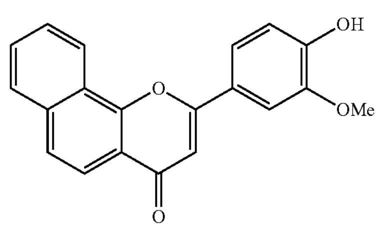 [SMILES: COc1cc(-c2cc(=O)c3ccc4ccccc4c3o2)ccc1O] | 0.04 | no | no | 19% | 0.2 |
| CMS-092 | 312 | 76.00 | 3.19 | 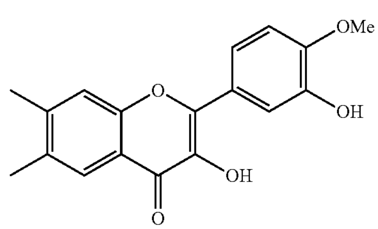 [SMILES: COc1ccc(-c2oc3cc(C)c(C)cc3c(=O)c2O)cc1O] | 0.02 | no | no | 72% | 1.74 |

TABLE 1-continued

| Compound | M. Wt | tPSA | CLogP | Structure | EC$_{50}$ in vitro ischemia (μM) | GSH | PC12 diff'n | microglia | TEAC |
|---|---|---|---|---|---|---|---|---|---|
| CMS-093 | 298 | 87.00 | 2.40 | 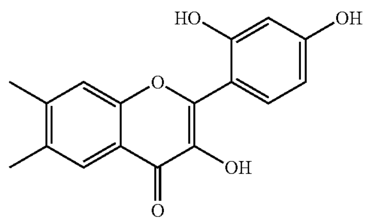 [SMILES: Cc1cc2oc(-c3ccc(O)cc3O)c(O)c(=O)c2cc1C] | >0.5 | no | no | 0% | 1.56 |
| CMS-094 | 282 | 66.76 | 2.93 | 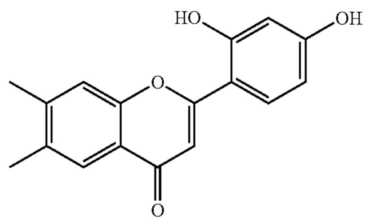 [SMILES: Cc1cc2oc(-c3ccc(O)cc3O)cc(=O)c2cc1C] | >0.5 | no | no | 5% | 0.15 |
| CMS-114 | 357 | 49.77 | 4.51 | 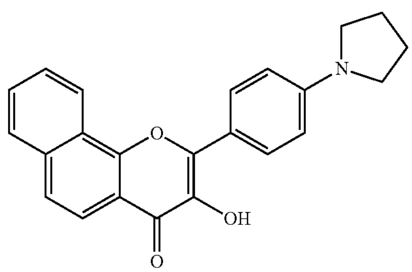 [SMILES: O=c1c(O)c(-c2ccc(N3CCCC3)cc2)oc2c1ccc1ccccc12] | 0.07 | no | yes | 26% | 1.44 |
| CMS-115 | 341 | 29.54 | 4.99 | 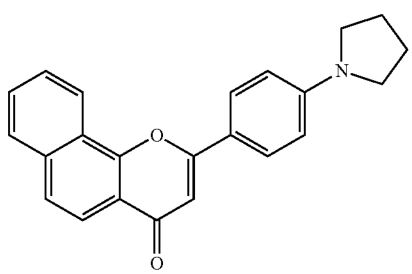 [SMILES: O=c1cc(-c2ccc(N3CCCC3)cc2)oc2c1ccc1ccccc12] | 0.2 | no | no | 23% | 0.03 |
| CMS-116 | 319 | 29.54 | 4.70 | 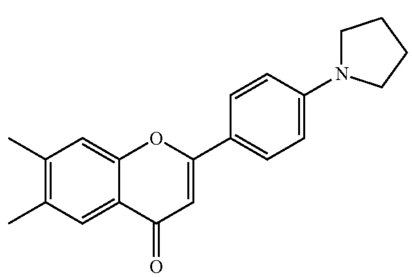 [SMILES: Cc1cc2oc(-c3ccc(N4CCCC4)cc3)cc(=O)c2cc1C] | >0.5 | no | no | 2% | 0.12 |
| CMS-117 | 309 | 49.77 | 4.17 | 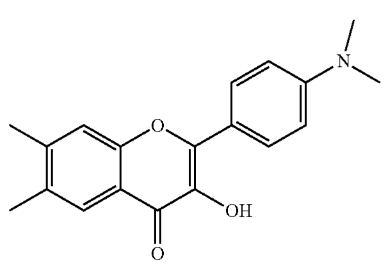 | 0.02 | yes | no | 11% | 3 |

TABLE 1-continued

| Compound | M. Wt | tPSA | CLogP | Structure | EC$_{50}$ in vitro ischemia (μM) | GSH | PC12 diff'n | microglia | TEAC |
|---|---|---|---|---|---|---|---|---|---|
| CMS-118 | 331 | 49.77 | 4.40 | 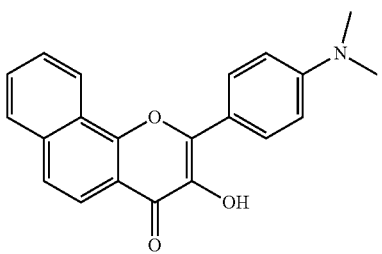 [SMILES: CN(C)c1ccc(-c2oc3c(ccc4ccccc43)c(=O)c2O)cc1] | 0.04 | yes | no | 0% | 0.93 |
| CMS-119 | 293 | 29.54 | 4.65 | 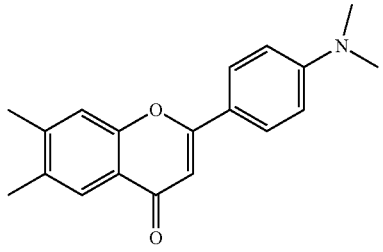 | >0.5 | no | no | 8% | 0 |
| CMS-120 | 315 | 29.54 | 4.88 | 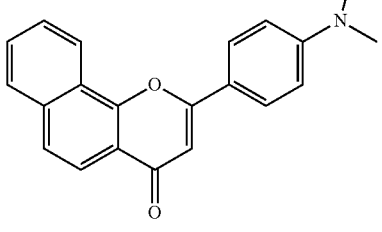 | 0.25 | no | no | 35% | 0.24 |
| CMS-122 | 335 | 49.77 | 4.28 | 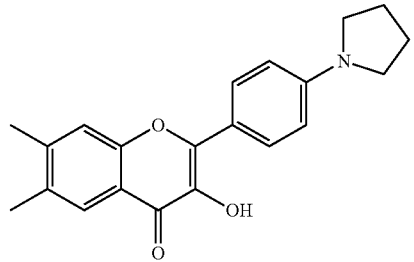 [SMILES: Cc1cc2oc(-c3ccc(N4CCCC4)cc3)c(O)c(=O)c2cc1C] | 0.09 | yes | yes | 0% | 2.4 |
| CMS-140 | 372 | 70.00 | 4.09 | 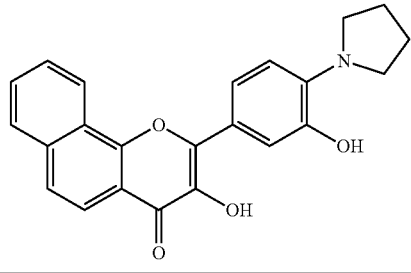 [SMILES: O=c1c(O)c(-c2ccc(N3CCCC3)c(O)c2)oc2c1ccc1ccccc12] | 0.005 | Yes | Yes | 50% | 2.1 |

This finding spurred replacement of the 7-hydroxyl group with hydrophobic groups in order to improve the lipophilicity and tPSA to values more consistent with typical CNS drugs (Hitchcock, et al., *J. Med. Chem.* (2006) 49 (26), 7559-7583 and Pajouhesh, et al., *NeuroRx.* (2005) 2, 541-553). The addition of a benzene ring (CMS-040) to the A ring further enhanced neuroprotective activity ~5.5-fold with a much more pronounced effect seen with the α-naphthyl derivative (CMS-040) as opposed to the β-naphthyl (CMS-041) derivative (Table 1). However, this modification reduced the ability of the derivative to maintain GSH under conditions of oxidative stress. For this derivative, the 3-hydroxyl was did not seem to affect neuroprotective activity (CMS-040 vs CMS-02P (a.k.a, PM-002)) but did enhance anti-inflammatory activity. We also examined the role of the B ring hydroxyls in neuroprotection as well as the other key activities of alpha lnaphthyl derivative. Changing both hydroxyls to ethoxy groups (CMS-036, CMS-038) not only greatly reduced neuroprotective activity but also eliminated both the anti-inflammatory activity and the ability to induce PC12 cell differentiation. Changing only one of the hydroxyls to a methoxy group enhanced neuroprotective activity ~2-fold over CMS-040 in the absence of the 3-hydroxyl group (CMS-072) but greatly reduced neuroprotective activity relative to CMS-040 in the presence of the 3 hydroxyl (CMS-070). Furthermore, this modification did not restore the ability to maintain GSH under conditions of oxidative stress and the derivative without the 3 hydroxyl (CMS-072) also lacked anti-inflammatory activity and the ability to induce PC12 cell differentiation.

Surprisingly, changing the 4'-hydroxyl to a benzyloxy group (CMS-065) restored neuroprotective activity in the presence of the 3-hydroxyl. Compounds possessing tertiary nitrogen (a feature of many CNS drugs) show a higher degree of brain permeation (Hitchcock, et al., *J. Med. Chem.* (2006) 49 (26), 7559-7583; Pajouhesh, et al., *NeuroRx*. (2005) 2, 541-553; and Lloyed, et al., *J. Med. Chem.* (1986) 29, 453-462). However, also effective in terms of neuroprotective activity was the replacement of the both hydroxyls with a single dimethyl amino group at the 4'-position which resulted in a highly neuroprotective compound in the presence of the 3-hydroxyl group (CMS-118) and a somewhat less effective compound in its absence (CMS-120), also this modification eliminated two hydrogen bond donors. Although CMS-118 regained the ability to maintain GSH levels, it lacked both anti-inflammatory and neurotrophic activity. Modification of the dimethyl amine to a pyrrolidine group at the 4'-position gave a compound that had excellent neuroprotective activity in the presence of the 3-hydroxyl (CMS-114) and could also induce PC12 cell differentiation but had poor anti-inflammatory activity and did not maintain GSH levels. In sum, an additional benzene ring (α-naphthyl) enhanced neuroprotective activity up to 75-fold, but many derivatives lacked the ability to maintain GSH under oxidative stress. Some deficiency in anti-inflammatory activity was noted in these analogs. A second approach to improving the pharmacological properties of Fisetin was also explored.

For this second approach, replacement of the benzene ring with two methyl groups (CMS-027) was performed in order to generate a derivative with a similar CLogP and tPSA as CMS-040 but with a less bulky addition to the A ring (Table 1). Surprisingly, this derivative not only showed significantly decreased neuroprotective activity as compared with CMS-040 but also lost the ability to induce PC12 cell differentiation along with the continued failure to maintain GSH levels. Removal of the 3-hydroxyl enhanced neuroprotective activity 2-fold (CMS-028) but did not restore the induction of PC12 cell differentiation or the maintenance of GSH. Modification of the B ring hydroxyls produced mixed results. Modification of one hydroxyl to a methoxy (CMS-064, CMS-069, CMS-092) improved neuroprotective activity ~10-20-fold but reduced anti-inflammatory activity. Similar to the results with the derivatives of CMS-040, modification of both the B ring hydroxyl groups to ethoxy groups (CMS-018, CMS-025) gave similar levels of neuroprotective activity.

Also, these derivatives exhibited little if any ability to maintain GSH or induce PC12 cell differentiation and they also showed reduced anti-inflammatory activity. While the methoxy, benzyloxy dimethyl derivative showed enhanced neuroprotective activity relative to CMS-027 in the presence of the 3-hydroxyl (CMS-059), it exhibited relatively low anti-inflammatory activity. Further, separation of the B ring hydroxyls (CMS-093, CMS-094) not only eliminated neuroprotective activity but the other key activities as well. However, similar to the results with the derivatives of CMS-040, replacement of the hydroxyls with a single dimethyl amino group at the 4' position produced a compound with excellent neuroprotective activity but only in the presence of the 3-hydroxyl (CMS-117 vs CMS-119). This compound also regained the ability to maintain GSH but lacked neurotrophic and anti-inflammatory activity. Addition of a single pyrrolidine group to the 4' position instead gave a compound that had excellent neuroprotective activity only in the presence of the 3 hydroxyl (CMS-122 vs CMS-116) and could also maintain GSH levels and induce PC12 cell differentiation but still had poor anti-inflammatory activity. However, addition of a 3'-hydroxyl to this derivative resulted in a compound with outstanding neuroprotective activity (CMS-140) that could also maintain GSH under conditions of oxidative stress, induce PC12 differentiation and had reasonable anti-inflammatory activity.

Chalcones are intermediates in the synthesis of flavonoids and were used to determine the effect of opening up the C-ring on activity (Table 2). Surprisingly, the chalcones of both the naphthyl (CMS-034) and dimethyl derivatives (CMS-011) had similar (CMS-034) or enhanced (CMS-011) neuroprotective activity compared to their flavone counterparts and also regained all of the key activities including the ability to maintain GSH under conditions of oxidative stress. In contrast, the chalcones where both the B ring hydroxyls were modified had either no (CMS-032, CMS-013, CMS-086) or greatly reduced (CMS-063) neuroprotective activity. Furthermore, splitting the B ring hydroxyls of CMS-011 (CMS-087) eliminated the ability to maintain GSH under conditions of oxidative stress. The conversion of a hydroxyl to a methoxy (CMS-088) also eliminated the ability to promote PC12 cell differentiation.

TABLE 2

| Compound | M. Wt | tPSA | CLogP | Structure | $EC_{50}$ in vitro ischemia (μM) | GSH | PC12 diff'n | microglia | TEAC |
|---|---|---|---|---|---|---|---|---|---|
| Fisetin | 286 | 107 | 1.24 | 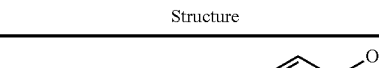 | 3 | yes | yes | 80% | 3 |

TABLE 2-continued

| Compound | M. Wt | tPSA | CLogP | Structure | EC$_{50}$ in vitro ischemia (μM) | GSH | PC12 diff'n | microglia | TEAC |
|---|---|---|---|---|---|---|---|---|---|
| CMS-011 | 284 | 78 | 3.64 | 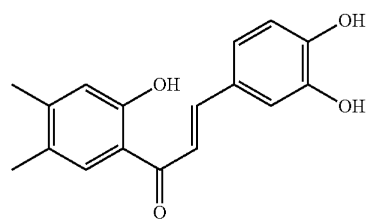 [SMILES: Cc1cc(O)c(C(=O)/C=C/c2ccc(O)c(O)c2)cc1C] | 0.05 | yes | yes | 94% | 2.7 |
| CMS-013 | 340 | 56 | 5.62 | 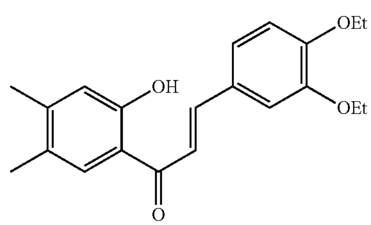 [SMILES: CCOc1ccc(/C=C/C(=O)c2cc(C)c(C)cc2O)cc1OCC] | no | no | no | 56% | 0.09 |
| CMS-032 | 362 | 56 | 5.84 | 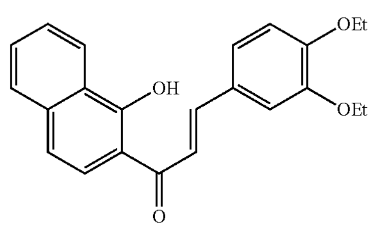 [SMILES: CCOc1ccc(/C=C/C(=O)c2ccc3ccccc3c2O)cc1OCC] | no | no | no | 5% | 0.12 |
| CMS-034 | 306 | 78 | 3.86 | 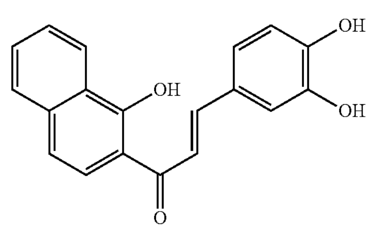 [SMILES: O=C(/C=C/c1ccc(O)c(O)c1)c1ccc2ccccc2c1O] | 0.08 | yes | yes | 75% | 2.8 |
| CMS-063 | 410 | 56 | 6.55 | 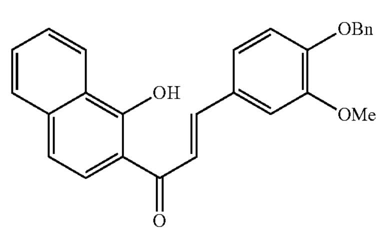 [SMILES: COc1cc(/C=C/C(=O)c2ccc3ccccc3c2O)ccc1OCc1ccccc1] | 0.5 | no | no | 9% | 0.15 |
| CMS-086 | 388 | 55.76 | 6.33 | 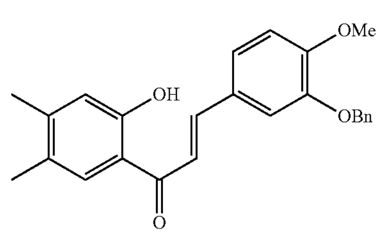 [SMILES: COc1ccc(/C=C/C(=O)c2cc(C)c(C)cc2O)cc1OCc1ccccc1] | no | yes | yes | 70% | 0.12 |

TABLE 2-continued

| Compound | M. Wt | tPSA | CLogP | Structure | EC$_{50}$ in vitro ischemia (μM) | GSH | PC12 diff'n | microglia | TEAC |
|---|---|---|---|---|---|---|---|---|---|
| CMS-087 | 284 | 77.76 | 3.57 | 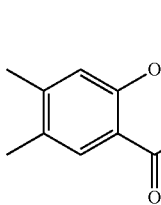 | 0.05 | no | yes | 53% | 0.93 |
| CMS-088 | 298 | 66.76 | 4.08 | 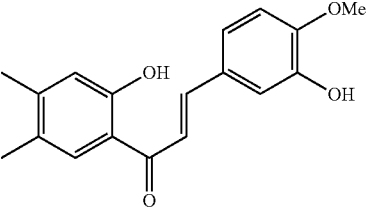 [SMILES: COc1ccc(/C=C/C(=O)c2cc(C)c(C)cc2O)cc1O] | 0.2 | no | no | 56% | 0.12 |

As an alternative approach to improving Fisetin, we modified the flavone scaffold changing it to a quinoline scaffold (Table 3) in an attempt to further improve potency and physiochemical properties while retaining the key structural elements of the flavone in the quinoline scaffold.

TABLE 3

| Compound | M. Wt | tPSA | CLogP | Structure | EC$_{50}$ in vitro ischemia (μM) | GSH | PC12 diff'n | microglia | TEAC |
|---|---|---|---|---|---|---|---|---|---|
| Fisetin | 286 | 107 | 1.24 | 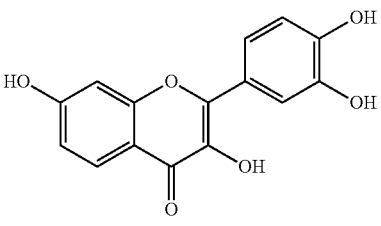 | 3 | yes | yes | 80% | 3 |
| CMS-001 | 281 | 51 | 3.89 | 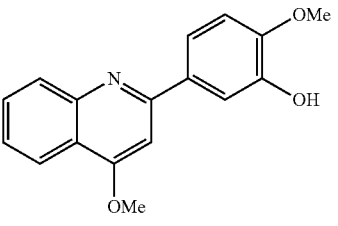 [SMILES: COc1ccc(-c2cc(OC)c3ccccc3n2)cc1O] | no | no | no | 69% | 0.24 |
| CMS-004 | 323 | 40 | 5.33 | 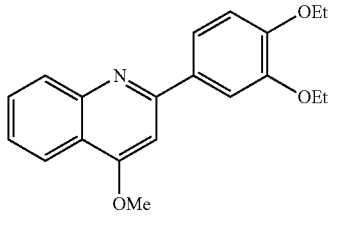 [SMILES: CCOc1ccc(-c2cc(OC)c3ccccc3n2)cc1OCC] | no | no | no | 76% | 0.12 |

TABLE 3-continued
| Compound | M. Wt | tPSA | CLogP | Structure | EC$_{50}$ in vitro ischemia (μM) | GSH | PC12 diff'n | microglia | TEAC |
|---|---|---|---|---|---|---|---|---|---|
| CMS-007 | 267 | 62 | 3.66 | 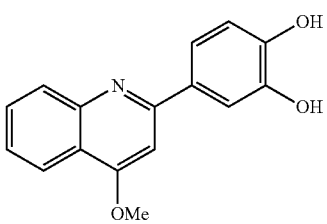 [SMILES: COc1cc(-c2ccc(O)c(O)c2)nc2ccccc12] | 0.04 | yes | no | 85% | 0.36 |
| CMS-017 | 281 | 51 | 3.89 | 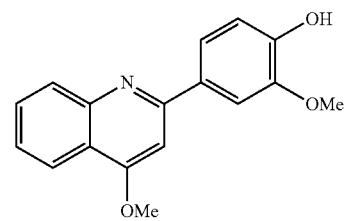 [SMILES: COc1cc(-c2cc(OC)c3ccccc3n2)ccc1O] | 0.5 | no | no | 90% | 0.15 |
| CMS-021 | 235 | 21 | 4.55 | 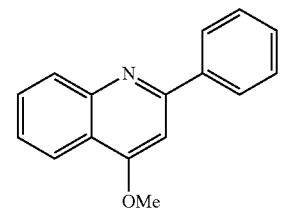 [SMILES: COc1cc(-c2ccccc2)nc2ccccc12] | 0.75 | no | no | 6% | 0.12 |
| CMS-022 | 251 | 42 | 4.07 | 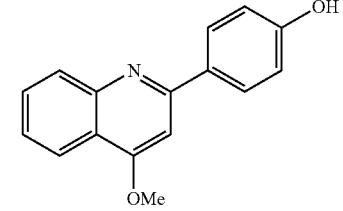 [SMILES: COc1cc(-c2ccc(O)cc2)nc2ccccc12] | no | no | no | 4% | 0.81 |
| CMS-023 | 281 | 62 | 4.20 | 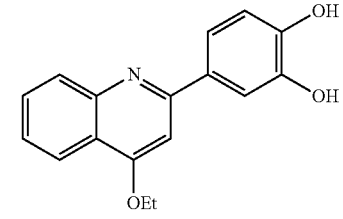 [SMILES: CCOc1cc(-c2ccc(O)c(O)c2)nc2ccccc12] | 0.02 | yes | yes | 90% | 0.90 |
| CMS-024 | 295 | 62 | 4.50 | 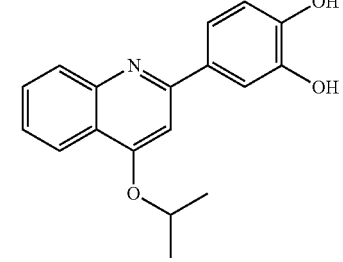 | 0.02 | yes | yes | 80% | 0.18 |

TABLE 3-continued

| Compound | M. Wt | tPSA | CLogP | Structure | EC$_{50}$ in vitro ischemia (μM) | GSH | PC12 diff'n | microglia | TEAC |
|---|---|---|---|---|---|---|---|---|---|
| CMS-083 | 267 | 62.06 | 3.30 | 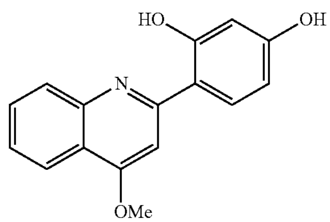 [SMILES: COc1cc(-c2ccc(O)cc2O)nc2ccccc12] | >0.5 | no | no | 84% | 0.05 |
| CMS-084 | 295 | 62.05 | 4.13 | 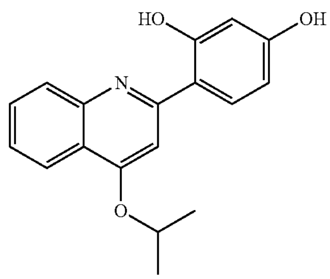 [SMILES: CC(C)Oc1cc(-c2ccc(O)cc2O)nc2ccccc12] | 0.21 | no | no | 64% | 0.27 |
| CMS-109 | 278 | 24.83 | 4.82 | 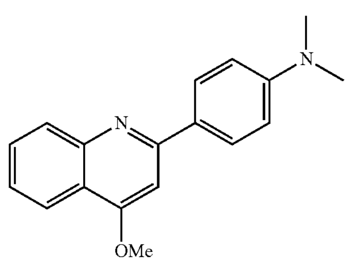 [SMILES: COc1cc(-c2ccc(N(C)C)cc2)nc2ccccc12] | 0.06 | no | no | 62% | 0.06 |
| CMS-110 | 304 | 24.83 | 4.93 | 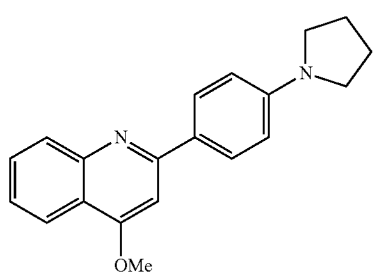 [SMILES: COc1cc(-c2ccc(N3CCCC3)cc2)nc2ccccc12] | no | no | no | 67% | 0.27 |
| CMS-111 | 296 | 93.63 | 4.33 | 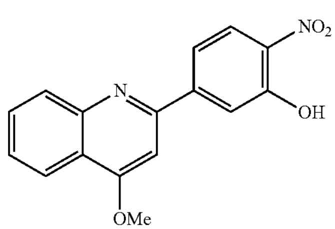 [SMILES: COc1cc(-c2ccc([N+](=O)[O-])c(O)c2)nc2ccccc12] | no | no | no | 25% | 0.18 |

TABLE 3-continued

| Compound | M. Wt | tPSA | CLogP | Structure | EC$_{50}$ in vitro ischemia (μM) | GSH | PC12 diff'n | microglia | TEAC |
|---|---|---|---|---|---|---|---|---|---|
| CMS-112 | 306 | 24.83 | 5.66 | 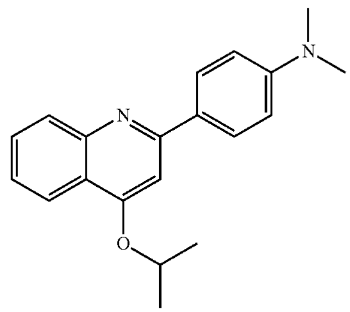 [SMILES: CC(C)Oc1cc(-c2ccc(N(C)C)cc2)nc2ccccc12] | 0.05 | no | no | 71% | 0.15 |
| CMS-113 | 332 | 24.83 | 5.77 | 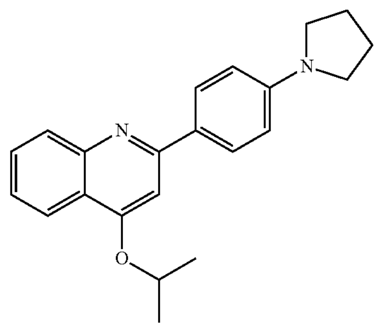 [SMILES: CC(C)Oc1cc(-c2ccc(N3CCCC3)cc2)nc2ccccc12] | 0.5 | no | no | 67% | 0.27 |
| CMS-121 | 321 | 62.05 | 5.14 | 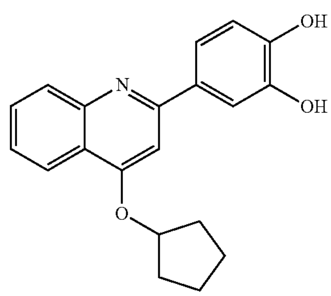 [SMILES: Oc1ccc(-c2cc(OC3CCCC3)c3ccccc3n2)cc1O] | 0.007 | yes | yes | 82% | 0.40 |

Compound CMS-007 showed a ~75-fold increase in neuroprotective activity relative to Fisetin, maintained GSH under conditions of oxidative stress and had strong anti-inflammatory activity. It did not induce PC12 cell differentiation. A number of modifications were explored to see if neuroprotective activity could be enhanced and/or PC12 cell differentiating activity could be restored. Interestingly, the substitution of an ethoxy (CMS-023) or an iso-propoxy (CMS-024) for the methoxy group on the C ring did restore the differentiating activity while also slightly improving (~2-fold) the neuroprotective activity relative to CMS-007. Replacement of the O-methyl group with an O-cyclopentyl ring resulted in a compound with a >400-fold decrease in EC$_{50}$ relative to Fisetin for neuroprotective activity (CMS-121) and maintenance of all of the key activities. For all forms, removal of one (CMS-022) or both (CMS-021) of the B ring hydroxyls or conversion of one or both of these hydroxyls to methoxy (CMS-001, CMS-017), ethoxy (CMS-004), nitro (CMS-111) or chlorine or fluorine (not shown) greatly reduced or eliminated neuroprotective activity. All of these changes also reduced or eliminated all of the other key activities. Splitting the two ring hydroxyls (CMS-083, CMS-084) also reduced neuroprotective activity and eliminated the ability to maintain GSH and induce PC12 cell differentiation but did not impact anti-inflammatory activity. In contrast to the derivatives based on the flavone scaffold, the addition of a single dimethyl amino (CMS-109, CMS-112) or pyrrolidine group (CMS-110, CMS-113) to the 4' position of the B ring did not enhance neuroprotective activity relative to the 3', 4' dihydroxy derivative and generally resulted in a reduction or elimination of the other key activities. Thus, in the presence of the quinoline scaffold the catechol group on the B ring is essential for activity.

The transcription factor Nrf2 plays a key role in regulating GSH metabolism in many different cell types (Lewerenz, et al., *Antioxidant & Redox Signaling*. (2011) 14, 1449-1465). We have shown that Fisetin can induce Nrf2 and this correlates with its ability to enhance GSH levels (Maher, P. et al., *Genes. Nutr.* (2009) Sep. 10). To determine if the derivatives which can maintain GSH levels do so by increasing Nrf2 we looked at Nrf2 levels in the nuclei of derivative-treated cells using Fisetin as a positive control (Table 4). Surprisingly, not all of the derivatives that maintained GSH levels induced Nrf2. This was particularly true for the derivatives based on the quinoline scaffold where none of them increased Nrf2 despite being very effective at maintaining GSH levels.

TABLE 4

| Compound | Nrf2 |
| --- | --- |
| Fisetin | Yes |
| CMS-04P (a.k.a, PM-004) | Yes |
| CMS-117 | No |
| CMS-118 | No |
| CMS-122 | No |
| CMS-140 | No |
| CMS-011 | Yes |
| CMS-034 | Yes |
| CMS-086 | Yes |
| CMS-007 | No |
| CMS-023 | No |
| CMS-024 | No |
| CMS-121 | No |

The ability of the derivatives that maintain GSH levels to induce the transcription factor Nrf2 was assayed by SDS-PAGE and Western blotting of nuclear extracts of untreated and derivative-treated cells. Fisetin treatment was used as a positive control.

Discussion

Several important findings emerge from this study. First, within the flavone scaffold SAR demonstrated various selectivities among four distinct biological activities and improved neuroprotective activity up to 600-fold (CMS-140). While it is possible to maintain all of the activities that are likely to be important for in vivo efficacy, each of these activities seems to have specific and distinct structural requirements. Thus, using the compounds described herein, it is possible to balance enhanced neuroprotective activity with the other key activities as well as the physical characteristics of the compounds in order to arrive at compounds that have efficacy in vivo. An additional finding is that neither the neuroprotective activity nor any of the other three key activities of the Fisetin derivatives synthesized thus far show correlation with antioxidant activity as defined by the TEAC value (Table 1).

Each of the tested activities of the Fisetin derivatives shows distinct structural requirements. For example, within the flavone structure (Table 1), the maintenance of GSH poses the strictest structural requirements. It is highly sensitive to modification of the A ring (CMS-040, CMS-027). Substitution of the B ring hydroxyls with a tertiary-amino group is compatible with the maintenance of GSH even in the presence of A ring modifications (CMS-117, CMS-118) as long as a 3 hydroxyl group is present. In contrast, the anti-inflammatory activity of the flavone-based derivatives is not particularly sensitive to modification of the A ring, especially in the presence of a 3-hydroxyl group (e.g. CMS-040 vs. CMS-04P (a.k.a, PM-004)). The anti-inflammatory activity of the flavone-based derivatives, however, is less tolerant of modification of the B ring hydroxyls (e.g. CMS-036, CMS-072) and is also less tolerant of substitution of the tertiary-amino groups regardless of the presence of a 3-hydroxyl group (e.g. CMS-117, CMS-119). The anti-inflammatory dampening effect of the tertiary amino groups is reduced by the re-addition of a hydroxyl group to the 3' position (CMS-140). The PC12 differentiation promoting activity of the flavone-based derivatives shows a similar but less demanding set of structural requirements as the GSH maintaining activity for it is somewhat more tolerant of modifications to the A ring (e.g. CMS-040 but not CMS-027). In addition, while this activity is sensitive to modifications of the B ring hydroxyls, it tolerates limited modifications that eliminate the GSH maintaining activity (e.g. CMS-065).

Once the flavone structure is opened up to give the chalcone (Table 2), only modification of the B ring hydroxyls affects the GSH maintaining activity of the Fisetin derivatives. The one exception is CMS-086 which has a methoxy and a benzyloxy group on the B ring. The PC12 differentiation promoting activity of the chalcone-based derivatives shows similar structural requirements as the GSH maintaining activity. Interestingly, while the anti-inflammatory activity of the α-naphtha chalcone-based derivatives is eliminated by modification of the B ring hydroxyls, the anti-inflammatory activity of the dimethyl chalcone based-derivatives is much more tolerant of this type of modification.

The quinoline scaffold reserves the key structural elements of the flavone and results in enhanced neuroprotective activity up (up to >400×) while maintaining the other enumerated activities. Although these derivatives have reduced free radical scavenging activity based on TEAC values (Table 1) relative to Fisetin, several are highly neuroprotective in the described in vitro assay. In addition, while the most neuroprotective compounds with this scaffold have hydroxyl groups, they are not polyphenolic. Interestingly, within the context of this scaffold, the structural requirements for each activity are somewhat sharper. For the maintenance of GSH, a catechol group on the B ring is important. PC12 differentiation promoting activity requires both a catechol group on the B ring and a hydrophobic group on the 4-position of the C ring. The requirements for anti-inflammatory activity are somewhat less stringent but are sensitive to modifications of the B ring hydroxyls in a manner similar to the flavone-based derivatives.

It is possible to separate neuroprotective activity from the three other enumerated activities of Fisetin. This result suggests that none of the three activities play a role in neuroprotection in the in vitro ischemia assay. Both the differentiation-promoting and anti-inflammatory activities could have important roles in maintaining CNS function in vivo but are less likely to be relevant in an in vitro assay with a single cell type. What is more surprising is that the ability to maintain GSH is not essential for neuroprotection in the in vitro ischemia assay as GSH loss is a component of this cell death paradigm (Maher, et al., *Brain Research*. (2007) 1173, 117-125). However, the compounds with the lowest $EC_{50}$'s for neuroprotection are all effective at maintaining GSH levels. Furthermore, many of the effective neuroprotective compounds that do not maintain GSH are also not good antioxidants as defined by the TEAC assay, an in vitro assay for antioxidant activity. While not wishing to be bound by theory, these results suggest that the neuroprotection by the compounds described herein is mediated by some other, as yet undefined, actions of these compounds.

Surprisingly, the ability to maintain GSH levels did not correlate with the induction of Nrf2 by the compounds. There are a number of other mechanisms for maintaining GSH levels that could be modulated by these compounds including reduction of GSH utilization or inhibition of GSH export (Lewerenz, et al., *Antioxidant& Redox Signaling*. (2011) 14, 1449-1465).

Fisetin derivatives described herein also have improved medicinal chemical properties in terms of HBD, CLogP and tPSA, falling within the criteria for CNS drugs (Hitchcock, et al., *J. Med. Chem*. (2006) 49 (26), 7559-7583; and Pajouhesh, et al., NeuroRx. (2005) 2, 541-553). Also, the Fisetin derivatives described herein, because they lack A ring hydroxyl groups which are known to be subject to modification following oral administration, are less likely to be metabolized, leading to enhanced bioavailability and brain penetration (Shia, et al., *J. Agric. Food Chem*. (2009) 57(1):83-89).

Starting with the multi-target polyphenol Fisetin, a number of derivatives were prepared, showing greatly enhanced neuroprotective activity (e.g. CMS-011 50 nM, CMS-121 7 nM and CMS-140 5 nM) in a cell culture-based model of ischemia. Many of the more potent Fisetin derivatives also have good CNS drug-like properties. Some of these derivatives also maintain the other three described activities of Fisetin demonstrating their efficacy by correlation to stroke as well as other neurological diseases. It is possible to enhance a primary activity of a polyphenol such as Fisetin while at the same time maintaining other key activities which are not necessarily directly related to this primary activity.

Example 9

In vitro Stroke Screening Assays

HT22 Cell screen: For rapid screening of chemical libraries, a mouse HT22 hippocampal cell death assay induced by addition of the compound iodoacetic acid (IAA) was used. IAA is a well-known, irreversible inhibitor of the glycolytic enzyme glyceraldehyde 3-phosphate dehydrogenase (G3PDH). IAA has been used in a number of other studies to induce ischemia in nerve cells [111-115]. The changes following IAA treatment of neural cells are very similar to changes which have been seen in animal models of ischemic stroke [116] and include alterations in membrane potential [115], breakdown of phospholipids [117], loss of ATP and an increase in reactive oxygen species (ROS) [112,117]. A 2 hr treatment of the HT22 cells with 20 μM IAA induces 85-90% cell death, when measured 20 hrs after the addition of IAA. The specific dose of IAA results in a highly reproducible cell death assay, which makes the assay an effective and reproducible screen to test a wide range of drug concentrations. For example, as shown FIGS. 3, 5A-5D and 6, the cell death caused by treatment of HT22 cells with 20 μM IAA can be prevented in a dose dependent fashion by the flavonoids Fisetin and Baicalein.

For the chemical ischemia assay, HT22 cells were plated in 96-well tissue culture dishes at $5 \times 10^3$ cells/well [118, 119]. The following day compounds at 0.5, 2 and 5 μM are added followed by 20 μM IAA. After 2 hr, the medium is replaced with IAA-free medium containing the same concentration of compound. All data points are done in quadruplicate and controls include compound alone for toxicity and compound with no cells for interference with the assay. After 20 hr cell viability is determined by the 3-(4,5-dimethylthiazol-2-yl)-2,5-diphenyltetrazolium bromide (MTT) assay [120]. Positive hits (i.e., protection from IAA toxicity) will be confirmed by visual inspection. The $EC_{50}$ (concentration of a drug that is required for 50% neuroprotection in vitro) were determined and compounds that rescue 50% or more of the cells were subjected to a dose-response curve from 10 nM to 50 μM.

Excitotoxicity cell assay: Primary cultures of cortical neurons that die due to excitotoxicity were prepared as described previously [121]. Briefly, BALB/c mouse embryo cortices were minced and treated with 0.1% trypsin for 20 min. After centrifugation, the cells are resuspended in 827 Neurobasal medium (Invitrogen) plus 10% fetal calf serum and are dissociated by repeated pipetting through a 1 mL blue Eppendorf pipette tip. Then the cells are plated at $1 \times 10^5$ cells per well in 96-well poly-L-lysine and laminin-coated microtiter plates (Becton Dickinson, Bedford, Mass., USA) in 827 Neurobasal plus 10% fetal calf serum and 20% glial growth-conditioned medium. Two days later the medium is aspirated and replaced by serum-free 827 Neurobasal medium plus 10 μg/mL cytosine arabinoside. The cultures are used without media change 11 days after plating and are essentially free of astrocytes. They are exposed to 10 μM glutamate followed by varying concentrations of the compounds. Cell viability is determined 24 h later using the fluorescent live/dead assay. Glial conditioned medium is prepared from confluent rat astrocyte cultures [121]. The cells are washed twice with serum-free medium and incubated for 2 days in serum-free Neurobasal medium to produce the growth conditioned medium.

Example 10

Polyphenol Compounds Useful to Treat and Prevent Ischemia

Compounds derived from any of 3 scaffolds were identified using in vitro stroke screening assays. An iterative process was used to select active neuroprotective compounds. Compounds of interest promoted cell survival with an $EC_{50} \leq 100$ nM in each of the 2 assays below. Compounds increased cell survival to the degree specified for each assay:
(1) ≥80% cell survival in mouse HT22 hippocampal cells in the presence of 20 μM iodoacetic acid (IAA) (in vitro ischemia model). See, Maher, et al., Brain Res. 2007, 1173:117-25.
(2) ≥35% cell survival in primary mouse cortical neurons in the presence of 10 μM glutamate (in vitro excitotoxicity assay). See, Ishige, et al., *Free Radic Biol Med,* 2001, 30(4): p. 433-46.

Table 5 shows the screening activity data for 3 compounds, Fisetin, chlorogenic acid and Baicalein.

TABLE 5

| Compound | Structure | Name | CRITERIA $EC_{50} \leq 100$ (nM) HT22 Cell IAA assay $EC_{50}$ (nM) | CRITERIA ≥80% SURVIVAL HT22 Cell IAA assay (maximal % protection) | CRITERIA ≥35% SURVIVAL Primary Cortical Cell assay- Glutamate (% protection @ 100 nM) |
|---|---|---|---|---|---|
| Fisetin | 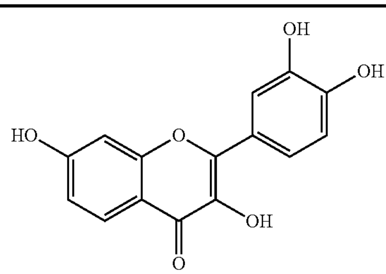 | 3,7,3',4'-tetrahydroxy flavone | 3000 | 90 | 0 |

TABLE 5-continued

| Compound | Structure | Name | CRITERIA $EC_{50} \leq 100$ (nM) HT22 Cell IAA assay $EC_{50}$ (nM) | CRITERIA $\geq 80\%$ SURVIVAL HT22 Cell IAA assay (maximal % protection) | CRITERIA $\geq 35\%$ SURVIVAL Primary Cortical Cell assay-Glutamate (% protection @ 100 nM) |
|---|---|---|---|---|---|
| Chlorogenic Acid | 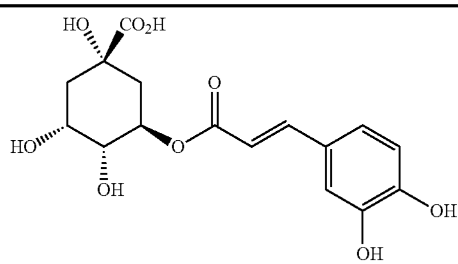 | 1,3,4,5-tetrahydroxycyclohexanecarboxylic acid 3-(3,4-dihydrocinnamate) | 5000 | 45 | 0 |
| Baicalein | 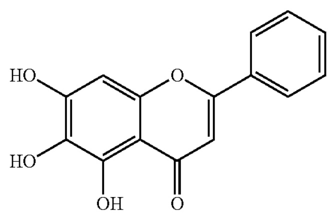 [SMILES: O=c1cc(-c2ccccc2)oc2cc(O)c(O)c(O)c12] | 5,6,7-trihydroxyflavone | 1500 | 85 | 0 |

Table 6 reports details of activity from screens using the IAA HT22 cell assay per (1) above and the primary cortical cell glutamate assay per (2) above. Using the primary screening assays defined above, compounds were identified that increase cell survival to the pre-determined percentages in the criteria set forth in Table 5. Compounds listed in Table 6 were derived from the 3 scaffolds and fulfill criteria stated above.

TABLE 6

| Compound | Structure | Name | HT22 Cell IAA assay $EC_{50}$ (nM) | HT22 Cell IAA assay (% protection @ 100 nM) | Primary Cortical Cell assay-Glutamate (% protection @ 100 nM) |
|---|---|---|---|---|---|
| PM-008 | 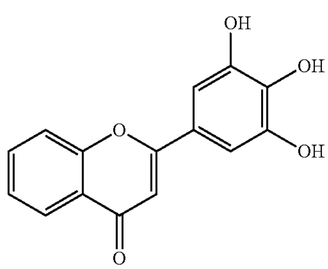 [SMILES: O=c1cc(-c2cc(O)c(O)c(O)c2)oc2ccccc12] | 3',4',5'-trihydroxy flavone | 42 | 88 | 100 |
| PM-010 | 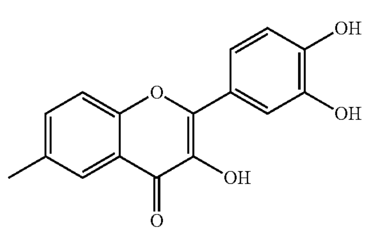 [SMILES: Cc1ccc2oc(-c3ccc(O)c(O)c3)c(O)c(=O)c2c1] | 6-methyl-3,3',4'-trihydroxy flavone | 46 | 89 | 65 |

TABLE 6-continued

| Compound | Structure | Name | HT22 Cell IAA assay EC$_{50}$ (nM) | HT22 Cell IAA assay (% protection @ 100 nM) | Primary Cortical Cell assay-Glutamate (% protection @ 100 nM) |
|---|---|---|---|---|---|
| PM-013 | 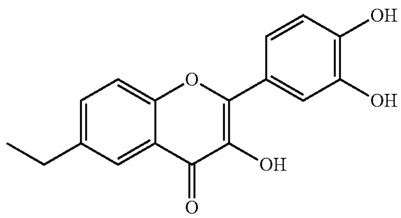 [SMILES: CCc1ccc2oc(-c3ccc(O)c(O)c3)c(O)c(=O)c2c1] | 6-ethyl-3,3',4'-trihydroxy flavone | 61 | 81 | 51 |
| PM-012 | 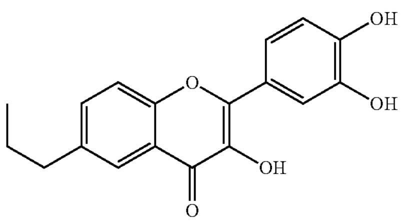 [SMILES: CCCc1ccc2oc(-c3ccc(O)c(O)c3)c(O)c(=O)c2c1] | 6-propyl-3,3',4'-trihydroxy flavone | 38 | 80 | 82 |
| CMS-007 | 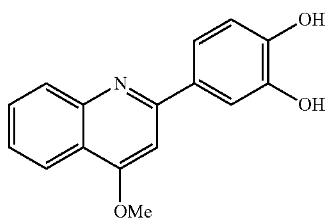 [SMILES: COc1cc(-c2ccc(O)c(O)c2)nc2ccccc12] | 4-methoxy-2-(3,4-dihydroxyphenyl) quinoline | 43 | 71 | ND |
| CMS-011 | 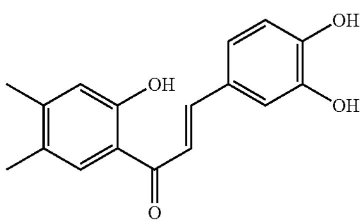 [SMILES: Cc1cc(O)c(C(=O)/C=C/c2ccc(O)c(O)c2)cc1C] | 4',5'-dimethyl-2',3,4-trihydroxychalcone | 53 | 62 | ND |
| CMS-023 | 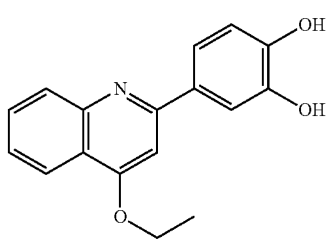 [SMILES: CCOc1cc(-c2ccc(O)c(O)c2)nc2ccccc12] | 4-ethoxy-2-(3,4-dihydroxyphenyl) quinoline | 21 | 72 | 100 |
| CMS-024 | 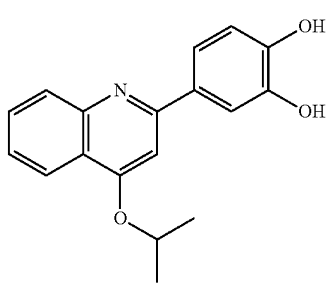 [SMILES: CC(C)Oc1cc(-c2ccc(O)c(O)c2)nc2ccccc12] | 4-isopropoxy-2-(3,4-dihydroxyphenyl) quinoline | 21 | 72 | 58 |

TABLE 6-continued

| Compound | Structure | Name | HT22 Cell IAA assay EC$_{50}$ (nM) | HT22 Cell IAA assay (% protection @ 100 nM) | Primary Cortical Cell assay- Glutamate (% protection @ 100 nM) |
|---|---|---|---|---|---|
| CMS-034 | 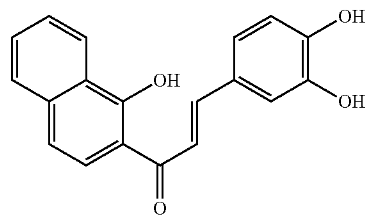 [SMILES: O=C(/C=C/c1ccc(O)c(O)c1)c1ccc2ccccc2c1O] | 2',3,4-trihydroxy alpha-naphthochalcone | 79 | 63 | ND |
| CMS-040 | 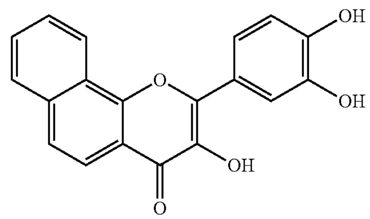 [SMILES: O=c1c(O)c(-c2ccc(O)c(O)c2)oc2c1ccc1ccccc12] | 3,3',4'-trihydroxy alpha-naphthoflavone | 33 | 67 | 86 |
| CMS-059 | 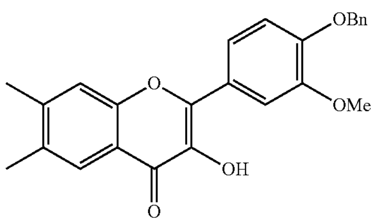 [SMILES: COc1cc(-c2oc3cc(C)c(C)cc3c(=O)c2O)ccc1OCc1ccccc1] | 6,7-dimethyl-3-hydroxy-4'-benzyloxy-3'-methoxyflavone | 167 | 49 | 78 |
| CMS-069 | 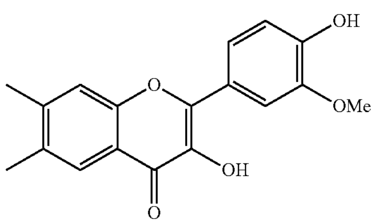 [SMILES: COc1cc(-c2oc3cc(C)c(C)cc3c(=O)c2O)ccc1O] | 3,4'-dihydroxy-3'-methoxyflavone | 36 | 67 | 86 |

Table 7 summarizes structure activity relationship (SAR) data derived from the synthesis and testing of Fisetin-based compounds. The summary described specific chemical modifications that results in enhanced bioactivity using the HT22 cell IAA bioassay. Table 7 also includes 3 compounds that increase survival >80% with EC50≤100 nM in the HT22 cell bioassay (i.e., CMS-034, PM-002, CMS-092).

TABLE 7

STRUCTURE ACTIVITY RELATIONSHIP (SAR)

| S. No. | Compound | Structure | MW | tPSA | CLogP | HT22 Cell IAA assay EC$_{50}$ (nM) |
|---|---|---|---|---|---|---|
| 1 | Fisetin | 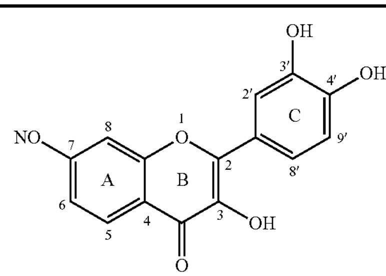 | 286 | 107.2 | 1.24 | 3000 |

TABLE 7-continued
STRUCTURE ACTIVITY RELATIONSHIP (SAR)
| S. No. | Compound | Structure | MW | tPSA | CLogP | HT22 Cell IAA assay EC$_{50}$ (nM) |
|---|---|---|---|---|---|---|
| 2 | PM-004 | 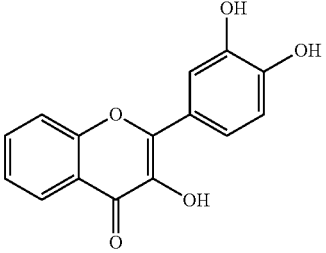 [SMILES: O=c1c(O)c(-c2ccc(O)c(O)c2)oc2ccccc12] | 270 | 87.0 | 1.82 | 500 |
| 3 | PM-001 | 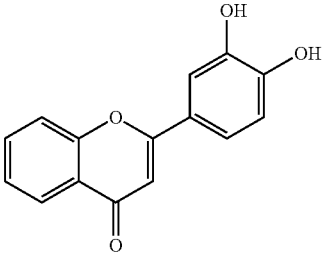 [SMILES: O=c1cc(-c2ccc(O)c(O)c2)oc2ccccc12] | 254 | 66.8 | 2.35 | 500 |
| 4 | PM-008 | 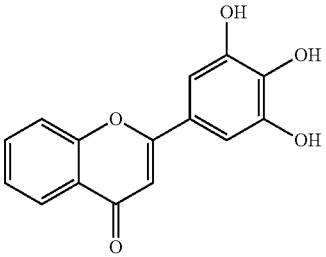 [SMILES: O=c1cc(-c2cc(O)c(O)c(O)c2)oc2ccccc12] | 270 | 87 | 1.70 | 42 |
| 5 | PM-014 | 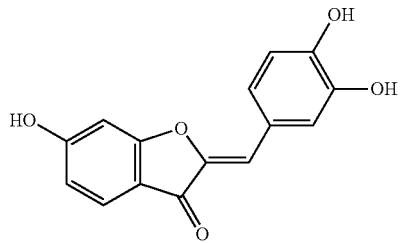 [SMILES: O=C1/C(=C/c2ccc(O)c(O)c2)Oc2cc(O)ccc21] | 270 | 87 | 2.51 | 49 |
| 6 | CMS-034 | 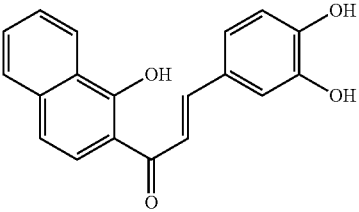 [SMILES: O=C(/C=C/c1ccc(O)c(O)c1)c1ccc2ccccc2c1O] | 306 | 78 | 3.86 | 79 |
| 7 | PM-002 | 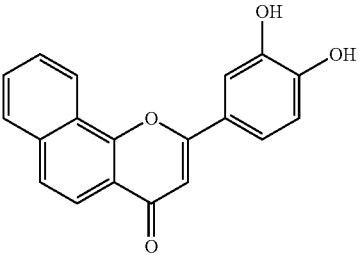 [SMILES: O=c1cc(-c2ccc(O)c(O)c2)oc2c1ccc1ccccc12] | 304 | 66.8 | 3.52 | 80 |

TABLE 7-continued

STRUCTURE ACTIVITY RELATIONSHIP (SAR)

| S. No. | Compound | Structure | MW | tPSA | CLogP | HT22 Cell IAA assay EC$_{50}$ (nM) |
|---|---|---|---|---|---|---|
| 8 | PM-003 | 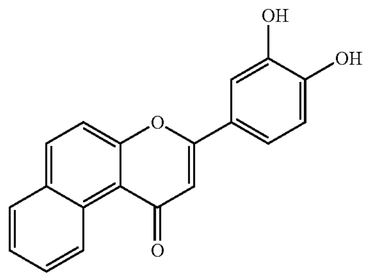 [SMILES: O=c1cc(-c2ccc(O)c(O)c2)oc2ccc3ccccc3c12] | 304 | 66.8 | 3.52 | 80 |
| 9 | CMS-040 | 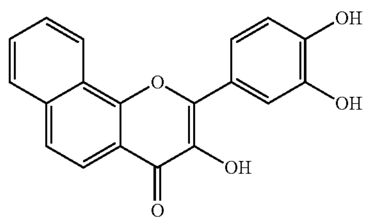 [SMILES: O=c1c(O)c(-c2ccc(O)c(O)c2)oc2c1ccc1ccccc12] | 320 | 87 | 2.99 | 88 |
| 10 | CMS-065 | 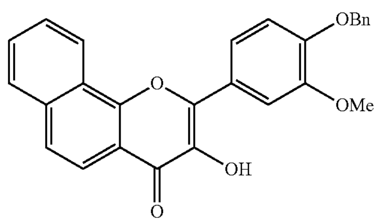 | 424 | 65 | 5.65 | 81 |
| 11 | CMS-072 | 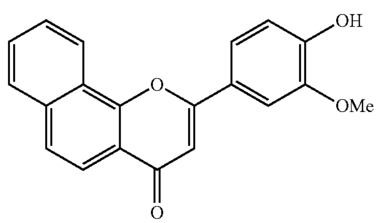 [SMILES: COc1cc(-c2cc(=O)c3ccc4ccccc4c3o2)ccc1O] | 318 | 56 | 3.88 | 44 |
| 12 | PM-010 | 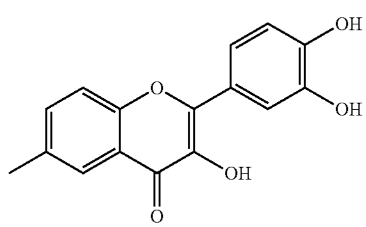 [SMILES: Cc1ccc2oc(-c3ccc(O)c(O)c3)c(O)c(=O)c2c1] | 284 | 87 | 2.31 | 46 |
| 13 | PM-013 | 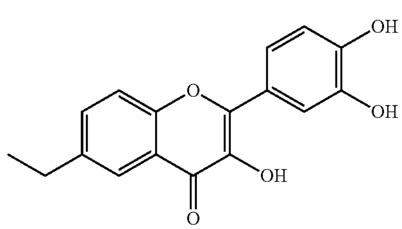 [SMILES: CCc1ccc2oc(-c3ccc(O)c(O)c3)c(O)c(=O)c2c1] | 298 | 87 | 2.84 | 61 |

TABLE 7-continued

STRUCTURE ACTIVITY RELATIONSHIP (SAR)

| S. No. | Compound | Structure | MW | tPSA | CLogP | HT22 Cell IAA assay EC$_{50}$ (nM) |
|---|---|---|---|---|---|---|
| 14 | PM-012 | 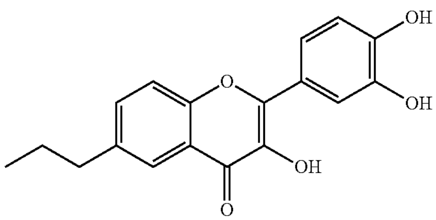 [SMILES: CCCc1ccc2oc(-c3ccc(O)c(O)c3)c(O)c(=O)c2c1] | 312 | 87 | 2.84 | 61 |
| 15 | CMS-011 | 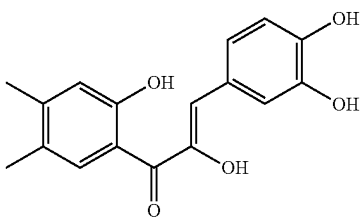 [SMILES: Cc1cc(O)c(C(=O)/C(O)=C/c2ccc(O)c(O)c2)cc1C] | 284 | 78 | 3.64 | 53 |
| 16 | CMS-059 | 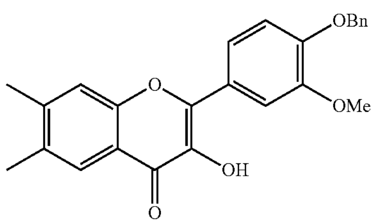 [SMILES: COc1cc(-c2oc3cc(C)c(C)cc3c(=O)c2O)ccc1OCc1ccccc1] | 402 | 65 | 5.42 | 167 |
| 17 | CMS-064 | 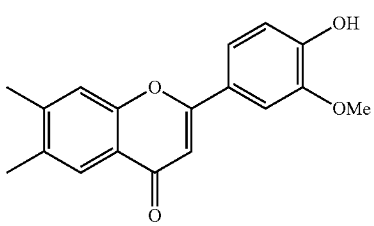 [SMILES: COc1cc(-c2cc(=O)c3cc(C)c(C)cc3o2)ccc1O] | 296 | 56 | 3.66 | 34 |
| 18 | CMS-069 | 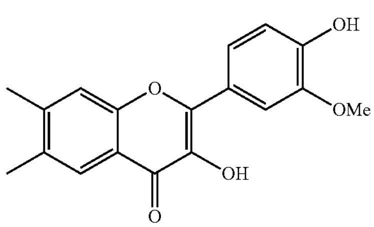 [SMILES: COc1cc(-c2oc3cc(C)c(C)cc3c(=O)c2O)ccc1O] | 312 | 76 | 3.19 | 36 |
| 19 | CMS-078 | 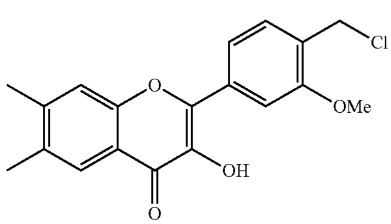 [SMILES: COc1cc(-c2oc3cc(C)c(C)cc3c(=O)c2O)ccc1CCl] | 344 | 55.8 | 4.50 | 134 |

TABLE 7-continued

STRUCTURE ACTIVITY RELATIONSHIP (SAR)

| S. No. | Compound | Structure | MW | tPSA | CLogP | HT22 Cell IAA assay EC$_{50}$ (nM) |
|---|---|---|---|---|---|---|
| 20 | CMS-092 | 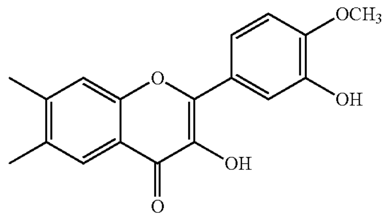 [SMILES: COc1ccc(-c2oc3cc(C)c(C)cc3c(=O)c2O)cc1O] | 312 | 76.0 | 3.19 | 20 |
| 21 | CMS-007 | 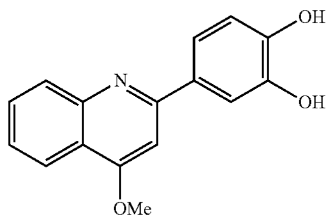 [SMILES: COc1cc(-c2ccc(O)c(O)c2)nc2ccccc12] | 267 | 62 | 3.66 | 12 |
| 22 | CMS-023 | 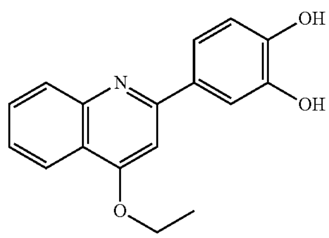 [SMILES: CCOc1cc(-c2ccc(O)c(O)c2)nc2ccccc12] | 281 | 62 | 4.20 | 21 |
| 23 | CMS-024 | 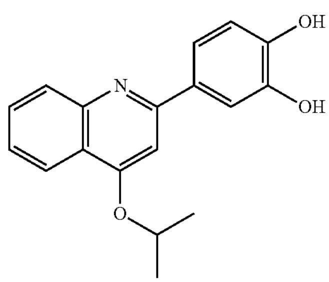 [SMILES: CC(C)Oc1cc(-c2ccc(O)c(O)c2)nc2ccccc12] | 295 | 62 | 4.50 | 21 |
| 24 | CMS-084 | 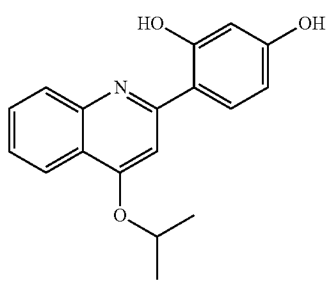 [SMILES: CC(C)Oc1cc(-c2ccc(O)cc2O)nc2ccccc12] | 295 | 62.1 | 4.13 | 210 |

The flavone Fisetin was identified as a lead neuroprotective compound through screening a library of small molecules using a mouse HT22 hippocampal chemical ischemia (IAA toxicity) assay that mimics several important aspects of ischemia and stroke. Fisetin was then modified to improve its potency, physicochemical and absorption, distribution, metabolism, and excretion (ADME) properties and to understand its structure activity relationship (SAR). For example, to enhance brain penetration the CLogP needed to be increased and the tPSA reduced. The initial SAR studies of Fisetin suggested that the absence of a hydroxyl group on the A ring enhances its potency. For example, both compounds 2 (PM-004) and 3 (PM-001) are 6 fold more potent than Fisetin. However, the presence/absence of a hydroxyl group at the 3-position of the B ring does not have an impact on the potency of Fisetin (compare compounds 2 and 3). To further improve the potency of compound 3, multiple hydrophobic groups were added to various positions on the A ring. The addition of methyl groups at the 6 and/or 7 position of the A ring improved the potency ~10-100 fold over Fisetin (e.g.

compound 12 (PM-010)) while the addition of a more hydrophobic naphthalene group (e.g., compounds 7 (PM-002) and 8 (PM-003)) improved the potency ~40 fold over Fisetin and increased the ClogP and reduced the tPSA. SAR studies on the C ring suggested that hydrogen bond accepting groups such as a methoxy at the 4' position and a hydrogen bond donating group such as a hydroxyl at the 3' position further enhanced potency. For example, compounds 17 (CMS-064), 18 (CMS-069) and 20 (CMS-092) are some of the most potent compounds, with $EC_{50}$s below 40 nM. However, since some of the compounds did not increase survival to the specified amount (≥80%), only CMS-092 is a reserve compound. These compounds also have CLogP's and tPSA's consistent with enhanced brain penetration.

The flavone scaffold was also modified, changing it a to quinoline scaffold in order to further improve the potency and physicochemical properties such as CLogP. In certain embodiments, structural elements of the flavone in the quinoline scaffold were reserved, such as hydrogen bond acceptors on the B ring including the quinoline ring 'N' atom and an alkoxy group at the 4-position of the quinoline ring, as well as a 3', 4'-disubstituted C ring. SAR on the quinoline scaffold indicated that more hydrophobic alkoxy groups at the 4-position of the quinoline ring enhanced the potency (isopropoxy~ethoxy>methoxy). Compound 23 (CMS-023) was identified, which is ~140 fold more potent than Fisetin and equally potent as the most active flavone, compound 20 (CMS-092).

In addition to providing SAR, Table 7 provides information of additional compounds that may serve as reserve compounds, e.g., PM-008, CMS-040, PM-010, PM-013, PM-012, CMS-011, CMS-007, CMS-023 and CMS-024. However, other compounds, e.g., CMS-034, PM-002 and CMS-092, have an $EC_{50} \leq 100$ nM in the HT22 cell assay.

Table 8 presents a series of compounds (e.g., CMS-034, CMS-029, PM-002, CMS-117, CMS-118, CMS-121, CMS-129, CMS-139 and CMS-140) that meet criteria in the HT22 cell assay (increase survival>80% with EC50≤100 nM), which include compounds CMS-117, CMS-118, CMS-121, CMS-129, CMS-139 and CMS-140.

TABLE 8

| Compound | Structure | MW | tPSA | CLogP | HT22 Cell IAA assay $EC_{50}$ (nM) | Max Protection |
|---|---|---|---|---|---|---|
| CMS-034 | 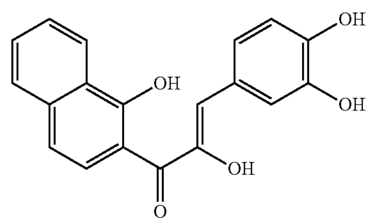 [SMILES: O=C(/C(O)=C/c1ccc(O)c(O)c1)c1ccc2ccccc2c1O] | 306 | 78.0 | 3.86 | 79 | 81% |
| CMS-092 | 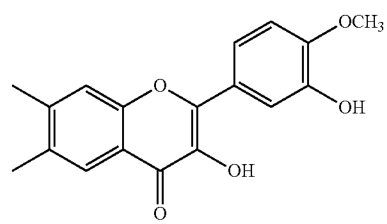 [SMILES: COc1ccc(-c2oc3cc(C)c(C)cc3c(=O)c2O)cc1O] | 312 | 76.0 | 3.19 | 20 | 90% |
| PM-002 | 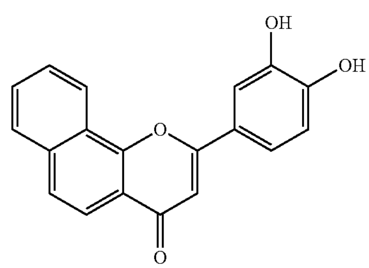 [SMILES: O=c1cc(-c2ccc(O)c(O)c2)oc2c1ccc1ccccc12] | 304 | 66.8 | 3.52 | 80 | 86% |
| CMS-114 | 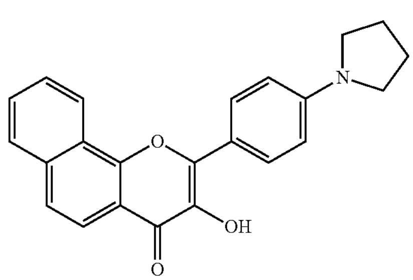 [SMILES: O=c1c(O)c(-c2ccc(N3CCCC3)cc2)oc2c1ccc1ccccc12] | 357 | 49.8 | 4.51 | 71 | 74% |

TABLE 8-continued

| Compound | Structure | MW | tPSA | CLogP | HT22 Cell IAA assay EC$_{50}$ (nM) | Max Protection |
|---|---|---|---|---|---|---|
| CMS-117 | 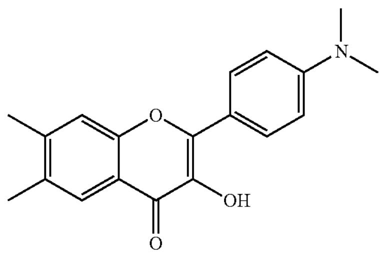 | 309 | 49.8 | 4.17 | 20 | 81% |
| CMS-118 | 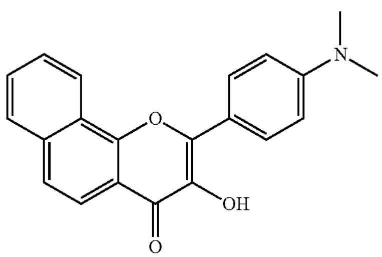 [SMILES: CN(C)c1ccc(-c2oc3c(ccc4ccccc43)c(=O)c2O)cc1] | 331 | 49.8 | 4.40 | 44 | 82% |
| CMS-121 | 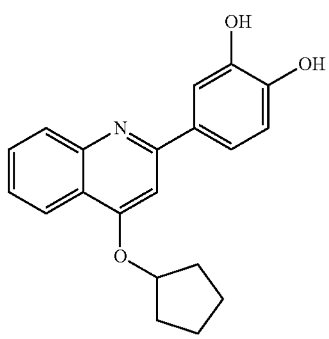 [SMILES: Oc1ccc(-c2cc(OC3CCCC3)c3ccccc3n2)cc1O] | 321 | 62.1 | 5.14 | 7 | 86% |
| CMS-129 | 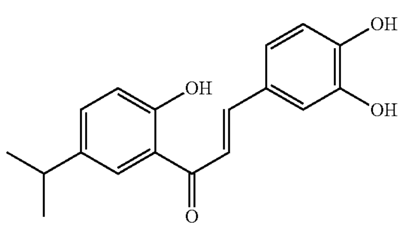 [SMILES: CC(C)c1ccc(O)c(C(=O)/C=C/c2ccc(O)c(O)c2)c1] | 298 | 77.8 | 4.12 | 80 | 81% |
| CMS-137 | 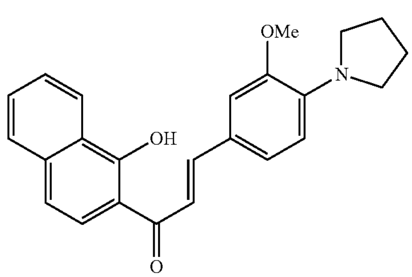 [SMILES: COc1cc(/C=C/C(=O)c2ccc3ccccc3c2O)ccc1N1CCCC1] | 373 | 49.8 | 5.43 | 85 | 75% |

TABLE 8-continued

| Compound | Structure | MW | tPSA | CLogP | HT22 Cell IAA assay EC$_{50}$ (nM) | Max Protection |
|---|---|---|---|---|---|---|
| CMS-138 | 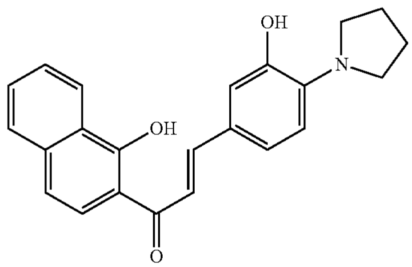 [SMILES: O=C(/C=C/c1ccc(N2CCCC2)c(O)c1)c1ccc2ccccc2c1O] | 359 | 60.8 | 4.74 | 70 | 72% |
| CMS-139 | 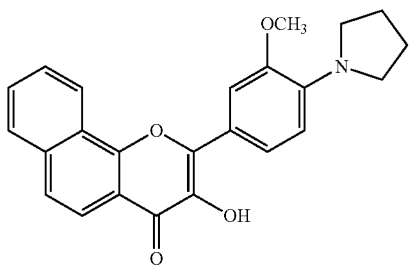 [SMILES: COc1cc(-c2oc3c(ccc4ccccc43)c(=O)c2O)ccc1N1CCCC1] | 387 | 59.0 | 4.53 | 50 | 92% |
| CMS-140 | 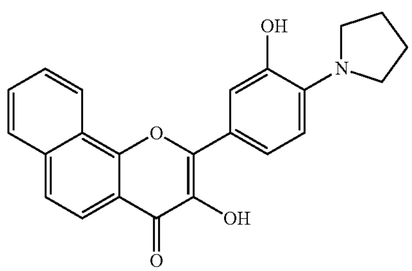 [SMILES: O=c1c(O)c(-c2ccc(N3CCCC3)c(O)c2)oc2c1ccc1ccccc12] | 373 | 70.0 | 3.86 | 10 | 89% |

Select compounds were profiled using the Ames test (See, e.g., Mortelmans, et al., *Mutat. Res.* (2000) 455(1-2): 29-60), CP450 assays and Blood Brain Barrier (BBB) penetration in MDCK cell assay (See, Wang, et al., *Intl. J. Pharmaceutics* (2005) 288(2): 349-359 and Rubin, et al, *J. Cell Biol* (1991) 115(6):1725-35). Compounds of interest meet the following criteria:

(1) The compounds will not be mutagenic in the Ames mutagenicity assay defined at a concentration <10 µM.
(2) The IC$_{50}$ for CYP450 inhibition should be ≥10 µM. This discovery level test will determine how Cytochrome P450 enzymes (CYP4501A2, CYP4502C9, CYP4503A4 and CYP4502D6) interact with the compounds. This test is being done since the enzymatic system responsible for metabolism for excretion and detoxification is mainly the cytochrome P450 system in the liver.
(3) In the MDCK cell assay for blood brain barrier (BBB) penetration, the apparent permeability coefficients (Papp) for both directions will be calculated along with the efflux ratio (Papp B→A/Papp A→B). The potential for BBB penetration will be viewed as:
1) high if Papp A→B≥3.0×10$^{-6}$ cm/s and efflux <3.0;
2) moderate if Papp A÷B≥3.0×10$^{-6}$ cm/s and 10>efflux≥3.0×10$^{-6}$ cm/s;
3) low if Papp A→B≥3.0×10$^{-6}$ cm/s and efflux≥10 or Papp A→B<3.0×10$^{-6}$ cm/s.

The MDCK assay strategy ensures the identification of compounds with good potential to cross the BBB since only compounds in the high and moderate categories will be pursued.

Compounds meeting the selection criteria in the Ames assay, Cytochrome P450 Assay and MDCK Assay are further screened using the CeeTox panel with Ctox ranking as the outcome. See, McKim, *Comb Chem High Throughput Screen.* (2010) 13(2):188-206; McKim, et al., *Cutan Ocul Toxicol.* (2010) 29(3):171-92; and Lapchak and McKim, *Transl Stroke Res.* (2011) 2(1):51-59. CeeTox quantitative measures include the following:
(1) Membrane Integrity (GST or Adenylate Kinase leakage)
(2) Mitochondrial Function measuring MTT and ATP levels:
(3) Cell Proliferation using propidium iodide
(4) Oxidative Stress measuring both GSH and 8-isoprostane
(5) Apoptosis measuring caspase 3 activation
(6) Pgp interaction
(7) Solubility
(8) Microsomal metabolic stability Based upon a CeeTox algorithm, results from the CeeTox Panel of the first 7 assays described above are used to rank-order the compounds based on cytotoxicity, to identify potential subcellular targets and mechanisms of toxicity, and to provide an estimated concentration (the Ctox value) where toxicity would be expected to occur in a rat 14-day in vivo repeat dose study.

The microsomal metabolic stability assay is conducted to determine compound stability. The results are presented separately from the CTox Ranking and defined cut-off criteria are not established since compounds are administered intravenously clinically. Criteria for success: (1) Probability of in vivo effects:

Ctox Ranking (µM) 1-20 high—Do not proceed
21-50 moderate—Proceed
51-300 low—Proceed

REFERENCES

1. NINDS, Tissue plasminogen activator for acute ischemic stroke. The National Institute of Neurological Disorders and Stroke rtPA Stroke Study Group. *N Engl J Med*, 1995. 333(24): p. 1581-7.
2. Albers, G. W., et al., Intravenous tissue-type plasminogen activator for treatment of acute stroke: the Standard Treatment with Alteplase to Reverse Stroke (STARS) study. *JAMA*, 2000. 283(9): p. 1145-50.
3. Alberts, M. J., tPA in acute ischemic stroke: United States experience and issues for the future. *Neurology*, 1998. 51 (3 Suppl 3): p. S53-5.
4. Lapchak, P. A., Development of thrombolytic therapy for stroke: a perspective. *Expert Opin. Investig. Drugs*, 2002. 11 (11): p. 1623-1632.
5. Dirnagl, U., C. Iadecola, and M. A. Moskowitz, Pathobiology of ischaemic stroke: an integrated view. *Trends Neurosci*, 1999. 22(9): p. 391-7.
6. Zivin, J. A., et. al., Tissue plasminogen activator reduces neurological damage after cerebral embolism. *Science*, 1985. 230(4731): p. 1289-92.
7. Lapchak, P. A., 3alpha-OL-5-beta-pregnan-20-one hemisuccinate, a steroidal low-affinity NMDA receptor antagonist improves clinical rating scores in a rabbit multiple infarct ischemia model: synergism with tissue plasminogen activator. *Exp Neurol*, 2006. 197(2): p. 531-7.
8. Lapchak, P. A., D. M. Araujo, and J. A. Zivin, Comparison of Tenecteplase with Alteplase on clinical rating scores following small clot embolic strokes in rabbits. *Exp Neurol*, 2004. 185(1): p. 154-159.
9. Lapchak, P. A., J. Wei, and J. A. Zivin, Transcranial infrared laser therapy improves clinical rating scores after embolic strokes in rabbits. *Stroke*, 2004. 35(8): p. 1985-8.
10. Lapchak, P. A., Memantine, an uncompetitive low affinity NMDA open-channel antagonist improves clinical rating scores in a multiple infarct embolic stroke model in rabbits. *Brain Res*, 2006. 1088(1): p. 141-7.
11. Zivin, J. A., et al., A model for quantitative evaluation of embolic stroke therapy. *Brain Res*, 1987. 435(1-2): p. 305-9.
12. Hacke, W., et al., Thrombolysis in acute ischemic stroke: controlled trials and clinical experience. *Neurology*, 1999. 53(7): p. S3-14.
13. Curry, S. H., Why have so many drugs with stellar results in laboratory stroke models failed in clinical trials? A theory based on allometric relationships. *Ann N Y Acad Sci*, 2003. 993: p. 69-74; discussion 79-81.
14. Hong, H. and G. Q. Liu, Current status and perspectives on the development of neuroprotectants for ischemic cerebrovascular disease. *Drugs Today (Barc)*, 2003. 39(3): p. 213-22.
15. Gladstone, D. J., S. E. Black, and A. M. Hakim, Toward wisdom from failure: lessons from neuroprotective stroke trials and new therapeutic directions. *Stroke*, 2002. 33(8): p. 21 23-36.
16. Liebeskind, D. S. and S. E. Kasner, Neuroprotection for ischaemic stroke: an unattainable goal? *CNS Drugs*, 2001. 15(3): p. 165-74.
17. Muir, K. W. and D. G. Grosset, Neuroprotection for acute stroke: making clinical trials work. *Stroke*, 1999. 30(1): p. 180-2.
18. Lapchak, P. A. and D. M. Araujo, Advances in Ischemic Stroke Treatment: Neuroprotective and Combination Therapies. *Expert Opinion on Emerging Drugs* 2007. 12(1):97-112.
19. O'Collins, V. E., et al., 1,026 experimental treatments in acute stroke. *Ann Neurol*, 2006. 59(3): p. 467-77.
20. Recommendations for standards regarding preclinical neuroprotective and restorative drug development. *Stroke*, 1999. 30(12): p. 2752-8.
21. Lees, K. R., et al., NXY-059 for acute ischemic stroke. *N Engl J Med*, 2006. 354(6): p. 588-600.
22. Lapchak, P. A., et al., Neuroprotective effects of the spin trap agent disodium-[tertbutylimino)methyllbenzene-7,] disulfonate N-oxide (generic NXY-059) in a rabbit small clot embolic stroke model: combination studies with the thrombolytic tissue plasminogen activator. *Stroke*, 2002. 33(5): p. 1411-5.
23. Lapchak, P. A., et al., Coadministration of NXY-059 and tenecteplase six hours following embolic strokes in rabbits improves clinical rating scores. *Exp Neurol*, 2004. 188(2): p. 279-85.
24. Kuroda, S., et al., Neuroprotective effects of a novel nitrone, NXY-059, after transient focal cerebral ischemia in the rat. *J Cereb Blood Flow Metab*, 1999. 19(7): p. 778-87.
25. Lees, K. R., et al., Tolerability of NXY-059 at Higher Target Concentrations in Patients With Acute Stroke. *Stroke*, 2003. 34(2): p. 482-7.
26. Siesjo, B. K., et al., Mechanisms of secondary brain damage in global and focal ischemia: a speculative synthesis. *J Neurotrauma*, 1995. 12(5): p. 943-56.
27. Siesjo, B. K. and P. Siesjo, Mechanisms of secondary brain injury. *Eur J Anaesthesiol*, 1996. 13(3): p. 247-68.
28. Lapchak, P. A. and D. M. Araujo, Advances in hemorrhagic stroke therapy: conventional and novel approaches. *Expert Opin Emerg Drugs*, 2007. 12(3): p. 389-406.
29. Lapchak, P. A. and D. M. Araujo, Advances in ischemic stroke treatment: neuroprotective and combination therapies. *Expert Opin Emerg Drugs*, 2007. 12(1): p. 97-112.
30. Petty, M. A. and J. G. Wettstein, Elements of cerebral microvascular ischaemia. *Brain Res Reviews*, 2004. 36: p. 23-34.
31. Jung, H. A., et al., Antioxidant flavonoids and chlorogenic acid from the leaves of *Eriobotrya japonica*. *Arch Pharm Res*, 1999. 22(2): p. 213-8.
32. Hirose, K. and P. H. Chan, Blockade of glutamate excitotoxicity and its clinical applications. *Neurochem Res*, 1993. 18(4): p. 479-83.
33. Kucukkaya, B., G. Haklar, and A. S. Yalcin, NMDA excitotoxicity and free radical generation in rat brain homogenates: application of a chemiluminescence assay. *Neurochem Res*, 1996. 21(12): p. 1535-8.
34. Mattson, M. P., Neuroprotective signal transduction: relevance to stroke. *Neurosci Biobehav Rev*, 1997. 21(2): p. 193-206.
35. Prass, K. and U. Dirnagl, Glutamate antagonists in therapy of stroke. *Restor Neurol Neurosci*, 1998. 13(1-2): p. 3-10.
36. Facchinetti, F., V. L. Dawson, and T. M. Dawson, Free radicals as mediators of neuronal injury. *Cell Mol Neurobiol*, 1998. 18(6): p. 667-82.
37. Lapchak, P. A., NXY-059. Centaur. *Curr Opin Investig Drugs*, 2002. 3(12): p. 1758-62.
38. Lapchak, P. A. and D. M. Araujo, Spin Trap Agents: A New Approach to Stroke Therapy. *Drug News Perspect*, 2002. 15(4): p. 220-225.

39. Dewar, D., Y. P., and J. McCulloch, Drug development for stroke: importance of protecting cerebral white matter. *Eur J Pharmacol*, 1999. 375: p. 47-50.
40. Fisher, M., The ischemic penumbra: identification, evolution and treatment concepts. *Cerebrovasc Dis*, 2004. 17: p. 1-6.
41. Goldfinger, T. M., Beyond the French paradox: the impact' of moderate beverage alcohol and wine consumption in the prevention of cardiovascular disease. *Cardiol Clin*, 2003. 21(3): p. 449-57.
42. Kar, P., et al., Flavonoid-rich grapeseed extracts: a new approach in high cardiovascular risk patients? *Int J Clin Pract*, 2006. 60(11): p. 1484-92.
43. Nijveldt, R. J., et al., Flavonoids: a review of probable mechanisms of action and potential applications. *Am J Clin Nutr*, 2001. 74(4): p. 418-25.
44. Renaud, S. and J. C. Ruf, The French paradox: vegetables or wine. *Circulation*, 1994. 90(6): p.3118-9.
45. Manach, C., et at., Polyphenols: food sources and bioavailability. *Am J Clin Nutr*, 2004. 79(5): p. 727-47.
46. Scalbert, A., et al. Dietary polyphenols and the prevention of diseases. *Crit Rev Food Sci Nutr*, 2005. 45(4): p 287-306.
47. Dajas, F., et al., Neuroprotection by flavonoids. *Braz J Med Biol Res*, 2003. 36(12): p. 1613-1620.
48. Baur, J. A. and D. A. Sinclair, Therapeutic potential of resveratrol: the in vivo evidence. *Nat Rev Drug Discov*, 2006. 5(6): p. 493-506.
49. Ramassamy, C., Emerging role of polyphenolic compounds in the treatment of neurodegenerative diseases: a review of their intracellular targets. *Eur J Pharmacol*, 2006, 545(1): p. 51-64.
50. Dajas, F., et al., Cell culture protection and in vivo neuroprotective capacity of flavonoids. *Neurotox Res*, 2003. 5(6): p. 425-32.
51. Rivera, F., et al., Some aspects of the in vivo neuroprotective capacity of flavonoids: bioavailability and structure-activity relationship. *Neurotox Res*, 2004. 6(7-8): p. 543-53.
52. Woodman, O. L. and E. Chan, Vascular and anti-oxidant actions of flavonols and flavones. *Clin Exp Pharmacol Physiol*, 2004. 31(11): p. 786-90.
53. Ishige, K., D. Schubert, and Y. Sagara, Flavonoids protect neuronal cells from oxidative stress by three distinct mechanisms. *Free Radic Biol Med*, 2001. 30(4): p. 433-46.
54. Auddy, B., et al., Screening of antioxidant activity of three Indian medicinal plants, traditionally used for the management of neurodegenerative diseases. *J Ethnopharmacol*, 2003. 84(2-3): p. 131-8.
55. Lao, C. J., et al., Microglia, apoptosis and interleukin-1beta expression in the effect of sophora *japonica* I. on cerebral infarct induced by ischemia-reperfusion in rats. *Am J Chin Med*, 2005. 33(3): p. 425-38.
56. Sinha, K., G. Chaudhary, and Y. K. Gupta, Protective effect of resveratrol against oxidative stress in middle cerebral artery occlusion model of stroke in rats. *Life Sci*, 2002. 71 (6): p. 655-65.
57. Huang, S. S., et al., Resveratrol reduction of infarct size in Long-Evans rats subjected to focal cerebral ischemia. *Life Sci*, 2001. 69(9): p. 1057-65.
58. Ikeda, K., H. Negishi, and Y. Yamori, Antioxidant nutrients and hypoxia/ischemia brain injury in rodents. *Toxicology*, 2003. 189(1-2): p. 55-61.
59. Yen, W. J., et al., Antioxidant properties of roasted coffee residues. *J Agric Food Chem*, 2005. 53(7): p. 2658-63.
60. Zheng, W. and S. Y. Wang, Oxygen radical absorbing capacity of phenolics in blueberries, cranberries, chokeberries, and lingonberries. *J Agric Food Chem*, 2003. 51(2): p. 502-9.
61. Aruoma, O. I., Antioxidant actions of plant foods: use of oxidative DNA damage as a tool for studying antioxidant efficacy. *Free Radic Res*, 1999. 30(6): p. 419-27.
62. Chassevent, F., [Chlorogenic acid, physiological and pharmacological activity]. *Ann Nutr Aliment*, 1969. 23(1): p. Suppl: 1-14.
63. Farah, A., et al., Chlorogenic acids and lactones in regular and water-decaffeinated Arabica coffees. *J Agric Food Chem*, 2006. 54(2): p. 374-81.
64. Farah A, D. C., Phenolic compounds in coffee. *Br J Plant Physiol*, 2006. 18(1): p. 23-36.
65. dos Santos, M. D., et al., Evaluation of the anti-inflammatory, analgesic and antipyretic activities of the natural polyphenol chlorogenic acid. *Biol Pharm Bull*, 2006. 29(11): p. 2236-40.
66. Jin, U. H., et al., A phenolic compound, 5-caffeoylquinic acid (chlorogenic acid), is a new type and strong matrix metalloproteinase-9 inhibitor: isolation and identification from methanol extract of *Euonymus alatus*. *Life Sci*, 2005. 77(22): p. 2760-9.
67. Lapchak, P. A. and D. M. Araujo, Reducing bleeding complications after thrombolytic therapy for stroke: clinical potential of metalloproteinase inhibitors and spin trap agents. *CNS Drugs*, 2001. 15(11): p. 819-29.
68. Lapchak, P. A., D. F. Chapman, and J. A. Zivin, Metalloproteinase inhibition reduces thrombolytic (tissue plasminogen activator)-induced hemorrhage after thromboembolic stroke. *Stroke*, 2000. 31(12): p. 3034-40.
69. Montaner, J., et al., Matrix metalloproteinase expression is related to hemorrhagic transformation after cardioembolic stroke. *Stroke*, 2001. 32(12): p. 2762-7.
70. Montaner, J., et al., Matrix metalloproteinase-9 pretreatment level predicts intracranial hemorrhagic complications after thrombolysis in human stroke. *Circulation*, 2003. 107(4): p. 598-603.
71. Rosenberg, G. A., Matrix metalloproteinases in brain injury. *J Neurotrauma*, 1995. 12(5): p. 833-42.
72. Rosenberg, G. A., et al, Immunohistochemistry of matrix metalloproteinases in reperfusion injury to rat brain: activation of MMP-9 linked to stromelysin-1 and microglia in cell cultures. *Brain Res*, 2001. 893(1-2): p. 104-12.
73. Rosenberg, G. A., et al., Tumor necrosis factor-alpha-induced gelatinase B causes delayed opening of the blood-brain barrier: an expanded therapeutic window. *Brain Res*, 1995. 703(1-2): p. 151-5.
74. Rosenberg, G. A. and M. Navratil, Metalloproteinase inhibition blocks edema in intracerebral hemorrhage in the rat. *Neurology*, 1997. 48(4): p. 921-6.
75. Lotito, S. B. and B. Frei, Consumption of flavonoid-rich foods and increased plasma antioxidant capacity in humans: Cause, consequence, or epiphenomenon? *Free Radic Biol Med*, 2006. 41 (12): p. 1727-46.
76. Maher, P. and D. Schubert, Signaling by reactive oxygen species in the nervous system. *Cell Mol Life Sci*, 2000. 57(8-9): p. 1287-305.
77. Shimizu, T. and L. S. Wolfe, Arachidonic acid cascade and signal transduction. *J Neurochem*, 1990. 55(1): p. 1-15.
78. van Leyen, K., et al., Novel lipoxygenase inhibitors as neuroprotective reagents. *J Neurosci Res*, 2008. 86(4): p. 904-9.
79. Shornick, L. P. and M. J. Holtzman, A cryptic, microsomal-type arachidonate 12-lipoxygenase is tonically inactivated by oxidation-reduction conditions in cultured epithelial cells. *J Biol Chem*, 1993. 268(1): p. 371-6.
80. Li, Y., P. Maher, and D. Schubert, A role for 12-lipoxygenase in nerve cell death caused by glutathione depletion. *Neuron*, 1997. 19: p. 453-463.
81. Mori, H., et al., Neuroprotective effects of pterin-6-aldehyde in gerbil global brain ischemia: comparison with those of alpha-phenyl-N-tert-butyl nitrone. *Neurosci Lett*, 1998. 241 (2-3): p. 99-102.
82. Hwang, Y. S., et al., Hwangryun-Hae-Dok-tang (Huan-glian-Jie-Du-Tang) extract and its constituents reduce ischemia-reperfusion brain injury and neutrophil infiltration in rats. *Life Sci*, 2002. 71(18): p. 2105-17.
83. Huang, M. T., et al , Inhibitory effect of curcumin, chlorogenic acid, caffeic acid, and ferulic acid on tumor promotion in mouse skin by 12-0-tetradecanoylphorbol-13-acetate. *Cancer Res*, 1988. 48(21): p. 5941-6.
84. Middleton, E., C. Kandaswami, and T. C. Theoharides, The effects of plant flavonoids on mammalian cells: implications for inflammation, heart disease and cancer. *Pharmacol. Rev.*, 2000. 52: p. 673-751.
85. Sekiya, K. and H. Okuda, Selective inhibition of platelet lipoxygenase by Baicalein. *Biochem Biophys Res Commun*, 1982. 105(3): p. 1090-5.
86. Yoon, J. H. and S. J. Baek, Molecular targets of dietary polyphenols with anti-inflammatory properties. *Yonsei Med J*, 2005. 46(5): p. 585-96.
87. van Leyen, K., et al., Baicalein and 12/15-lipoxygenase in the ischemic brain. *Stroke*, 2006. 37(12): p. 3014-8.
88. Marcheselli, V. L., et al., Novel docosanoids inhibit brain ischemia-reperfusion-mediated leukocyte infiltration and pro-inflammatory gene expression. *J Biol Chem*, 2003. 278(44): p. 43807-17.
89. Zhang, B., H. Cao, and G. N. Rao, 15(S)-hydroxyeicosatetraenoic acid induces angiogenesis via activation of P13K-Akt-mTOR-S6K1 signaling. *Cancer Res*, 2005. 65(16): p. 7283-91.
90. Jin, G., et al., Protecting against cerebrovascular injury: contributions of 12/15-lipoxygenase to edema formation after transient focal ischemia. *Stroke*, 2008. 39(9): p. 2538-43.
91. Zivin, J. A. and D. R. Waud, Quantal bioassay and stroke. *Stroke*, 1992. 23(5): p. 767-73.
92. Abe, K., M. Takayanagi, and H. Saito, Effects of recombinant human basic FGF and its modified protein CS23 on survival of primary cultured neurons from various regions of fetal rat brain. *Japan J. Pharmacol.*, 1990. 53: p. 221-227.
93. Lee, H. H., et al., Differential effects of natural polyphenols on neuronal survival in primary cultured central neurons against glutamate- and glucose deprivation-induced neuronal death. *Brain Res*, 2003. 986(1-2): p. 103-13.
94. Lapchak, P. A. and J. A. Zivin, Ebselen, a seleno-organic antioxidant, is neuroprotective after emoblic strokes in rabbits—Synergism with low dose tissue plasminogen activator. *Stroke*, 2003. 34: p. 2013-2018.
95. Lapchak, P. A., et al., Transcranial near-infrared light therapy improves motor function following embolic strokes in rabbits: An extended therapeutic window study using continuous and pulse frequency delivery modes. *Neuroscience*, 2007. 148(4): p. 907-914.
96. Lapchak, P. A., et al., Effects of the spin trap agent disodium-[tert-butylimino)methyl]benzene-1,3-disulfonate N-oxide (generic NXY-059) on intracerebral hemorrhage in a rabbit Large clot embolic stroke model: combination studies with tissue plasminogen activator. *Stroke*, 2002. 33(6): p. 1665-70.
97. Choudhri, T. F., et al., Use of a spectrophotometric hemoglobin assay to objectively quantify intracerebral hemorrhage in mice. *Stroke*, 1997. 28(1,1): p. 2296-302.
98. Waud, D. R., On biological assays involving quantal responses. *Journal of Pharmacological Experimental Theory*, 1972. 183: p. 577-607.
99. Winer, B. J., Statistical Principles In Experimental Design. 2 ed. 1971, New York: McGraw Hill. 907.
100. Snedecor, G. W. and W. G. Cochran, Statistical Methods. 7 ed. 1980, Ames, Iowa: Iowa State University Press. 507.
101. Maher, P., et al., A novel approach to screening for new neuroprotective compounds for the treatment of stroke. *Brain Res*, 2007. 1173: p. 117-25.
102. Silverman, R., The Organic Chemistry of Drug Design and Drug Action. 2004: Academic Press.
103. Liao, H. L. and M. K. Hu, Synthesis and anticancer activities of 5,6,7-trimethylBaicalein derivatives. *Chem Pharm Bull* (Tokyo), 2004. 52(10): p. 1162-5.
104. Harikrishnan, L. S. and H. D. Hollis Showalter, A novel synthesis of 2,3-disubstituted benzopyran-4-onbes and application to the solid phase. *Tetrahedron Letters*, 2000. 56: p. 515-19.
105. Vazquez, J. and F. Albericia, A convenient semicarbazide resin for the solid-phase synthesis of peptide ketones and aldehydes. *Tetrahedron Letters*, 2006. 47: p. 1657-1661.
106. Lawrence, N. J., et al., Linked parallel synthesis and MTT bioassay screening of substituted chalcones. *J Comb Chem*, 2001. 3(5): p. 421-6.
107. Lin, Y. M., et al., Chalcones and flavonoids as anti-tuberculosis agents. *Bioorg Med Chem*, 2002. 10(8): p. 2795-802.
108. Razgulin, A. V. and S. Mecoui, Binding properties of aromatic carbon-bound fluorine. *J Med Chem*, 2006. 49(26): p. 7902-6.
109. Weber, J., Current status of virtual combinatorial library design. *QSAR & Combinatorial Science*, 2005. 24(7): p. 809-823.
110. Sefkow, M., First efficient synthesis of chlorogenic acid. *Eur J Org Chem*, 2001 (6): p. 1137-41.
111. Reshef, A., O. Sperling, and E. Zoref-Shani, Activation and inhibition of protein kinase C protect rat neuronal cultures against ischemia-reperfusion insult. *Neurosci Lett*, 1997. 238(1-2): p. 37-40.
112. Sperling, O., et al., Reactive oxygen species play an important role in iodoacetate-induced neurotoxicity in primary rat neuronal cultures and in differentiated PC12 cells. *Neurosci Lett*, 2003. 351 (3): p. 137-40.
113. Rego, A. C., et al., Distinct glycolysis inhibitors determine retinal cell sensitivity to glutamatemediated injury. *Neurochem Res*, 1999. 24(3): p. 351-8.
114. Sigalov, E., et al., VIP-Related protection against lodoacetate toxicity in pheochromocytoma (PC12) cells: a model for ischemic/hypoxic injury. *J Mol Neurosci*, 2000. 15(3): p. 147-54.
115. Reiner, P. B., A. G. Laycock, and C. J. Doll, A pharmacological model of ischemia in the hippocampal slice. *Neurosci Lett*, 1990. 11 9(2): p. 175-8.
116. Magnoni, S., et al., Alpha-melanocyte-stimulating hormone is decreased in plasma of patients with acute brain injury. *J Neurotrauma*, 2003. 20(3): p. 251-60.
117. Crack, P. J., et al., Potential contribution of NF-kappa6 in neuronal cell death in the glutathione peroxidase-I knockout mouse in response to ischemia-reperfusion injury. *Stroke*, 2006. 37(6): p. 1533-8.

118. Li, Y., P. Maher, and D. Schubert, A role for 12-lipoxygenase in nerve cell death caused by glutathione depletion. *Neuron*, 1997. 19(2): p. 453-63.

119. Li, Y., P. Maher, and D. Schubert, Phosphatidylcholine-specific phospholipase C regulates glutamate-induced nerve cell death. *Proc Natl Acad Sci U S A*, 1998. 95(13): p. 7748-53.

120. Hansen, M. B., S. E. Nielsen, and K. Berg, Re-examination and further development of a precise and rapid dye method for measuring cell growth/cell kill. *J Immunol Methods*, 1989. 11 9(2): p. 203-10.

121. Schubert, D. and D. Piasecki, Oxidative glutamate toxicity can be a component of the excitotoxicity cascade. *J Neurosci*, 2001. 21 (1 9): p. 7455-62.

122. Maron, D. M. and B. N. Ames, Revised methods for the *Salmonella* mutagenicity test. *Mutat Res*, 1983. 113(3-4): p. 173-215.

123. Wang, Q., et al., Evaluation of the MDR-MDCK cell line as a permeability screen for the blood-brain barrier. *Int J Pharm*, 2005. 288(2): p. 349-59.

124. MacLellan, C. L., et al., The influence of hypothermia on outcome after intracerebral hemorrhage in rats. *Stroke*, 2006. 37(5): p. 1266-70.

125. Bederson, J. B., et al., Evaluation of 2,3,5-triphenyltetrazolium chloride as a stain for detection and quantification of experimental cerebral infarction in rats. *Stroke*, 1986. 17(6): p. 1304-8.

126. Gundersen, H. J. G., et al., The new stereological tools: Disector, fractionator, nucleator and point sampled intercepts and their use in pathological research and diagnosis. *APMIS*, 1988. 96: p. 857-881.

127. Triguero, D., J. Buciak, and W. M. Pardridge, Capillary depletion method for quantification of blood-brain barrier transport of circulating peptides and plasma proteins. *J Neurochem*, 1990. 54(6): p. 1882-8.

128. Wiebers, D. O., H. P. Adams, Jr., and J. P. Whisnant, Animal models of stroke: are they relevant to human disease? *Stroke*, 1990. 21(1): p. 1-3.

129. Zivin, J. A. and J. C. Grotta, Animal stroke models. They are relevant to human disease. *Stroke*, 1990. 21(7): p. 981-3.

130. Grotta, J., Rodent models of stroke limitations. What can we learn from recent clinical trials of thrombolysis? *Arch Neurol*, 1996. 53(10): p. 1067-70.

131. Ginsberg, M. D., The validity of rodent brain-ischemia models is self-evident. *Arch Neurol*, 1996. 53(10): p. 1065-7; discussion 1070.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:
1. A compound having a formula I

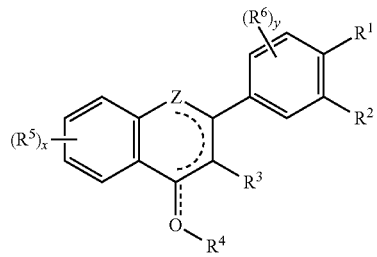

or a structure selected from

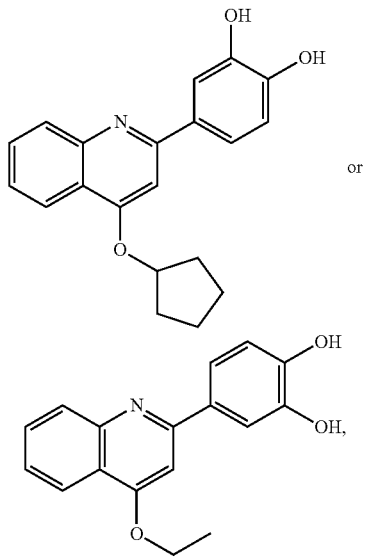

or a pharmaceutically acceptable salt thereof, wherein:
Z is N and

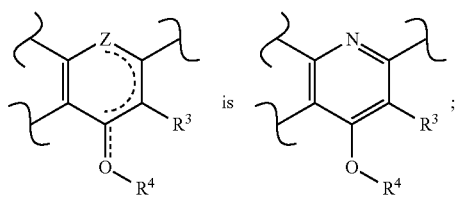

$R^1$ is —N($R^c$)$_2$;
$R^2$ is H, optionally substituted $C_{1-6}$alkyl, —OR$^a$, —NO$_2$ or —N($R^c$)$_2$;
$R^3$ is H, optionally substituted $C_{1-6}$alkyl or —OR$^a$;
$R^4$ is $C_{1-6}$alkyl;
each $R^5$ is, independently for each occurrence, $R^e$, $R^b$, $R^e$ substituted with one or more of the same or different $R^a$ and/or $R^b$, —OR$^e$ substituted with one or more of the same or different $R^a$ and/or $R^b$, —SR$^e$ substituted with one or more of the same or different $R^a$ and/or $R^b$, —C(O)R$^e$ substituted with one or more of the same or different $R^a$ and/or $R^b$, —N($R^a$)R$^e$ where $R^e$ is substituted with one or more of the same or different $R^a$ and/or $R^b$, —$(C(R^a)_2)_m$—$R^b$, —O—$(C(R^a)_2)_m$—$R^b$, —S—$(C(R^a)_2)_m$—$R^b$, —O—$(C(R^b)_2)_m$—$R^a$, —N($R^a$)—$(C(R^a)_2)_m$—$R^b$, —O—$(CH_2)_m$—CH$((CH_2)_mR^b)R^b$, —C(O)N($R^a$)—$(C(R^a)_2)_m$—$R^b$, —O—$(C(R^a)^2)_m$—C(O)N($R^a$)—$(C(R^a)_2)_m$—$R^b$, —N((C($R^a$)_2)_mR^b)_2$, —S—$(C(R^a)_2)_m$—C(O)N($R^a$)—$(C(R^a)_2)_m$—$R^b$, —N($R^a$)—C(O)—N($R^a$)—$(C(R^a)_2)_m$—$R^b$, —N($R^a$)—C(O)—$(C(R^a)_2)_m$—C($R^a$)($R^b)_2$ or —N($R^a$)—$(C(R^a)_2)_m$—C(O)—N($R^a$)—$(C(R^a)_2)_m$—$R^b$, or, alternatively, two of $R^5$, together with the vicinal carbons to which they are attached, combine to form a 4-10 membered unsaturated, or partially saturated mono or bicyclic ring, optionally containing one or more heteroatoms and optionally substituted with one or more $R^a$ and/or $R^b$;

each $R^6$ is, independently for each occurrence, $R^e$, $R^b$, $R^e$ substituted with one or more of the same or different $R^a$ and/or $R^b$, —$OR^e$ substituted with one or more of the same or different $R^a$ and/or $R^b$, —$SR^e$ substituted with one or more of the same or different $R^a$ and/or $R^b$, —C(O)$R^e$ substituted with one or more of the same or different $R^a$ and/or $R^b$, —N($R^a$)$R_e$ where $R^e$ is substituted with one or more of the same or different $R^a$ and/or $R^b$, —$(C(R^a)_2)_m$—$R^b$, —O—$(C(R^a)_2)_m$—$R^b$, —S—$(C(R^a)_2)_m$—$R^b$, —O—$(C(R^b)_2)_m$—$R^a$, —N($R^a$)—$(C(R^a)_2)_m$—$R^b$, —O—$(CH_2)_m$—CH$((CH_2)_mR^b)R^b$, —C(O)N($R^a$)—$(C(R^a)_2)_m$—$R^b$, —O—$(C(R^a)_2)_m$—C(O)N($R^a$)—$(C(R^a)_2)_m$—$R^b$, —N($(C(R^a)_2)_mR^b)_2$, —S—$(C(R^a)_2)_m$—C(O)N($R^a$)—$(C(R^a)_2)_m$—$R^b$, —N($R^a$)—C(O)—N($R^a$)—$(C(R^a)_2)_m$—$R^b$, —N($R^a$)—C(O)—$(C(R^a)_2)_m$—C($R^a$)($R^b)_2$ or —N($R^a$)—$(C(R^a)_2)_m$—C(O)—N($R^a$)—$(C(R^a)_2)_m$—$R^b$, or, alternatively, two of $R^6$, together with the vicinal carbons to which they are attached, combine to form a 4-10 membered unsaturated, or partially saturated mono or bicyclic ring, optionally containing one or more heteroatoms and optionally substituted with one or more $R^a$ and/or $R^b$;

each $R^a$ is independently for each occurrence H, $C_{1-6}$alkyl, $C_{4-11}$cycloalkylalkyl, $C_{6-10}$aryl, $C_{7-16}$arylalkyl, 3-10 membered heteroalicyclyl, 4-11 membered heteroalicyclylalkyl, 5-15 membered heteroaryl or 6-16 membered heteroarylalkyl;

each $R^b$ is independently for each occurrence =O, =S, —$OR^a$, —O—$(C(R^a)_2)_m$—$OR^a$, —$SR^a$, =$NR^a$, =$NOR^a$, —N($R^c)_2$, halo, —$CF_3$, —CN, —$NO_2$, —S(O)$R^a$, —S(O)$_2R^a$, —SO$_3R^a$, —S(O)$_2$N($R^a)_2$, —C(O)$R^a$, —CO$_2R^a$, —C(O)N($R^c)_2$, —OC(O)N($R^c)_2$, —[N($R^a$)C(O)]$_nR^a$, —[N($R^a$)C(O)]$_nOR^a$ or —[N($R^a$)C(O)]$_n$N($R^c)_2$;

each $R^c$ is independently for each occurrence $R^a$, or, alternatively, two $R^C$ are taken together with the nitrogen atom to which they are bonded to form a 3 to 10-membered heteroalicyclyl or a 5-10 membered heteroaryl which may optionally include one or more of the same or different additional heteroatoms and which is optionally substituted with one or more of the same or different $R^a$ and/or $R^d$ groups;

each $R^d$ is =O, —$OR^a$, halo$C_{1-3}$alkyloxy, $C_{1-6}$alkyl, =S, —$SR^a$, —N($R^a)_2$, halo, —$CF_3$, —CN, —$NO_2$, —S(O)$R^a$, —S(O$_2$)$R^a$, —SO$_3R^a$, —S(O)$_2$N($R^a)_2$, —C(O)$R^a$, —CO$_2R^a$, —C(O)N($R^a)_2$, —OC(O)N($R^a)_2$, —[N($R^a$)C(O)]$_nR^a$, —$(C(R^a)_2)_n$—$OR^a$, —C(O)—$C_{1-6}$haloalkyl, —OC(O)$R^a$, —O(C($R^a)_2)_m$—$OR^a$, —S(C($R^a)_2)_m$—$OR^a$, —N($R^a$)—$(C(R^a)_2)_m$—$OR^a$, —[N($R^a$)C(O)]$_nOR^a$, —[N($R^a$)C(O)]$_n$N($R^a)_2$ or —N($R^a$)C(O)$C_{1-6}$haloalkyl, or, alternatively, two $R^d$, taken together with the atom or atoms to which they are attached, combine to form a 3-10 membered partially or fully saturated mono or bicyclic ring, optionally containing one or more heteroatoms and optionally substituted with one or more $R^a$;

each $R^e$ is independently for each occurrence $C_{1-6}$alkyl, $C_{4-11}$cycloalkylalkyl, $C_{6-10}$aryl, $C_{7-16}$arylalkyl, 3-10 membered heteroalicyclyl, 4-11 membered heteroalicyclylalkyl, 5-15 membered heteroaryl or 6-16 membered heteroarylalkyl;

each m is 1, 2 or 3;

each n is 0, 1, 2 or 3;

x is 0, 1, 2, 3 or 4; and y is 0, 1, 2 or 3.

2. The compound of claim 1, according to Formula IIA

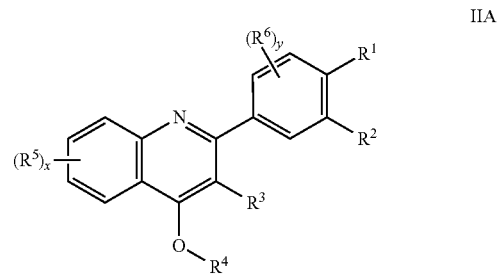

IIA wherein:

each $R^5$ is, independently for each occurrence, $C_{1-6}$alkyl, $C_{4-11}$cycloalkylalkyl, $C_{6-10}$aryl, $C_{7-16}$arylalkyl, —$OR^a$, —O—$(C(R^a)_2)_m$—$OR^a$, —$SR^a$, —N($R^c)_2$, halo, —$CF_3$, —$CO_2R^a$, —C(O)N($R^c)_2$, or two of $R^5$, together with the vicinal carbons to which they are attached, combine to form a 6-membered unsaturated aryl ring, the 6-membered aryl ring optionally substituted with one or more $R^a$ and/or $R^b$; and each $R^6$ is, independently for each occurrence, $C_{1-6}$alkyl, $C_{4-11}$cycloalkylalkyl, $C_{6-10}$aryl, $C_{7-16}$arylalkyl, —$OR^a$, —O—$(C(R^a)_2)_m$—$OR^a$, —$SR^a$, —N($R^c)_2$, halo, —$CF_3$, —$CO_2R^a$, —C(O)N($R^c)_2$.

3. The compound of claim 2, wherein:

(a) the compound is of Formula IIA; $R^2$ is —$OR^a$; and $R^3$ is H or optionally substituted $C_{1-6}$alkyl; or (b) the compound is of Formula IIA; $R^2$ is H; and $R^3$ is H or optionally substituted $C_{1-6}$alkyl.

4. The compound of claim 1, wherein $R^2$ is H or OH.

5. The compound of claim 2, wherein the compound is of Formula IIA, $R^2$ is —$OR^a$, and $R^3$ is H.

6. The compound of claim 5, wherein $R^2$ is —OH.

7. The compound according to claim 1, wherein the compound is:

4-ethoxy-2-(3,4-dihydroxyphenyl)quinoline (CMS-023);

4-cyclopentyloxy-2-(3,4-dihydroxyphenyl)quinoline (CMS-121);

4-methoxy-2-(4-dimethylaminophenyl)quinoline (CMS-109);

4-methoxy-2-(4-(pyrrolidin-1-yl)phenyl)quinoline (CMS-110);

4-isopropoxy-2-(4-dimethylaminophenyl)quinoline (CMS-112); or 4-isopropoxy-2-(4-(pyrrolidin-1-yl)phenyl)quinoline (CMS-113).

8. The compound of claim 1, wherein the compound is

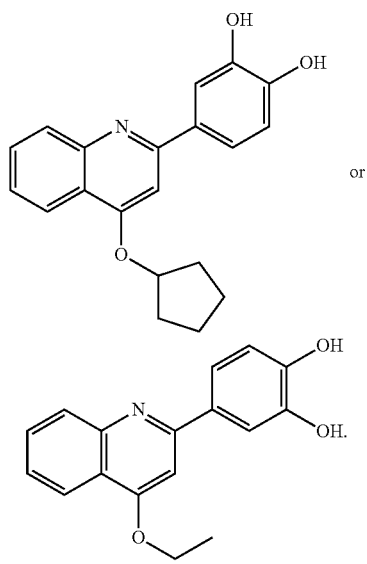

or

9. A pharmaceutical composition comprising one or more compounds of claim 1, and a pharmaceutically acceptable carrier, excipient or vehicle.

10. A method of promoting, increasing, and/or enhancing the protection, growth and/or regeneration of neurons, comprising administering an effective amount of one or more compounds of claim 1 to the neurons.

11. The method of claim 10 wherein the method promotes, increases, and/or enhances the protection, growth and/or regeneration of neurons by maintaining glutathione levels.

12. The compound of claim 1, wherein $R^4$ is $C_{3-6}$cycloalkyl.

13. The compound of claim 1, wherein $R^5$ is $C_{3-6}$cycloalkyl.

14. The compound of claim 1, wherein $R^6$ is $C_{3-6}$cycloalkyl.

15. The compound of claim 1, wherein each Ra is independently for each occurrence H, $C_{3-6}$cycloalkyl, $C_{4-11}$cycloalkylalkyl, $C_{6-10}$aryl, $C_{7-16}$arylalkyl, 3-10 membered heteroalicyclyl, 4-11 membered heteroalicyclylalkyl, 5-15 membered heteroaryl or 6-16 membered heteroarylalkyl.

16. The compound of claim 1, wherein each Re is independently for each occurrence $C_{3-6}$cycloalkyl, $C_{4-11}$cycloalkylalkyl, $C_{6-10}$aryl, $C_{7-16}$arylalkyl, 3-10 membered heteroalicyclyl, 4-11 membered heteroalicyclylalkyl, 5-15 membered heteroaryl or 6-16 membered heteroarylalkyl.

* * * * *